(12) United States Patent
Bain et al.

(10) Patent No.: US 11,793,797 B2
(45) Date of Patent: *Oct. 24, 2023

(54) USES OF A LYSYL OXIDASE-LIKE 2 INHIBITOR

(71) Applicant: PHARMAKEA, INC., San Diego, CA (US)

(72) Inventors: Gretchen Bain, San Diego, CA (US); Jillian Frances Evans, San Diego, CA (US); Deidre A. Mackenna, San Diego, CA (US); John Howard Hutchinson, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/331,082

(22) PCT Filed: Sep. 6, 2017

(86) PCT No.: PCT/US2017/050331
§ 371 (c)(1),
(2) Date: Mar. 6, 2019

(87) PCT Pub. No.: WO2018/048942
PCT Pub. Date: Mar. 15, 2018

(65) Prior Publication Data
US 2019/0192495 A1 Jun. 27, 2019

Related U.S. Application Data

(60) Provisional application No. 62/384,542, filed on Sep. 7, 2016, provisional application No. 62/509,460, filed on May 22, 2017.

(51) Int. Cl.
A61K 31/4439 (2006.01)
A61P 35/00 (2006.01)
(Continued)

(52) U.S. Cl.
CPC ........ A61K 31/4439 (2013.01); A61K 31/519 (2013.01); A61K 45/06 (2013.01);
(Continued)

(58) Field of Classification Search
CPC ........................... A61K 31/4439; A61P 35/00
See application file for complete search history.

(56) References Cited

U.S. PATENT DOCUMENTS 4,229,447 A  10/1980 Porter
4,596,795 A   6/1986 Pitha
(Continued)

FOREIGN PATENT DOCUMENTS

EP  0110405 A2  6/1984
EP  0706795 A2  4/1996
(Continued)

OTHER PUBLICATIONS

Nicholas et al, Lung Fibrosis: Fibroblast biology, Thematic Poster Session 2014. (Year: 2014).*
(Continued)

Primary Examiner — Craig D Ricci
Assistant Examiner — Janet L Coppins
(74) Attorney, Agent, or Firm — Maier & Maier, PLLC

(57) ABSTRACT

Described herein is the use of a LOXL2 inhibitor in the treatment or prevention of conditions, diseases, or disorders associated with LOXL2 activity.

15 Claims, 9 Drawing Sheets

(51) Int. Cl.
*A61K 45/06* (2006.01)
*C07D 401/12* (2006.01)
*A61P 19/00* (2006.01)
*A61P 27/02* (2006.01)
*A61P 37/02* (2006.01)
*A61P 1/16* (2006.01)
*A61P 19/02* (2006.01)
*A61P 13/12* (2006.01)
*A61P 29/00* (2006.01)
*A61K 31/519* (2006.01)

(52) U.S. Cl.
CPC .............. *A61P 1/16* (2018.01); *A61P 13/12* (2018.01); *A61P 19/00* (2018.01); *A61P 19/02* (2018.01); *A61P 27/02* (2018.01); *A61P 29/00* (2018.01); *A61P 35/00* (2018.01); *A61P 37/02* (2018.01); *C07D 401/12* (2013.01)

(56) References Cited

U.S. PATENT DOCUMENTS

| | | |
|---|---|---|
| 4,755,386 A | 7/1988 | Hsiao et al. |
| 5,021,456 A | 6/1991 | Palfreyman et al. |
| 5,324,837 A | 6/1994 | Renga et al. |
| 5,691,364 A | 11/1997 | Buckman et al. |
| 5,739,136 A | 4/1998 | Ellinwood, Jr. et al. |
| 6,878,714 B2 | 4/2005 | Askew et al. |
| 6,956,047 B1 | 10/2005 | Chen |
| 6,995,162 B2 | 2/2006 | Chen et al. |
| 7,060,697 B2 | 6/2006 | Marsilje et al. |
| 7,067,664 B1 | 6/2006 | Chen |
| 7,101,868 B2 | 9/2006 | Elbaum et al. |
| 7,102,009 B2 | 9/2006 | Patel et al. |
| 7,105,682 B2 | 9/2006 | Chen et al. |
| 7,307,088 B2 | 12/2007 | Huang et al. |
| 7,378,448 B2 | 5/2008 | Chappell et al. |
| 7,381,750 B2 | 6/2008 | De et al. |
| 7,482,340 B2 | 1/2009 | Otsomaa et al. |
| 7,507,748 B2 | 3/2009 | Yuan et al. |
| 7,514,564 B2 | 4/2009 | Chen et al. |
| 7,687,643 B2 | 3/2010 | Askew et al. |
| 7,723,331 B2 | 5/2010 | Giordanetto et al. |
| 7,759,493 B2 | 7/2010 | Ge et al. |
| 7,902,372 B2 | 3/2011 | Chappell et al. |
| 8,058,445 B2 | 11/2011 | Chen et al. |
| 8,247,430 B2 | 8/2012 | Yuan et al. |
| 8,338,611 B2 | 12/2012 | Chappell et al. |
| 8,343,944 B2 | 1/2013 | Xia et al. |
| 8,642,624 B2 | 2/2014 | Chen et al. |
| 10,150,732 B2 * | 12/2018 | Rowbottom .......... C07D 401/14 |
| 10,570,094 B2 * | 2/2020 | Rowbottom .......... C07D 409/12 |
| 2002/0147198 A1 | 10/2002 | Chen et al. |
| 2004/0087568 A1 | 5/2004 | Huang et al. |
| 2005/0171086 A1 | 8/2005 | Brodney et al. |
| 2006/0040966 A1 | 2/2006 | Yuan et al. |
| 2007/0066658 A1 | 3/2007 | Chappell et al. |
| 2007/0105866 A1 | 5/2007 | Hutchinson et al. |
| 2007/0123522 A1 | 5/2007 | Hutchinson et al. |
| 2007/0149579 A1 | 6/2007 | Blouin et al. |
| 2007/0173508 A1 | 7/2007 | Hutchinson et al. |
| 2007/0219206 A1 | 9/2007 | Hutchinson et al. |
| 2007/0225285 A1 | 9/2007 | Hutchinson et al. |
| 2007/0270430 A1 | 11/2007 | Ice et al. |
| 2008/0004269 A1 | 1/2008 | Xu et al. |
| 2008/0027050 A1 | 1/2008 | Terauchi et al. |
| 2008/0051405 A1 | 2/2008 | Giordanetto et al. |
| 2008/0318926 A1 | 12/2008 | Ice et al. |
| 2009/0143355 A1 | 6/2009 | Yuan et al. |
| 2011/0076272 A1 * | 3/2011 | Smith .................... A61P 35/00 424/133.1 |
| 2011/0136763 A1 | 6/2011 | Xia et al. |
| 2012/0149681 A1 | 6/2012 | Rodgers et al. |
| 2014/0120102 A1 * | 5/2014 | Bornstein .............. A61P 1/16 424/139.1 |
| 2014/0302524 A1 | 10/2014 | Mccauley et al. |
| 2016/0222128 A1 | 8/2016 | Neufeld et al. |
| 2018/0057458 A1 | 3/2018 | Rowbottom et al. |
| 2019/0202805 A1 | 6/2019 | Longergan et al. |
| 2020/0115341 A1 | 4/2020 | Rowbottom et al. |

FOREIGN PATENT DOCUMENTS

| | | | |
|---|---|---|---|
| EP | | 1775347 A2 | 4/2007 |
| WO | WO-9932117 A1 | | 7/1999 |
| WO | WO-0153263 A1 | | 7/2001 |
| WO | WO-03087057 A1 | | 10/2003 |
| WO | WO-2005090286 A1 | | 9/2005 |
| WO | WO-2006053555 A2 | | 5/2006 |
| WO | WO-2007016784 A1 | | 2/2007 |
| WO | WO-2008009963 A2 | | 1/2008 |
| WO | WO-2009017833 A2 | | 2/2009 |
| WO | WO-2011017125 A1 | | 2/2011 |
| WO | WO-2011097594 A2 | | 8/2011 |
| WO | WO-2011109799 A1 | | 9/2011 |
| WO | WO-2011150201 A2 | | 12/2011 |
| WO | WO-2012041476 A1 | | 4/2012 |
| WO | WO-2012068450 A1 | | 5/2012 |
| WO | WO-2013026025 A1 | | 2/2013 |
| WO | WO-2013059587 A1 | | 4/2013 |
| WO | WO-2013161308 A1 | | 10/2013 |
| WO | WO-2014070939 A1 | | 5/2014 |
| WO | WO-2014098098 A1 | | 6/2014 |
| WO | WO-2016020732 A1 | | 2/2016 |
| WO | WO-2016028686 A1 | | 2/2016 |
| WO | WO-2016128529 A1 | | 8/2016 |
| WO | WO-2016144702 A1 | | 9/2016 |
| WO | WO-2016144703 A1 | | 9/2016 |
| WO | WO-2018048942 A1 | | 3/2018 |
| WO | WO-2018048943 A1 | | 3/2018 |

OTHER PUBLICATIONS

Rajagopalan et al, abstract of Eur Resp Journal 2014 (44), pp. 1-5. (Year: 2014).*

Chang et al, Oncotarget 2017, vol. 8 (16), pp. 26066-26078. (Year: 2017).*

Barr et al. American translation, modification, and validation of the St. George's Respiratory Questionnaire. Clin Ther. 22(9):1121-45 (2000).

Barry-Hamilton et al. Allosteric inhibition of lysyl oxidase-like-2 impedes the development of a pathologic microenvironment. Nat Med 16(9):1009-1017 (2010).

Berge et al. Pharmaceutical Salts. Journal of Pharmaceutical Sciences 66(1):1-19 (Jan. 1977).

Chien et al. Serum lysyl oxidase-like 2 levels and idiopathic pulmonary fibrosis disease progression. Eur Respir J 43(5):1430-1438 (2014).

Cosgrove et al. Ultrastructural, physiological, and molecular defects in the inner ear of a gene-knockout mouse model for autosomal Alport syndrome. Hear Res 121:84-98 (1998).

Friedlander. Fibrosis and diseases of the eye. J Clin Invest. 117:576-586 (2007).

Girogescu. Non-invasive Biochemical Markers of Liver Fibrosis. J. Gastrointestin. Liver Dis. 15(2):149-159 (2006).

Ikenaga et al. A new Mdr2(−/−) mouse model of sclerosing cholangitis with rapid fibrosis progression, early-onset portal hypertension, and liver cancer. Am J Pathology 185:325-334 (2015).

Ishii et al. Fluid and Fibrosis in the Human Middle Ear. Am. J Otolaryngol 6(3):196-199 (1985).

Jones et al. A self-complete measure of health status for chronic airflow limitation. Am Rev Respir Dis 145:1321-1327 (1992).

Jones et al. The St. George's Respiratory Questionnaire. Resp Med 85:2531 (1991).

Jones. Interpreting thresholds for a clinically significant change in health status in asthma and COPD. Eur Respir J. 19(3):398-404 (2002).

Li et al. Liver fibrogenesis and the role of hepatic stellate cells: new insights and prospects for therapy. Gastroenterol. Hepatol. 14:618-633 (1999).

(56) References Cited

OTHER PUBLICATIONS

Mehal et al. Scraping fibrosis: expressway to the core of fibrosis. Nat Med. 17:552-553 (2011).
PCT/US2017/050331 International Search Report and Written Opinion dated Nov. 17, 2017.
Popov et al. Tissue transglutaminase does not affect fibrotic matrix stability or regression of liver fibrosis in mice. Gastroenetrology 140(5):1642-1652. (2011).
Sato et al. Comparative analysis of gene expression profiles in intact and damaged regions of human osteoarthritic cartilage. Arthritis & Rheumatism 54(3):808-817 (2006).
Schena et al. Pathogenic Mechanisms ofDiabetic Nephropathy. J. Am. Soc. Nephrol. 16:S30-33 (2005).
Tolboom et al. Invasiveness of fibroblast-like synoviocytes is an individual patient characteristic associated with the rate of joint destruction in patients with rheumatoid arthritis. Arthritis Rheum 52:1999-2002 (2005).
Van Bergen et al. The role of LOX and LOXL2 in scar formation after glaucoma surgery. Invest Ophthalmol Vis Sci. 54:5788-5796 (2013).
Van Bergen et al. The Role of LOX and LOXL2 in the Pathogenesis of an Experimental Model of Choroidal Neovascularization. Invest Ophthalmol Vis Sci 56(9):5280-5289 (2015).
Whaley-Cannell et al. Chronic Kidney Disease and the Cardiometabolic Syndrome. J. Clin. Hypert. 8(8):546-48 (2006).
Bertini et al. Alkylamino derivatives of 4-aminomethylpyridine as inhibitors of copper-containing amine oxidases. J Med Chem 48(3):664-670 (2005).
Cano et al. LOXL2 in epithelial cell plasticity and tumor progression. Future Oncol 8(9):1095-1108 (2012).
Hase et al. LOXL2 Status Correlates with Tumor Stage and Regulates Integrin Levels to Promote Tumor Progression in ccRCC. Mol Cancer Res 12(12):1807-1817 (2014).
Hutchinson et al. Small Molecule Lysyl Oxidase-like 2 (LOXL2) Inhibitors: The Identification of an Inhibitor Selective for LOXL2 over LOX. ACS Med. Chem. Lett. 8(4):423-427 (2017).
Rodriguez et al. Modulation of lysyl oxidase-like 2 enzymatic activity by an allosteric antibody inhibitor. J Biol Chem 285(27):20964-20974 (2010).
Rowbottom et al. Identification of 4-(Aminomethyl)-6-(trifluoromethyl)-2-(phenoxy)pyridine Derivatives as Potent, Selective, and Orally Efficacious Inhibitors of the Copper-Dependent Amine Oxidase, Lysyl Oxidase-Like 2 (LOXL2). J Med Chem 50:4403-4423 (2017).
Tang et al. Beta-substituted ethylamine derivatives as suicide inhibitors of lysyl oxidase. J Biol Chem 259(2):975-979 (1984).
Williamson et al. Electronegativity of aromatic amines as a basis for the development of ground state inhibitors of lysyl oxidase. J Biol Chem 262(30):14520-14524 (1987).
Wuest et al. Targeting lysyl oxidase for molecular imaging in breast cancer. Breast Cancer Research 17:107 (2015).
Zablocki et al. Potent in vitro and in vivo inhibitors of platelet aggregation based upon the Arg-Gly-Asp sequence of fibrinogen. (Aminobenzamidino)succinyl (ABAS) series of orally active fibrinogen receptor antagonists. J Med Chem 38:2378-2394 (1995).
Erasmus et al. Linking LOXL2 to Cardiac Interstitial Fibrosis. Int J Mol Sci. 21(16):5913 (2020).
Ikenaga et al. Selective targeting of lysyl oxidase-like 2 (LOXL2) suppresses hepatic fibrosis progression and accelerates its reversal. Gut 66(9):1697-1708 (2017).
Klepfish et al. LOXL2 Inhibition Paves the Way for Macrophage-Mediated Collagen Degradation in Liver Fibrosis. Front Immunol. 11:480 (2020).
Mahjour et al. Mechanism for oral tumor cell lysyl oxidaselike-2 in cancer development: synergy with PDGF-AB. Oncogenesis 8:34 (2019).
Matsuoka et al. Wnt signaling and Loxl2 promote aggressive osteosarcoma. Cell research 30:885-901 (2020).
Moon et al. Human lysyl oxidase-like 2. Bioorg. Chem. 57:231-241 (2014).
Papadantonakis et al. Megakaryocyte pathology and bone marrow fibrosis: the lysyl oxidase connection. Blood. 120(9):1774-1781 (2012).
Puente et al. LOXL2—A New Target in Antifibrogenic Therapy? Int J Mol Sci. 20(7):1634 (2019).
Stagenberg et al. Lysyl oxidase-like 2 inhibition ameliorates glomerulosclerosis and albuminuria in diabetic nephropathy. Scientific reports 8:9423 (2018).
Tadmor et al. The expression of lysyl-oxidase gene family members in myeloproliferative neoplasms. Am J Hematol 88(5):355-358 (2013).
Wu et al. The function and mechanisms of action of LOXL2 in cancer (Review). Int J Mol Sci. 36(5):1200-1204 (2015).
Xiao et al. Lysyl oxidase, extracellular matrix remodeling and cancer metastasis. Cancer Microenviron. 5(3):261-273 (2012).
Xie et al. Inhibition of LOXL2 Enhances the Radiosensitivity of Castration-Resistant Prostate Cancer Cells Associated with the Reversal of the EMT Process. Biomed Res Int 2019:4012590 (2019).
Yang et al. Targeting LOXL2 for cardiac interstitial fibrosis and heart failure treatment. Nat Commun 7:13710 (2016).

\* cited by examiner

USES OF A LYSYL OXIDASE-LIKE 2 INHIBITOR

RELATED APPLICATIONS

This application is filed pursuant to 35 U.S.C. § 371 as a United States National Phase Application of International Application No. PCT/US2017/050331 entitled "USES OF A LYSYL OXIDASE-LIKE 2 INHIBITOR" filed Sep. 6, 2017, which claims the benefit of U.S. Provisional Patent Application No. 62/384,542 entitled "USES OF A LYSYL OXIDASE-LIKE 2 INHIBITOR" filed on Sep. 7, 2016 and U.S. Provisional Patent Application No. 62/509,460 entitled "USES OF A LYSYL OXIDASE-LIKE 2 INHIBITOR" filed on May 22, 2017, each of which is incorporated herein by reference in their entirety.

FIELD OF THE INVENTION

Described herein are methods of using a lysyl oxidase-like 2 (LOXL2) inhibitor in the treatment or prevention of conditions, diseases, or disorders associated with LOXL2 activity.

BACKGROUND OF THE INVENTION

Lysyl oxidase like-2 (LOXL2) is an amine oxidase enzyme that catalyzes crosslinking of extracellular matrix proteins. LOXL2 is also involved in intracellular processes such as mediating epithelial-to-mesenchymal transition of cells. LOXL2 signaling is implicated in, for example, in fibrotic diseases and cancer. There is an unmet medical need for therapies that could provide benefit to patients with fibrotic diseases and cancer.

SUMMARY OF THE INVENTION

Described herein is the use of a small molecule LOXL2 inhibitor in the treatment of disease or condition in a mammal that would benefit from inhibition or reduction of LOXL2 activity, wherein the small molecule LOXL2 inhibitor is more selective for inhibiting or binding to LOXL2 than for LOX. In some embodiments, the small molecule LOXL2 inhibitor is at least 10 times more selective for inhibiting or binding to LOXL2 than for LOX. In some embodiments, the small molecule LOXL2 inhibitor is at least 10 times, at least 20 times, at least 30 times, at least 40 times, at least 50 times, at least 60 times, at least 70 times, at least 80 times, at least 90 times, or more than 100 times more selective for inhibiting or binding to LOXL2 than for LOX. In some embodiments, the small molecule LOXL2 inhibitor is at least 100 times more selective for inhibiting or binding to LOXL2 than for LOX. In some embodiments, the small molecule LOXL2 inhibitor is at least 100 times, at least 120 times, at least 140 times, at least 160 times, at least 180 times, at least 200 times, at least 250 times, at least 300 times, at least 350 times, or at least 400 times more selective for LOXL2 than for LOX. In some embodiments, the small molecule LOXL2 inhibitor is at least 400 times more selective for LOXL2 than for LOX.

In one aspect, the disease or condition is lung disease, liver disease, kidney disease, fibrosis of the heart, fibrosis of the eye, ear fibrosis, myelofibrosis, scleroderma, cancer, an autoimmune disease or condition, an inflammatory disease or condition, or combination thereof.

In one aspect, small molecule LOXL2 inhibitor is trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof.

In some embodiments, the small molecule LOXL2 inhibitor is (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, or a mixture thereof. In some embodiments, the small molecule LOXL2 inhibitor is (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof. In some embodiments, (R,R)-trans-(3-((4-(aminomethyl)-6-(trifluoromethyl)pyridin-2-yl)oxy)phenyl)(3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the pharmaceutically acceptable salt of (R,R)-trans-(3-((4-(aminomethyl)-6-(trifluoromethyl)pyridin-2-yl)oxy)phenyl)(3-fluoro-4-hydroxypyrrolidin-1-yl)methanone is formed from (R,R)-trans-(3-((4-(aminomethyl)-6-(trifluoromethyl)pyridin-2-yl)oxy)phenyl)(3-fluoro-4-hydroxypyrrolidin-1-yl)methanone and an acid selected from the group consisting of hydrochloride acid, hydrobromic acid, sulfuric acid, phosphoric acid, nitric acid, metaphosphoric acid, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid. In some embodiments, the (R,R)-trans-(3-((4-(aminomethyl)-6-(trifluoromethyl)pyridin-2-yl)oxy)phenyl)(3-fluoro-4-hydroxypyrrolidin-1-yl)methanone is used as the mesylate salt, hydrochloride salt, sulfate salt, maleate salt, phosphate salt, L-tartrate salt, fumarate salt, succinate salt, citrate salt or acetate salt. In some embodiments, the (R,R)-trans-(3-((4-(aminomethyl)-6-(trifluoromethyl)pyridin-2-yl)oxy)phenyl)(3-fluoro-4-hydroxypyrrolidin-1-yl)methanone is used as the mesylate salt.

In some embodiments, the small molecule LOXL2 inhibitor is (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof. In some embodiments, (S,S)-trans-(3-((4-(aminomethyl)-6-(trifluoromethyl)pyridin-2-yl)oxy)phenyl)(3-fluoro-4-hydroxypyrrolidin-1-yl)methanone is substantially free of (R,R)-trans-(3-((4-(aminomethyl)-6-(trifluoromethyl)pyridin-2-yl)oxy)phenyl)(3-fluoro-4- hydroxypyrrolidin-1-yl)methanone, or a pharmaceutically acceptable salt or solvate thereof. In some embodiments, the pharmaceutically acceptable salt of (S,S)-trans-(3-((4-(aminomethyl)-6-(trifluoromethyl)pyridin-2-yl)oxy)phenyl)(3-fluoro-4-hydroxypyrrolidin-1-yl)methanone is formed from (S,S)-trans-(3-((4-(aminomethyl)-6-(trifluoromethyl)pyridin-2-yl)oxy)phenyl)(3-fluoro-4-hydroxypyrrolidin-1-yl)methanone and an acid selected from the group consisting of hydrochloride acid, hydrobromic acid, sulfuric acid, phosphoric acid, nitric acid, metaphosphoric acid, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid. In some embodiments, (S,S)-trans-(3-((4-(aminomethyl)-6-(trifluoromethyl)pyridin-2-yl)oxy)phenyl)(3-fluoro-4-hydroxypyrrolidin-1-yl)methanone is used as the mesylate salt, hydrochloride salt, sulfate salt, maleate salt, phosphate salt, L-tartrate salt, fumarate salt, succinate salt, citrate salt or acetate salt. In some embodiments, (S,S)-trans-(3-((4-(aminomethyl)-6-(trifluoromethyl)pyridin-2-yl)oxy)phenyl)(3-fluoro-4-hydroxypyrrolidin-1-yl)methanone is used as the mesylate salt.

Described herein is the compound (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, or a mixture thereof. In some embodiments, (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, or a mixture thereof, is used in the treatment or prevention of diseases or conditions that are associated with LOXL2 activity. In some embodiments, (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy) phenyl)(3-fluoro-4-hydroxypyrrolidin-1-yl)methanone or a pharmaceutically acceptable salt or solvate thereof, or a mixture thereof, is used in the treatment or prevention of diseases or conditions that are described herein. In some embodiments the hydrochloride salt of (R,R)-trans-(3-((4-(aminomethyl)-6-(trifluoromethyl)pyridin-2-yl)oxy)phenyl) (3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy) phenyl)(3-fluoro-4-hydroxypyrrolidin-1-yl)methanone or a pharmaceutically acceptable salt or solvate thereof, or a mixture thereof, is used. In some embodiments, the mesylate salt of (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, or a mixture thereof is used.

Described herein is the compound (R,R)-trans-(3-((4-(aminomethyl)-6-(trifluoromethyl)pyridin-2-yl)oxy)phenyl) (3-fluoro-4-hydroxypyrrolidin-1-yl)methanone (Compound I), or a pharmaceutically acceptable salt or solvate thereof. In some embodiments, Compound I, or a pharmaceutically acceptable salt or solvate thereof, is used in the treatment or prevention of diseases or conditions that are associated with LOXL2 activity. In some embodiments, Compound I, or a pharmaceutically acceptable salt or solvate thereof, is used in the treatment or prevention of diseases or conditions that are described herein. In some embodiments the hydrochloride salt of Compound I is used (i.e. Compound 1). In some embodiments, the mesylate salt of Compound I is used (i.e. Compound 2).

In one aspect, described herein is a method for treating or preventing lung disease in a mammal, comprising administering to the mammal the compound (R,R)-trans-(3-((4-(aminomethyl)-6-(trifluoromethyl)pyridin-2-yl)oxy)phenyl) (3-fluoro-4-hydroxypyrrolidin-1-yl)methanone (Compound I), or a pharmaceutically acceptable salt or solvate thereof. In some embodiments, the compound (R,R)-trans-(3-((4-(aminomethyl)-6-(trifluoromethyl)pyridin-2-yl)oxy)phenyl) (3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as the mesylate salt (Compound 2), or solvate thereof.

In some embodiments, the lung disease is lung fibrosis. In some embodiments, the lung disease is interstitial lung disease (ILD). In some embodiments, the lung disease is idiopathic interstitial pneumonia, connective tissue disease-associated interstitial lung disease (CTD-ILD), sarcoidosis, hypersensitivity pneumonitis, iatrogenic pneumonitis/fibrosis (drug-induced ILD, radiation injury), eosinophilic ILD (e.g. eosinophilic pneumonia), occupational lung disease, familial pulmonary fibrosis, Hermansky-Pudlak syndrome), or pulmonary Langerhans cell histiocytosis. In some embodiments, the lung disease is Idiopathic pulmonary fibrosis (IPF), Non-specific interstitial pneumonia (NSIP), Cryptogenic organizing pneumonia (COP), Respiratory bronchiolitis interstitial lung disease (RBILD), Desquamative interstitial pneumonia (DIP), acute interstitial pneumonia (AIP), or lymphoid interstitial pneumonia (LIP). In some embodiments, the lung disease is idiopathic pulmonary fibrosis (IPF). In some embodiments, the compound reduces serum LOXL2 (sLOXL2) levels in the mammal. In some embodiments, the compound slows the decline in lung function, reduces the frequency of exacerbations of the lung disease, improves survival of the mammal with lung disease, or combinations thereof.

In some embodiments of the treatment or prevention of lung disease, the method further comprises administering at least one additional therapeutic to the mammal. In some embodiments, the at least one additional therapeutic agent is a vaccination against pneumonia, a cough suppression medication, a corticosteroid, an immunosuppressant, N-acetyl cysteine (NAC), pirfenidone, nintedinab, or combinations thereof. In some embodiments, the mammal is a human. In some embodiments, the human is an adult human.

In some embodiments, the lung disease is pulmonary alveolar proteinosis (PAP). In some embodiments of the treatment or prevention of lung disease (e.g. PAP), the method further comprises whole-lung lavage, administering at least one additional therapeutic agent, or combinations thereof. In some embodiments, the at least one additional therapeutic agent is a corticosteroid, a mucolytic, or a proteinase inhibitor.

In some embodiments of the treatment or prevention of lung disease, the compound, or a pharmaceutically acceptable salt or solvate thereof, is systemically administered to the mammal. In some embodiments of the treatment or prevention of lung disease, the compound, or a pharmaceutically acceptable salt or solvate thereof, is administered to the mammal orally, by injection or intravenously. In some embodiments of the treatment or prevention of lung disease the compound, or a pharmaceutically acceptable salt or solvate thereof, is administered to the mammal in the form of an oral solution, oral suspension, powder, pill, tablet or capsule. In some embodiments of the treatment or prevention of lung disease the compound, or a pharmaceutically acceptable salt or solvate thereof, is administered directly to the lungs of the mammal.

In some embodiments of the treatment or prevention of lung disease, the compound, or a pharmaceutically acceptable salt or solvate thereof, is administered directly to the lungs of the mammal with the use of a nebulizer, metered-dose inhaler, or dry powder inhaler.

In one aspect, described herein is a method for treating or preventing liver disease in a mammal, comprising administering to the mammal the compound (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I), or a pharmaceutically acceptable salt or solvate thereof. In some embodiments, wherein the compound (R,R)-trans-(3-((4-(aminomethyl)-6-(trifluoromethyl)pyridin-2-yl)oxy)phenyl)(3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as the mesylate salt (Compound 2), or solvate thereof.

In some embodiments, the liver disease is a fibrotic liver disease. In some embodiments, the liver disease is a fibrotic liver disease resulting from hepatitis C virus (HCV), non-alcoholic steatohepatitis (NASH), primary sclerosing cholangitis (PSC), cirrhosis, liver fibrosis, alpha 1 antitrypsin deficiency disease, hereditary hemochromatosis, Wilson's disease, hepatitis B virus (HBV), and HIV associated steatohepatitis and cirrhosis, and associated conditions such as chronic viral hepatitis, non-alcoholic fatty liver disease (NAFLD), alcoholic steatohepatitis (ASH), nonalcoholic steatohepatitis (NASH), primary biliary cirrhosis (PBC), or biliary cirrhosis. In some embodiments, the liver disease is a fibrotic liver disease resulting from hepatitis C infection, non-alcoholic steatohepatitis (NASH), alcoholic steatohepatitis (ASH), Wilson's disease, and primary biliary cirrhosis, or sclerosing cholangitis. In some embodiments, the liver disease is a fibrotic human liver disease resulting from non-alcoholic fatty liver disease (NAFLD). In some embodiments, the liver disease is a fibrotic human liver disease resulting from a viral hepatitic disease or condition. In some embodiments, the liver disease is liver fibrosis and the mammal is a human diagnosed with NASH. In some embodiments, the liver disease is liver fibrosis and the mammal is a human diagnosed with primary sclerosing cholangitis (PSC). In some embodiments, the liver disease is cirrhosis due to NASH.

In some embodiments of the treatment or prevention of liver disease, the method further comprises administering at least one additional therapeutic to the mammal. In some embodiments, the at least one additional therapeutic agent is selected from the group consisting of PPAR agonists, Incretins, Glut2-I, FXR agonists, antioxidants, GLP-1 modulators, SGLT-2 inhibitors, Bile acids, Caspase protease inhibitors, Synthetic fatty acid/bile acid conjugates, dual CCR2/CC5 antagonists, Immunomodulators, Sirtuin stimulants, Fatty acid inhibitor, DGAT1 inhibitors, CD3 antigens, PDE-4 modulators, AMPK stimulants, ROCK2 inhibitors, ASBT inhibitors, ASK1 inhibitors, TLR-4 antagonists, THR beta agonists, Cathepsin B inhibitors, Galectin-3 modulators, and combinations thereof.

In some embodiments of the treatment or prevention of liver disease, the compound, or a pharmaceutically acceptable salt or solvate thereof, is systemically administered to the mammal. In some embodiments, the compound, or a pharmaceutically acceptable salt or solvate thereof, is administered to the mammal orally, by injection or intravenously. In some embodiments, the compound, or a pharmaceutically acceptable salt or solvate thereof, is administered to the mammal in the form of an oral solution, oral suspension, powder, pill, tablet or capsule.

In one aspect, described herein is a method for treating or preventing fibrosis of the kidney, fibrosis of the heart, fibrosis of the eye, ear fibrosis, myelofibrosis, or scleroderma in a mammal, comprising administering to the mammal the compound (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I), or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as the mesylate salt (Compound 2), or solvate thereof.

In some embodiments, the myelofibrosis is primary myelofibrosis or secondary myelofibrosis. In some embodiments, the myelofibrosis is primary, post polycythemia vera or post essential thrombocythemia myelofibrosis. In some embodiments of the treatment or prevention of myelofibrosis, the method further comprises administering at least one additional therapeutic to the mammal. In some embodiments, the at least one additional therapeutic agent is ruxolitinib.

In some embodiments, the scleroderma is limited systemic sclerosis or diffuse systemic sclerosis.

In some embodiments, the fibrosis of the eye comprises fibrosis of the vitreous, iris, ciliary body, lens, choroid, retinal pigment epithelium, cornea, retina, or combinations thereof.

In some embodiments, the fibrosis of the eye is a result of eye surgery.

In some embodiments, the mammal is diagnosed with glaucoma, age related macular degeneration (AMD), choroidal neovascularization (CNV), corneal degeneration, dry eye syndrome, keratitis, corneal ulcers, retinopathy of prematurity (ROP), pterygia, cataracts, diabetic retinopathy with retinal edema and neovascularization, proliferative vitreoretinopathy (PVR), retinal detachment, macular edema.

In some embodiments of the treatment or prevention of fibrotic disease, administering at least one additional therapeutic to the mammal.

In some embodiments, the compound, or a pharmaceutically acceptable salt or solvate thereof, is systemically administered to the mammal. In some embodiments, the compound, or a pharmaceutically acceptable salt or solvate thereof, is administered to the mammal orally, by injection or intravenously.

In one aspect, described herein is a method for treating or preventing cancer in a mammal, comprising administering to the mammal the compound (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I), or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as the mesylate salt (Compound 2), or solvate thereof.

In some embodiments, the cancer is breast cancer, colon cancer, gastric cancer, head and neck cancer, lung cancer, melanoma, or combinations thereof. In some embodiments, the cancer is colon cancer, esophageal tumors, oral squamous cell carcinomas, laryngeal squamous cell carcinomas, and head and neck squamous cell carcinomas.

In some embodiments of the treatment or prevention of cancer, the method further comprises administering at least one additional therapeutic to the mammal. In some embodiments, the at least one additional therapeutic agent is an anti-cancer agent.

In some embodiments, the compound, or a pharmaceutically acceptable salt or solvate thereof, is systemically administered to the mammal. In some embodiments, the compound, or a pharmaceutically acceptable salt or solvate thereof, is administered to the mammal orally, by injection or intravenously.

In one aspect, described herein is a method for treating or preventing an autoimmune disease or condition or an inflammatory disease or condition in a mammal, comprising administering to the mammal the compound (R,R)-trans-(3-((4-(aminomethyl)-6-(trifluoromethyl)pyridin-2-yl)oxy)phenyl)(3-fluoro-4-hydroxypyrrolidin-1-yl)methanone (Compound I), or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is substantially free of (S,S)-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof. In some embodiments, the compound (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as the mesylate salt (Compound 2), or solvate thereof.

In some embodiments, the autoimmune disease or condition is rheumatoid arthritis, juvenile idiopathic arthritis, psoriatic arthritis, osteoarthritis, Still's disease, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. In some embodiments, the autoimmune disease or condition is rheumatoid arthritis, juvenile idiopathic arthritis, psoriatic arthritis, osteoarthritis, or ankylosing spondylitis.

In some embodiments, the inflammatory disease or condition is asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In some embodiments of the treatment or prevention of autoimmune disease or condition or an inflammatory disease or condition, the method further comprises administering at least one additional therapeutic to the mammal. In some embodiments, the mammal is a human.

In some embodiments, the compound, or a pharmaceutically acceptable salt or solvate thereof, is systemically administered to the mammal. In some embodiments, the compound, or a pharmaceutically acceptable salt or solvate thereof, is administered to the mammal orally, by injection or intravenously. In some embodiments, the compound, or a pharmaceutically acceptable salt or solvate thereof, is administered to the mammal in the form of an oral solution, oral suspension, powder, pill, tablet or capsule.

In one aspect, described herein is a pharmaceutical composition comprising Compound I, or a pharmaceutically acceptable salt or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In one aspect, described herein is a method of treating a disease or condition in a mammal that would benefit from the inhibition or reduction of Lysyl oxidase like-2 (LOXL2) activity comprising administering Compound I, or a pharmaceutically acceptable salt or solvate thereof, to the mammal in need thereof. In some embodiments, the disease or condition is fibrosis or cancer. In some embodiments, the fibrosis comprises lung fibrosis, liver fibrosis, kidney fibrosis, cardiac fibrosis, peritoneal fibrosis, ocular fibrosis, ear fibrosis or cutaneous fibrosis. In some embodiments, the fibrosis is myelofibrosis.

In one aspect, described herein is a method of treating or preventing any one of the diseases or conditions described herein comprising administering a therapeutically effective amount of Compound I, or a pharmaceutically acceptable salt or solvate thereof, to a mammal in need thereof.

In one aspect, described herein is a method for the treatment or prevention of fibrosis in a mammal comprising administering a therapeutically effective amount of Compound I, or a pharmaceutically acceptable salt or solvate thereof, to the mammal in need thereof. In other embodiments, the fibrosis is amenable to treatment with a LOXL2 inhibitor. In some embodiments, the fibrosis is lung fibrosis. In some embodiments, the method further comprises administering a second therapeutic agent to the mammal in addition to the Compound I, or a pharmaceutically acceptable salt or solvate thereof.

In any of the aforementioned aspects are further embodiments in which the effective amount of Compound I, or a pharmaceutically acceptable salt or solvate thereof, is: (a) systemically administered to the mammal; and/or (b) administered orally to the mammal; and/or (c) intravenously administered to the mammal; and/or (d) administered by inhalation; and/or (e) t administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of Compound I, or a pharmaceutically acceptable salt or solvate thereof, including further embodiments in which Compound I, or a pharmaceutically acceptable salt or solvate thereof, is administered once a day to the mammal or Compound I, or a pharmaceutically acceptable salt or solvate thereof, is administered to the mammal multiple times over the span of one day. In some embodiments, Compound I, or a pharmaceutically acceptable salt or solvate thereof, is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of Compound I, or a pharmaceutically acceptable salt or solvate thereof. In various embodiments, each agent is administered in any order, including simultaneously.

In any of the embodiments disclosed herein, the mammal is a human.

In some embodiments, Compound I, or a pharmaceutically acceptable salt or solvate thereof, is administered to a human. In some embodiments, Compound I, or a pharmaceutically acceptable salt or solvate thereof, is orally administered. In some embodiments, oral administration is accomplished by the use of tablets comprising Compound I, or a pharmaceutically acceptable salt or solvate thereof.

Articles of manufacture, which include packaging material, a compound described herein, or a pharmaceutically acceptable salt thereof, within the packaging material, and a label that indicates that Compound I, or a pharmaceutically acceptable salt or solvate thereof, is used for inhibiting the activity of LOXL2, or for the treatment, prevention or amelioration of one or more symptoms of a disease or condition that would benefit from inhibition or reduction of the LOXL2 activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
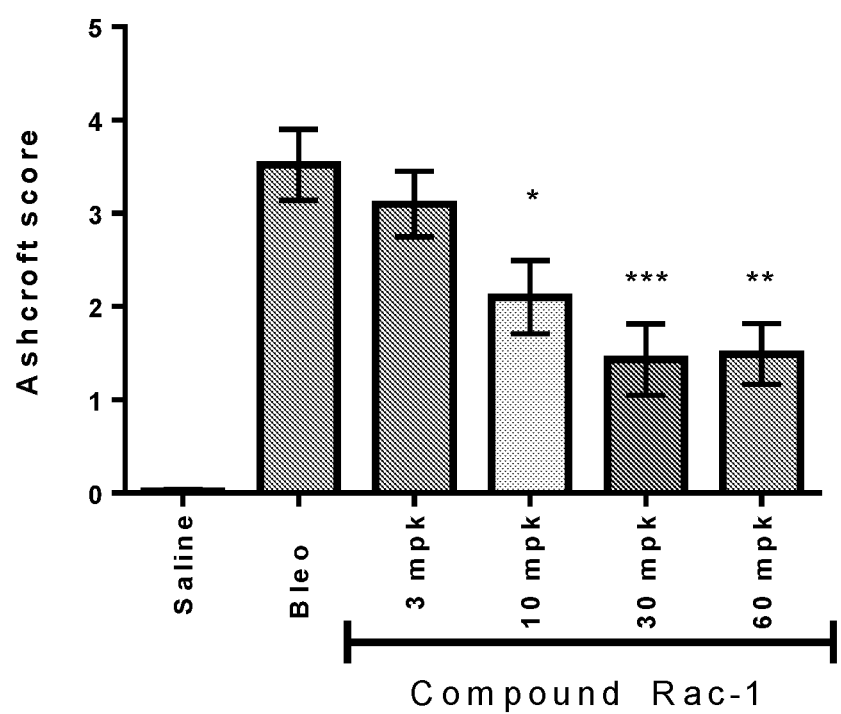
FIG. 1 shows the Ashcroft scores derived from histopathology analyses of trichrome stained lung sections and which reflects lung fibrosis in a prophylactic 14-day dose response study of Rac-1 in the mouse bleomycin-induced model of lung fibrosis (*$p<0.05$; $p<0.01$; *$p<0.001$). The data show that Rac-1 reduced fibrosis in a dose-related manner and that 30 mg/kg QD is the minimal dose to achieve maximal anti-fibrotic efficacy.

Lysyl oxidase like-2 (LOXL2) is a member of the lysyl oxidase (LOX) family, which comprises $Cu^{2+}$ and lysine tyrosylquinone (LTQ)-dependent amine oxidases. The family comprises five genes: lox (LOX), loxl1 (lysyl oxidase like-1, LOXL1), loxl2 (LOXL2), loxl3 (lysyl oxidase like-3, LOXL3), and loxl4 (lysyl oxidase like-4, LOXL4). The LOX family is known for catalyzing the oxidative deamination of the ε-amino group of lysines and hydroxylysines in collagen and elastin to promote crosslinking of these molecules. Crosslinking of collagen and elastin is essential for maintaining tensile strength of the extracellular matrix.

The development of pathologic stroma plays an important role in disease. Pathologic stroma is composed of activated stromal cells, collagenous matrix, growth factors, and angiogenic structures. During pathologic conditions such as fibrogenesis, fibroblasts are recruited and activated resulting in the generation of a microenvironment that fosters increased synthesis and deposition of extracellular matrix proteins leading to the development of fibrosis.

Disease-associated fibroblast activation in fibrotic disease and cancer results in remodeling of the extracellular matrix that ultimately leads to excessive deposition of extracellular matrix proteins, including collagen I and III, increased cross-linking of the newly deposited collagen and enhanced tissue stiffness. In addition, activated fibroblasts express numerous pro-angiogenic, pro-vasculogenic, and pro-proliferative growth factors and cytokines such as transforming growth factor beta (TGF-β), connective tissue growth factor (CTGF), stromal cell-derived factor 1 (SDF-1), and vascular endothelial growth factor (VEGF), thereby playing important roles in paracrine signaling in disease progression. Disrupting the development of this pathologic stroma through inhibition of fibroblast activation and recruitment and/or their signaling pathways represents a novel therapeutic strategy in fibrotic disease.

Despite similar catalytic activity, each lysyl oxidase enzyme has been reported to have unique expression and functional activities. LOXL2 plays a central role in the development of pathologic stroma in fibrotic diseases by activating and recruiting fibroblasts to the pathologic site.

LOXL2 has been demonstrated to have intracellular functions aside from its role in remodeling of the extracellular matrix. LOXL2 positively regulates the epithelial-to-mesenchymal transition (EMT) transducer, Snail1, by promoting Snail1 stability and functional activity. LOXL2 contributes positively to the activation of the focal adhesion kinase (FAK) signaling pathway and participates in the organization of focal adhesion complexes. Silencing of LOXL2 gene leads to reacquisition of epithelial cell polarity and decreases the migratory and invasive ability of mammary cell lines. The modulation of cell adhesion and cell polarity has been reported to be mediated by intracellular LOXL2. LOXL2 transcriptionally represses E-cadherin as well as tight junction and cell polarity genes by Snail1-dependent and Snail1-independent mechanisms. LOXL2 has been more recently described to be associated with chromatin and reported to be involved in histone H3 trimethyl deamination, a function that is dependent on the LOXL2 catalytic domain.

In some embodiments, the methods disclosed herein are methods for inhibiting intracellular LOXL2. In some embodiments, the methods disclosed herein are methods for inhibiting extracellular (secreted) LOXL2. In some embodiments, the methods disclosed herein are methods for inhibiting extracellular and intracellular LOXL2.

Fibrosis

LOXL2 is involved in fibrotic processes. Fibrotic processes include an excessive deposition of extracellular matrix components, such as collagen, which alters the physical, biochemical and biomechanical matrix properties leading to defective organ function and organ failure. Tissue fibrosis is also associated with cancer progression by direct promotion of cellular transformation and metastasis. Tumors are typically stiffer than normal tissue and tumor rigidity influences tumor metastasis.

Excessive LOXL2 enzyme activity has been implicated in the increased stiffness of tumors. Elevated LOXL2 is also associated with fibrotic lesions from livers of patients suffering from Wilson disease, primary biliary cirrhosis and NASH. Additionally, the administration of a LOXL2-specific monoclonal antibody, AB0023, was efficacious in reducing disease in a model of fibrosis. AB0023 was shown to inhibit the production of growth factors and of crosslinked collagenous matrix and TGF-beta signaling.

LOXL2 promotes type I collagen cross-linking and is a core regulator of fibrogenesis of various etiologies and in various organs. Levels of circulating LOXL2 correlate with fibrotic stage. LOXL2 is a core pathway target in fibrotic disease. Mehal et al. "Expressway to the core of fibrosis," *Nat Med*. 2011. 17: 552-553.

There is little LOXL2 expression in healthy adult tissues and under normal (e.g., non-disease) conditions, the amount of circulating LOXL2 is low. Under certain disease conditions, circulating LOXL2 is elevated. For example, LOXL2 can be elevated in the serum of patients with lung fibrosis and chronic liver disease, such as in chronic hepatitis C patients, with greater levels in patients with more advanced fibrosis. Detection of circulating LOXL2 is useful for determining whether an individual has a disease that results in elevated circulating LOXL2 levels. Such diseases include fibrosis and cancer.

It has been found that the level of circulating LOXL2 correlates with the stage of fibrosis. It has also been found that the level of circulating LOXL2 can provide an indication as to whether an individual having fibrosis is amenable to treatment for the fibrosis and provide other prognostic and predictive information regarding disease, such as the likelihood of a particular endpoint, outcome, or event, such as disease outcome or responsiveness to treatment.

In some embodiments, disclosed herein is the use of Compound I, or a pharmaceutically acceptable salt or solvate thereof, in the treatment or prevention of fibrosis in a mammal.

"Fibrosis," as used herein, refers to the accumulation of extracellular matrix constituents that occurs following trauma, inflammation, tissue repair, immunological reactions, cellular hyperplasia, and neoplasia.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, the fibrosis comprises lung fibrosis, liver fibrosis, kidney fibrosis, cardiac fibrosis, peritoneal fibrosis, ocular fibrosis or cutaneous fibrosis. In some embodiments, the fibrosis comprises lung fibrosis. In some embodiments, the fibrosis comprises liver fibrosis. In some embodiments, the fibrosis comprises kidney fibrosis. In some embodiments, the fibrosis comprises cardiac fibrosis. In some embodiments, the fibrosis comprises peritoneal fibrosis. In some embodiments, the fibrosis comprises ocular fibrosis. In some embodiments, the fibrosis comprises cutaneous fibrosis.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is a fibrotic condition of the lung.

In some embodiments, the fibrotic condition is a fibrotic condition of the liver.

In some embodiments, the fibrotic condition is a fibrotic condition of the heart.

In some embodiments, the fibrotic condition is a fibrotic condition of the kidney.

In some embodiments, the fibrotic condition is a fibrotic condition of the skin.

In some embodiments, the fibrotic condition is a fibrotic condition of the eye.

In some embodiments, the fibrotic condition is a fibrotic condition of the gastrointestinal tract.

In some embodiments, the fibrotic condition is a fibrotic condition of the bone marrow.

In some embodiments, the fibrotic condition is a fibrotic condition of the ear.

In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, disclosed herein is a method for the treatment or prevention of fibrosis in a mammal comprising administering a LOXL2 inhibitor described herein, or a pharmaceutically acceptable salt thereof, to the mammal in need thereof.

In some embodiments, disclosed herein is a method of improving lung function in a mammal comprising administering a LOXL2 inhibitor described herein, or a pharmaceutically acceptable salt thereof, to the mammal in need thereof. In some embodiments, the mammal has been diagnosed as having lung fibrosis.

In some embodiments, disclosed herein is a method of treating idopathic pulmonary fibrosis in a mammal comprising administering a LOXL2 inhibitor described herein, or a pharmaceutically acceptable salt thereof, to the mammal in need thereof.

In some embodiments, disclosed herein is a method of controlling an abnormal accumulation or activation of cells, fibronectin, collagen or increased fibroblast recruitment in a tissue of a mammal comprising administering a LOXL2 inhibitor described herein, or a pharmaceutically acceptable salt thereof, to the mammal in need thereof. In some embodiments, the abnormal accumulation or activation of cells, fibronectin, collagen or increased fibroblast recruitment in the tissue results in fibrosis.

In some embodiments, disclosed herein is a method for the treatment or prevention of scleroderma in a mammal comprising administering a LOXL2 inhibitor described herein, or a pharmaceutically acceptable salt thereof, to the mammal in need thereof.

In some embodiments, disclosed herein is a method for reducing undesired or abnormal dermal thickening in a mammal comprising administering to mammal in need thereof a LOXL2 inhibitor described herein, or a pharmaceutically acceptable salt thereof. In some embodiments, the dermal thickening is associated with scleroderma.

In some embodiments, described herein is a method of controlling an abnormal accumulation or activation of cells, fibronectin, collagen or increased fibroblast recruitment in tissues of a mammal comprising administering to mammal in need thereof a LOXL2 inhibitor described herein, or a pharmaceutically acceptable salt thereof. In some embodiments, the abnormal accumulation or activation of cells, fibronectin, collagen or increased fibroblast recruitment in the dermal tissues results in fibrosis. In some embodiments, described herein is a method of reducing hydroxyproline content in tissues of a mammal with fibrosis comprising administering to mammal in need thereof a LOXL2 inhibitor described herein, or a pharmaceutically acceptable salt thereof.

In some embodiments, disclosed herein is the use of Compound I, or a pharmaceutically acceptable salt or solvate thereof, in the treatment or prevention of fibrosis or a fibrotic disease or condition in mammal. In some cases, the disease or condition is associated with desmoplasia. Fibrosis can include abnormal accumulation of fibrous tissue that can occur, e.g., as a part of the wound-healing process in damaged tissue, which can result, for example, from physical injury, inflammation, infection, exposure to toxins, and other causes. Examples of fibrosis include dermal scar formation, keloids, liver fibrosis, lung fibrosis, kidney fibrosis, glomerular sclerosis, tubulointerstitial fibrosis and scleroderma.

In one aspect, provided herein are methods of using Compound I, or a pharmaceutically acceptable salt or solvate thereof, for the prevention and/or treatment of a condition, disease or disorder associated with LOXL2 activity. In some embodiments, the methods disclosed herein comprise the administration of Compound I, or a pharmaceutically acceptable salt or solvate thereof, to a subject having a disease, condition or disorder described herein. In some embodiments, the methods disclosed herein comprise the administration of Compound I, or a pharmaceutically acceptable salt or solvate thereof, to a subject suspected of having or developing a disease, condition or disorder described herein.

In one aspect, provided herein are methods for the treatment or prevention of one or more signs, symptoms or complications in a subject resulting from a disease, condition or disorder described herein, the methods comprising administration of Compound I, or a pharmaceutically acceptable salt or solvate thereof, to the subject.

In one aspect, provided herein are methods for the prevention of a condition, disease or disorder associated with LOXL2 activity, the methods comprising administering Compound I, or a pharmaceutically acceptable salt or solvate thereof, in combination with another preventative therapy.

In one aspect, provided herein are methods for the treatment of a condition, disease or disorder associated with LOXL2 activity, the methods comprising administering Compound I, or a pharmaceutically acceptable salt or solvate thereof, in combination with another treatment.

In one aspect, provided herein are methods for the attenuation, reversal and/or inhibition of a sign, symptom or complication of a condition, disease or disorder associated with LOXL2 activity, the methods comprising administering Compound I, or a pharmaceutically acceptable salt or solvate thereof.

In one aspect, provided herein are methods for the attenuation, reversal and/or cessation of a sign, symptom or complication of a condition, disease or disorder associated with LOXL2 activity, the methods comprising administering Compound I, or a pharmaceutically acceptable salt or solvate thereof, in combination with one or more additional therapies.

In some embodiments, the administration of Compound I, or a pharmaceutically acceptable salt or solvate thereof, or the administration of a pharmaceutical composition comprising Compound I, or a pharmaceutically acceptable salt or solvate thereof, described herein, comprises the administration of Compound I, or a pharmaceutically acceptable salt or solvate thereof, at a therapeutically effective dose. In some embodiments, a therapeutically effective dose is between about 0.01 mg to 5000 mg. For example, a therapeutic dose is between about 1 mg and about 5000 mg, between about 50 mg and about 4000 mg, between about 50 mg and about 4000 mg, between about 150 mg and about 4000 mg, between about 250 mg and about 2000 mg, between about 50 mg and about 1000 mg, or any integer between the aforementioned values. In some embodiments, a therapeutically effective dose is administered continuously. In some implementations, a therapeutically effective dose is administered 4 times a day, 3 times a day, 2 times a day, once a day, 6 times a week, 5 times a week, 4 times a week, 3 times a week, twice per week, once per week, or less often. In some embodiments, Compound I, or a pharmaceutically acceptable salt or solvate thereof, is administered for a therapeutically effective amount of time in any of the methods described herein. In some instances, a therapeutically effective amount of time is the time it takes to decrease or eliminate one or more signs or symptoms of a disease, condition or disorder described herein. For example, a therapeutically effective amount of time is between 1 day and 1 year. The aforementioned therapeutic dosage examples are not limiting. Additional therapeutic regimens are further described elsewhere herein.

Lung Fibrosis

Idiopathic pulmonary fibrosis (IPF) is a specific form of chronic, progressive, fibrosing interstitial pneumonia of unknown cause that is limited to the lungs. Well over one hundred different forms of interstitial lung disease (ILD) have been described. These diffuse infiltrative lung disorders are typically characterized by the presence of inflammation and altered lung interstitium. The histopathologic changes in the lungs of patients with ILD can range from granulomatous inflammation without parenchymal fibrosis in patients with sarcoidosis to extensive pulmonary fibrosis with architectural distortion of the lung in patients with idiopathic pulmonary fibrosis (IPF). Some forms of ILD have been linked to specific genetic abnormalities (e.g. Hermansky-Pudlak syndrome, familial pulmonary fibrosis), and a number of gene variants have been associated with an increased risk to develop ILD disorders such as IPF, sarcoidosis, or chronic beryllium disease (CBD).

Interstitial lung disease can also complicate connective tissue disorders (CTD), and lung histopathologic changes can have features of usual interstitial pneumonia (UIP) or non-specific interstitial pneumonia (NSIP) patterns in CTD-associated ILD.

In some embodiments, interstitial lung disease (ILD) includes, but is not limited to, idiopathic interstitial pneumonia, scleroderma-associated ILD, connective tissue disease-associated interstitial lung disease (CTD-ILD), sarcoidosis, hypersensitivity pneumonitis, iatrogenic pneumonitis/fibrosis (drug-induced ILD, radiation injury), eosinophilic ILD (e.g. eosinophilic pneumonia), occupational lung disease, inherited disorders (e.g. familial pulmonary fibrosis, Hermansky-Pudlak syndrome), and primary disorders (e.g. pulmonary Langerhans cell histiocytosis). In some embodiments, idiopathic interstitial pneumonia includes, but is not limited to, Idiopathic pulmonary fibrosis (IPF), Non-specific interstitial pneumonia (NSIP), Cryptogenic organizing pneumonia (COP), Respiratory bronchiolitis interstitial lung disease (RBILD), Desquamative interstitial pneumonia (DIP), acute interstitial pneumonia (AIP), lymphoid interstitial pneumonia (LIP)

Idiopathic pulmonary fibrosis (IPF) is a progressive and ultimately fatal disease of the lungs involving airway epithelial cell damage, fibroblast activation and proliferation, and excessive deposition of collagen and other extracellular matrix (ECM) components. These modifications of ECM composition and organisation alter the biomechanical properties of the lung parenchyma and increase local tension, which is critical in IPF disease pathogenesis.

One important driver of matrix tension is lysyl oxidase-like 2 (LOXL2), an enzyme that catalyses covalent cross-linking of ECM molecules, including fibrillar collagens. LOXL2 protein expression is observed in the fibroblastic foci and collagenous regions of diseased IPF lung tissue, with relatively minor expression in healthy lung tissue (Barry-Hamilton et al. *Nat Med* 2010; 16: 1009-1017). LOXL2 has also been localised to the active disease interface in liver fibrosis, and is considered a core driver in fibrosis (Mehal et al., Nat Med 2011; 17: 552-553). LOXL2 is associated with areas of active fibrogenesis in diseased tissues.

IPF is a specific form of chronic, progressive, fibrosing interstitial pneumonia of unknown cause, occurring primarily in older adults, limited to the lungs, and associated with the histopathologic and/or radiologic pattern of UIP. It is a disease characterized clinically by progressive worsening of dyspnea and lung function and pathologically by the formation of scar tissue within the lungs in the absence of any known provocation. Patients usually present with symptoms of IPF between the ages of 40 and 70 years with the median age for presentation being 66 years.

IPF is characterized by decline in lung function over time. The most prominent symptoms of IPF are exercise-induced dyspnea and chronic dry cough, which interfere with daily activities of the patients. Aside from restrictive defects on pulmonary function, other frequent clinical features of IPF include bibasilar inspiratory crackles and hypoxemia induced clubbing. Retrospective studies suggest that symptoms precede the IPF diagnosis by a duration of 6 months to 2 years. The onset of symptoms is slow, but over a period of months to years, symptoms worsen and lung function slowly declines, leading to hypoxia and eventually death from respiratory failure. There are 3 potential clinical courses for IPF: a) slow physiologic deterioration with worsening severity of dyspnea, which is the most common; b) rapid deterioration and progression to death; or c) periods of relative stability interposed with periods of acute respiratory decline sometimes manifested by hospitalizations for respiratory failure. The median survival time of IPF is estimated to be between 2 and 5 years from the time of diagnosis.

Although IPF is considered a disorder of unknown etiology by definition, a number of potential risk factors have been identified. Cigarette smoking is strongly associated with IPF. In addition, various other environmental and occupational exposures to metal dusts, wood dust, farming, hairdressing, stone cutting/polishing, livestock, and vegetable dust/animal dust have been linked with increased risk for developing IPF.

Usual interstitial pneumonia is the histologic/radiological pattern associated with IPF. The histologic pattern of UIP consists of normal lung alternating with patches of dense fibrosis.

Hamman-Rich syndrome is also known as acute interstitial pneumonia, or AIP, and has a rapid clinical course (days to weeks), a high mortality rate, and a distinctive histopathological appearance on biopsy; the dominant histopathological feature is diffuse alveolar damage (DAD). The median age of AIP in published cases is 50 years. Use of immunosuppressive treatment is often undertaken in the management of patients with AIP/DAD, usually in the form of high dose intravenous corticosteroids. In contrast, immunosuppressive therapy is known to be ineffective as maintenance therapy in IPF.

ILD may be diagnosed in patients under age 18 years, known as interstitial lung disease in children (chILD). Immunocompetent children with ILD are typically treated with some type of immunosuppressive therapy, most commonly corticosteroids. Fibrosis is thought to occur as a consequence of persistent inflammation. In general, chILD can be divided into 2 main categories: diseases that manifest soon after birth and those that develop after 2 years of age. The diseases manifesting after age 2 years tend to be treated with antiinflammatory therapy, most notably corticosteroids. In contrast, the diseases under age 2 years tend to be airspace-filling diseases with associated interstitial fibrosis (ie, not similar to ILD in adults) and tend to have a poor prognosis relative to older children with chILD. Patients with chILD who are under the age of 2 years include a subset of infants with mutations of ATP-binding cassette transporter A3 (ABCA3) and surfactant protein C. While many surfactant mutations lead to death from acute neonatal respiratory failure, some patients with less severe mutations develop chronic interstitial lung disease that is refractory to standard therapy.

In some embodiments, described herein is a method of treating lung fibrosis in a mammal comprising administering a selective LOXL2 inhibitor to the mammal in need thereof. In some embodiments, the selective LOXL2 inhibitor is Compound I, or a pharmaceutically acceptable salt or solvate thereof. In some embodiments, the selective LOXL2 inhibitor is Compound I, hydrochloride salt. In some embodiments, the selective LOXL2 inhibitor is Compound I, mesylate salt.

In some embodiments, Compound I, or a pharmaceutically acceptable salt or solvate thereof, is used in the treatment of prevention of a disease or condition associated with lung fibrosis. Fibrosis of the lung includes many syndromes and diseases. Exemplary diseases include idiopathic pulmonary fibrosis (IPF), idiopathic interstitial pneumonia, and acute respiratory distress syndrome (ARDS). Lung fibrosis also includes, but is not limited to, cryptogenic fibrosing alveolitis, chronic fibrosing interstitial pneumonia, interstitial lung disease (ILD), and diffuse parenchymal lung disease (DPLD).

In some embodiments, Compound I, or a pharmaceutically acceptable salt or solvate thereof, is used in the treatment of prevention of lung fibrosis.

The pathogenesis of most lung fibroses, including the aforementioned diseases, are not well understood, however all are characterized by an influx of inflammatory cells and a subsequent increase in the synthesis and deposition of collagen-rich extracellular matrix.

IPF is characterized by inflammation, and eventually fibrosis, of lung tissue; although these two symptoms can also be dissociated. The cause of IPF is unknown; it may arise either from an autoimmune disorder or as a result of infection. Symptoms of IPF include dyspnea (i.e., shortness of breath) which becomes the major symptom as the disease progresses, and dry cough. Death can result from hypoxemia, right-heart failure, heart attack, lung embolism, stroke or lung infection, all of which can be brought on by the disease.

In some embodiments, Compound I, or a pharmaceutically acceptable salt or solvate thereof, is used in the treatment of prevention of a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

Among humans with IPF, higher serum LOXL2 (sLOXL2) levels are associated with increased risk for IPF disease progression (Chien et al. *Eur Respir J* 2014; 43: 1430-1438). In some embodiments, sLOXL2 levels are predictive of an IPF patient's response to targeted therapy with a selective LOXL2 inhibitor (e.g. Compound I, or a pharmaceutically acceptable salt or solvate thereof). Patients with high baseline LOXL2 levels are at increased risk for poor IPF outcomes. In some embodiments, Compound I, or a pharmaceutically acceptable salt or solvate thereof, is used to treat a fibrotic disease or condition in a human that have a sLOXL2 level that is at least 2 times, at least 4 times, at least 6 times, at least 8 times, at least 10 times, at least 20 times, at least 50 times, or at least 100 times greater than the sLOXL2 level of a human without a fibrotic disease or condition. In some embodiments, the fibrotic disease or condition is lung fibrosis. In some embodiments, the fibrotic disease or condition is IPF.

In some embodiments, the severity of idiopathic pulmonary fibrosis is assessed by evaluating symptoms, pulmonary function tests, exercise capacity, lung structure using CT scans and the use of the St. George's Respiratory Questionnaire (SGRQ).

Pulmonary Function Tests (PFTs) are an important tool in assessing IPF severity. The easiest test to perform is spirometry and involves a maximal expiration through a mouthpiece followed by a maximal inspiration. The result is the Forced Vital Capacity (FVC). This is the amount of air that is exhaled starting from a maximal inhalation. Results are compared to age, gender and race matched normals. Results are displayed as a volume of air as well as a percent predicted. Normal is about 80% predicted or greater. There are no single agreed upon cut-offs for staging IPF by FVC but many clinicians use the following: mild IPF is about >75% predicted FVC, moderate IPF is about 50-75% predicted FVC, severe IPF is about 25-49% predicted FVC, and very severe IPF is about <25% predicted FVC. More important than the specific value of the FVC is the change in FVC over time. A decline in FVC of >5-10% is associated with an increased risk of death.

In some embodiments, administration of Compound I, or a pharmaceutically acceptable salt or solvate thereof, to a human with lung fibrosis increases the FVC of the human. In some embodiments, Compound I, or a pharmaceutically acceptable salt or solvate thereof, increases the FVC of a human with lung fibrosis by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more than 100%.

Diffusion capacity is another type of pulmonary function test. It is a measure of the way in which gas exchanges across the lungs. The results are reported as percent predicted. Lower values indicate more advanced disease. Values less than 40% are associated with worse survival. Declines in diffusing capacity are also associated with worse outcomes. Diffusing capacity of the lungs for carbon monoxide (DLCO) determines how much oxygen travels from the alveoli of the lungs to the blood stream.

In some embodiments, administration of Compound I, or a pharmaceutically acceptable salt or solvate thereof, to a human with lung fibrosis increases the DLCO. In some embodiments, Compound I, or a pharmaceutically acceptable salt or solvate thereof, increases the DLCO of a human with lung fibrosis by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or more than 100%.

The six-minute walk test measures exercise capacity (distance walked, oxygen saturation during exercise and heart rate and blood pressure).

High resolution CT scanning provides an assessment of the structural extent of fibrosis—how much fibrosis is present. More advanced radiographic fibrosis is associated with worse outcomes. Over time, increased extent of fibrosis is also associated with less good outcomes.

Other factors associated with a worse prognosis include advanced age, gender, heavy prior smoking history, being underweight, development of pulmonary hypertension and exacerbations of your underlying disease. IPF patients are also at increased risk for developing lung cancer, which has a powerful impact on prognosis.

The St. George's Respiratory Questionnaire (SGRQ) is an index designed to measure and quantify health-related health status in patients with chronic airflow limitation. It has been shown to correlate well with established measures of symptom level, disease activity and disability (Jones et al., The St. George's Respiratory Questionnaire. *Resp Med* 1991; 85 (suppl B):2531; Jones et al., A self-complete measure of health status for chronic airflow limitation. *Am Rev Respir Dis* 1992; 145; 1321-1327; Barr et al., American translation, modification, and validation of the St. George's Respiratory Questionnaire. Clin Ther. 2000 September, 22(9):1121-45).

The SGRQ is self-administered. The first part of the SGRQ ("Symptoms") evaluates symptomatology, including frequency of cough, sputum production, wheeze, breathlessness and the duration and frequency of attacks of breathlessness or wheeze. Evaluation is repeated with a 1, 3 or 12-month recall. The second part has two components: "Activity" and "Impacts." The "Activity" section addresses activities that cause breathlessness or are limited because of breathlessness. The "Impacts" section covers a range of factors including influence on employment, being in control of health, panic, stigmatization, the need for medication, side effects of prescribed therapies, expectations for health and disturbances of daily life.

Scores range from 0 to 100, with higher scores indicating more limitations. Based on empirical data and interviews with patients, a mean change score of 4 units is associated with slightly efficacious treatment, 8 units for moderately efficacious change and 12 units for very efficacious treatment (Jones P W., *Eur Respir J* 1994, 7:55-62; Jones P W. *Eur Respir J.* 2002 March, 19(3):398-404).

In some embodiments, administration of Compound I, or a pharmaceutically acceptable salt or solvate thereof, to a human with lung fibrosis results in a reduction in the SGRQ score. In some embodiments, the SGRQ score decreases by at least 1 unit, at least 2 units, at least 3 unit, at least 4 units, at least 5 unit, at least 6 units, at least 7 unit, at least 8 units, at least 9 unit, at least 10 units, at least 11 unit, at least 12 units, or more than 12 units.

In some embodiments, Compound I, or a pharmaceutically acceptable salt or solvate thereof, is used to slow the decline in lung function in a human with lung fibrosis. In some embodiments, Compound I, or a pharmaceutically acceptable salt or solvate thereof, is used to reduce the frequency of disease exacerbations in a human with lung fibrosis. In some embodiments, Compound I, or a pharmaceutically acceptable salt or solvate thereof, is used to improve survival in a human with lung fibrosis. In some embodiments, Compound I, or a pharmaceutically acceptable salt or solvate thereof, is used to slow the decline in lung function, reduce the frequency of exacerbations, and improve survival in a human with lung fibrosis.

As the normal lung is replaced by scar tissue, the lung's ability to exchange gas and deliver oxygen into the blood is impaired. If enough of the lung is involved, this can result in low oxygen levels in the blood. This is referred to as hypoxemia or hypoxia. Blood oxygen levels are measured in two ways.

Noninvasive oxygen measurements are made with a pulse oximeter. The pulse oximeter reads a saturation that measures the percentage of hemoglobin that is carrying oxygen. Normal values are between 96-100%.

A more accurate way to measure the amount of oxygen in blood is with an arterial blood gas. This requires sticking a needle into the artery in your wrist and removing a few milliliters of blood. The oxygen tension is then directly measured.

In some embodiments, oxygen is administered to the human when saturations are less than 88-89% either at rest, with activity or when sleeping. Resting oxygen saturations are generally higher than exercise oxygen saturations. Sleeping oxygen saturations are usually in between.

Oxygen is delivered from tanks or concentrators via nasal cannula. Usual flow rates start at 2 liters per minute but may be increased as needed. Advanced delivery systems such as oximizer pendants can improve oxygen delivery for patients that require high flow rates.

In some embodiments, gastro-esophageal reflux disease (GERD) plays a role in the development progression of IPF. In some embodiments, acid suppressing therapy is coadministered with Compound I, or a pharmaceutically acceptable salt or solvate thereof. Acid suppressing therapy includes, but is not limited to, H2 Blockers (e.g. cimetidine, famotidine, lafutidine, nizatidine, ranitidine, roxatidine, tiotidine) and proton pump inhibitors (e.g. omeprazole).

In some embodiments, a vaccination against pneumonia is coadministered with Compound I, or a pharmaceutically acceptable salt or solvate thereof. Suitable vaccines include, but are not limited to, polysaccharide vaccines and conjugated vaccines. The polysaccharide vaccine most commonly used today (PneumoVax) consists of purified polysaccharides from 23 serotypes (1, 2, 3, 4, 5, 6b, 7F, 8, 9N, 9V, 10A, 11A, 12F, 14, 15B, 17F, 18C, 19F, 19A, 20, 22F, 23F, and 33F). Conjugated vaccines consist of capsular polysaccharides covalently bound to the diphtheria toxoid CRM197. An example of a conjugated vaccine is Prevnar 13. PneumoVax is given as 2 doses separated by at least 5 years and separated from Prevnar by at least one year. Prevnar is given as a one-time dose.

In some embodiments, pulmonary rehabilitation is performed in combination with the administered of Compound I, or a pharmaceutically acceptable salt or solvate thereof. Pulmonary rehabilitation is a structured exercise program that focuses on both aerobic and strength training.

In some embodiments, one or more cough suppression medications are coadministered with Compound I, or a pharmaceutically acceptable salt or solvate thereof. Cough can be one of the most vexing symptoms of IPF. Treatments for cough include, but are not limited to, expectorants, antitussives, or cough suppressants, antihistamines, decongestants, steroids, benzonatate, thalidomide, cannabinoids, honey and sugar syrups.

Expectorants include, but are not limited to, acetylcysteine and guaifenesin.

Antitussives, or cough suppressants, include, but are not limited to, codeine, pholcodine, dextromethorphan, noscapine, and butamirate.

Antihistamines include, but are not limited to, mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine.

Decongestants include, but are not limited to, ephedrine.

Steroids, include, but are not limited to, betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Cannabinoids include, but are not limited to, cannabis, marinol, dronabinol.

In some embodiments, honey or sugar syrups soften the coughing.

In yet another embodiment described herein, Compound I, or a pharmaceutically acceptable salt or solvate thereof, is coadministered with at least one agent used in the treatment of respiratory conditions. Agents used in the treatment of respiratory conditions include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine), mucolytics, corticosteroids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, pirfenidone, nintedanib, 5-lipoxygenase-activating protein (FLAP) inhibitors, FLAP modulators and 5-LO inhibitors.

In a specific embodiment described herein, Compound I, or a pharmaceutically acceptable salt or solvate thereof, is coadministered with at least one anti-inflammatory agent. In certain embodiments, Compound I, or a pharmaceutically acceptable salt or solvate thereof, is coadministered with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, BAY-x1005, MN-001, and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), AZ-4407 and ZD-2138 and compounds found in US 2007/0149579, WO2007/016784.

In one aspect, Compound I, or a pharmaceutically acceptable salt or solvate thereof, is coadministered with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, Compound I, or a pharmaceutically acceptable salt or solvate thereof, is coadministered with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, Compound I, or a pharmaceutically acceptable salt or solvate thereof, is coadministered with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, Compound I, or a pharmaceutically acceptable salt or solvate thereof, is coadministered with inhaled corticosteroids.

In some embodiments, an immunosuppresant is coadministered with Compound I, or a pharmaceutically acceptable salt or solvate thereof. Immunosuppresants include, but are not limited to, prednisone and azathioprine.

In some embodiments, low doses of prednisone are coadministered with Compound I, or a pharmaceutically acceptable salt or solvate thereof.

In some embodiments, N-acetyl cysteine (NAC) is coadministered with Compound I, or a pharmaceutically acceptable salt or solvate thereof.

In some embodiments, Compound I, or a pharmaceutically acceptable salt or solvate thereof, is used in combination with another therapeutic agent that is useful in the treatment of lung fibrosis, such as IPF. In some embodiments, therapeutic agents that are useful in the treatment of lung fibrosis, such as IPF, include agents that slow down the decline in lung function over time. Therapeutic agents that slow down the decline in lung function over time, include, but are not limited to, pirfenidone and nintedanib. Additional therapeutic agents are contemplated, such as imatinab and other tyrosine kinase inhibitors, PBI-4050, recombinant pentraxin-2/SAP (PRM-151), aerosol IFN-γ, inhibitors of CTGF activity (FG-3019), LPA receptor antagonists (BMS-986020, SAR100842), autotaxin inhibitors (GLPG-1690, PAT-409), galectin-3 inhibitors (TD 139), Tipelukast (MN-001), integrin antagonists (STX-100/BG00011, GSK3008348), PI3K inhibitors (GSK2126458), JNK inhibitors (CC-90001), ROCK inhibitors (KD025), anti-IL-13 compounds (Tralokinumab, Lebrikizumab, QAX-576), CCL2 antagonists (CNTO888), CCR2 antagonists (Cenicriviroc), anti-CD20 compounds (Rituximab), anticoagulants (Dabigatran), collagen V treatments (IW001) and ASK1 inhibitors (GS4997).

In some embodiments, Compound I, or a pharmaceutically acceptable salt or solvate thereof, is used in combination with pirfenidone. In some embodiments, pirfenidone is coadminstered with Compound I, or a pharmaceutically acceptable salt or solvate thereof, up to a maximum daily dose of 2,403 mg.

In some embodiments, Compound I, or a pharmaceutically acceptable salt or solvate thereof, is used in combination with nintedanib. In some embodiments, nintedanib is coadminstered with Compound I, or a pharmaceutically acceptable salt or solvate thereof, up to a maximum daily dose of 300 mg.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

In some embodiments, Compound I, or a pharmaceutically acceptable salt or solvate thereof, is administered to an adult human with lung fibrosis. In some embodiments, the lung fibrosis is IPF. In some embodiments, the adult human is >18 years of age, >20 years of age, >25 years of age, >30 years of age, >35 years of age, >40 years of age, >45 years of age, >50 years of age, >55 years of age, >60 years of age, >65 years of age, >70 years of age, >75 years of age, >80 years of age, or >85 years of age. In some embodiments, the adult human is 30 to 85 years of age, 35 to 85 years of age, 40 to 85 years of age, 45 to 85 years of age, or 40 to 80 years of age.

Idiopathic pulmonary fibrosis affects more adult men than women. In some embodiments, Compound I, or a pharmaceutically acceptable salt or solvate thereof, is administered to an adult male human with lung fibrosis.

In some embodiments, Compound I, or a pharmaceutically acceptable salt or solvate thereof, is administered to human child with ILD. A human child is ≤18 years of age. Chronic ILD in children ages 0 to 2 shows a different array of conditions compared with children ages 2 to 18. Genetic and developmental disorders affecting the airways are more likely in children ages 0 to 2 years. After 2 years of age, chILD diseases tend to somewhat resemble IPF in adults (ie, are more fibrotic). There is also a subset of infants with recessive ABCA3 mutations that cause childhood interstitial lung disease.

In some embodiments, Compound I, or a pharmaceutically acceptable salt or solvate thereof, is administered to an human child with ILD, wherein the human child is ≤18 years of age, 0 to <2 years of age, or ≥2 to ≤18 years of age.

Pulmonary Alveolar Proteinosis (PAP)

In some embodiments, disclosed herein is the use of Compound I, or a pharmaceutically acceptable salt or solvate thereof, in the treatment or prevention of pulmonary alveolar proteinosis (PAP). Pulmonary alveolar proteinosis (PAP) is a lung disease in which abnormal accumulation of pulmonary surfactant phospholipids and protein components occurs within the alveoli, interfering with gas exchange. PAP can occur in a primary form or secondarily in the settings of malignancy (especially in myeloid leukemia), pulmonary infection, or environmental exposure to dusts or chemicals. Rare familial forms have also been recognized, suggesting a genetic component in some cases.

In some embodiments, LOXL2 is expressed in PAP tissue, but not normal lung tissue. In some embodiments, LOXL2 contributes to development of PAP.

Two forms of PAP are recognized, (1) primary (idiopathic) and (2) secondary (due to lung infections; hematologic malignancies; and inhalation of mineral dusts such as silica, titanium oxide, aluminum, and insecticides). Incidence of PAP is increased in patients with hematologic malignancies and AIDS, suggesting a relationship with immune dysfunction.

The alveoli in PAP are filled with proteinaceous material, which has been analyzed extensively and determined to be normal surfactant composed of lipids and surfactant-associated proteins A, B, C, and D (SP-A, SP-C, SP-D). Evidence exists of a defect in the homeostatic mechanism of either the production of surfactant or the clearance by alveolar macrophages and the mucociliary elevator. A clear relationship has been demonstrated between PAP and impaired macrophage maturation.

Incidence for males is 4 times higher than for females. Patients are typically 20-50 years old at presentation.

Patients with PAP typically present with a gradual onset of symptoms, including, but not limited to, persistent dry cough (or scant sputum production), progressive dyspnea, fatigue and malaise, weight loss, intermittent low-grade fever and/or night sweats, pleuritic chest pain, cyanosis, and hemoptysis.

The etiology of PAP is unknown. Causes may include inhalation of silica dust (acute silicoproteinosis), exposure to insecticides, aluminum dust, titanium dioxide, and other inorganic dusts, hematologic malignancies, myeloid disorders, lysinuric protein intolerance, HIV infection (AIDS), leflunomide-case report and disease-modifying antirheumatoid arthritis therapy. Differentials may include hypersensitivity pneumonitis, lung cancer, non-small cell lung cancer, oat cell lung cancer (Small Cell), *Pneumocystis carinii* pneumonia, pulmonary edema and cardiogenic sarcoidosis.

No specific therapy exists for PAP. Sequential whole lung lavage is the standard of care. Management of PAP depends on the progression of the illness, coexisting infections, and degree of physiological impairment. The standard of care for PAP is mechanical removal of the lipoproteinaceous material by whole-lung lavage, which is often repeated. Historically, patients have been treated with systemic steroids, mucolytics (aerosol), and proteinase (aerosol) without much success. In secondary PAP, appropriate treatment of the underlying cause also is warranted. Congenital PAP responds favorably to lung transplantation.

Lung transplantation is the treatment of choice in patients with congenital PAP and in adult patients with end-stage interstitial fibrosis. The major complications are lung infections with *N. asteroides, Pneumocystis carinii*, and/or *Mycobacterium avium-intracellulare*. Pulmonary fibrosis also can complicate PAP.

Liver Disease

Lysyl oxidase-like 2 (LOXL2) is expressed in fibrotic human liver tissue, where it carries out cross-linking of collagen and other matrix components, resulting in increased stiffness, activation of pathologic fibroblasts and a dynamic process of matrix remodeling and fibrogenesis. LOXL2 is expressed in fibrotic liver tissue from human diseases of diverse etiology, including hepatitis C infection, non-alcoholic steatohepatitis (NASH), alcoholic steatohepatitis (ASH), Wilson's disease, and primary biliary cirrhosis, in addition to mouse models of sclerosing cholangitis.

Chronic liver diseases affect the liver tissue in various ways, such as fibrosis and steatosis.

Any chronic attack on the liver will cause inflammation, which then leads to the formation of fibrous scar tissue in the liver, creating hepatic fibrosis. This fibrosis is therefore a scarring process that will replace damaged liver cells. The extent of this fibrosis can vary, and it is described in several stages. A normal liver is at a stage between F0 and F1. Stage F2 denotes light fibrosis, and F3 is severe fibrosis. "Cirrhosis" is defined from stage F4, when scar tissue exists throughout the liver.

Fibrosis disorganises the architecture of the liver both anatomically and functionally. When fibrosis reaches the cirrhosis stage, it is initially completely asymptomatic; this is the compensated cirrhosis stage, i.e. not complicated. The cirrhosis then decompensates, and liver complications appear. Liver complications include, but are not limited to, portal hypertension which is secondary to liver fibrosis (this impedes venous circulation and causes the pressure in the portal vein to rise), ascites (which is the formation of a liquid effusion in the abdominal cavity, which can become infected), icterus (jaundice), hepatic encephalopathye (which corresponds to neurological disorders by the accumulation of toxins that are not broken down by the liver), primitive cancer of the liver (which is a final complication, and can also be called hepatocellular carcinoma).

The degree of fibrosis constitutes an important prognostic parameter. Extent of the fibrosis is one factor affecting the diagnosis and decisions concerning therapy, and a criterion for tracking the progress of the illness and the effectiveness of therapy.

Liver steatosis is an accumulation of fat in the liver, making a "fatty liver." It corresponds to the accumulation of lipids (triglycerides) in the liver cells (hepatocytes) and may complicate alcoholic intoxication or metabolic disorders such as Type 2 diabetes, obesity, and dyslipdemia. Such steatosis can either be isolated, making it a pure steatosis, or associated with hepatitis, which makes it non-alcoholic steatohepatitis (NASH). Steatosis and NASH form non-alcoholic fatty liver disease (NAFLD). These are usually asymptomatic conditions, but they are currently becoming more common because of the increasing number of overweight patients.

In some cases, steatosis can develop into a fibrosis that can lead to cirrhosis.

In some embodiments, disclosed herein is the use of Compound I, or a pharmaceutically acceptable salt or solvate thereof, in the treatment or prevention of a liver disease or condition. In some embodiment, such as a fibrotic liver disease or condition or liver (hepatic) fibrosis, for example, any hepatic fibrosis, regardless of underlying liver disease. Liver fibrosis and liver diseases associated with fibrosis include, but are not limited to, hepatitis C virus (HCV), nonalcoholic steatohepatitis (NASH), primary sclerosing cholangitis (PSC), cirrhosis, liver fibrosis, and portal hypertension, and can also include primary biliary cirrhosis (PBC), autoimmune hepatitis, alcoholic cirrhosis, alpha 1 antitrypsin deficiency disease, hereditary hemochromatosis, Wilson's disease, hepatitis B virus (HBV), and HIV associated steatohepatitis and cirrhosis, and associated conditions such as chronic viral hepatitis, non-alcoholic fatty liver disease (NAFLD), alcoholic steatohepatitis (ASH), nonalcoholic steatohepatitis (NASH), primary biliary cirrhosis (PBC), biliary cirrhosis, primary sclerosing cholangitis, and autoimmune hepatitis. In certain embodiments, the disease or condition is non-alcoholic steatohepatitis (NASH), primary biliary cirrhosis (PBC), or primary sclerosing cholangitis (PSC). In some embodiments, the disease or condition is a viral hepatitic disease or condition that is acute or chronic. Among the exemplary diseases and conditions are hepatitis C virus (HCV), hepatitis B virus (HBV), with or without HCV infection- or HBV infection-associated liver damage. Thus, among the provided methods are methods for antifibrotic therapy in patients with liver disease, such as viral hepatitis. In some aspects, the liver disease is compensated liver disease. On other aspects, it is decompensated liver disease, such as liver disease associated with ascites, esophageal varices, encephalopathy, and/or jaundice.

Liver (hepatic) fibrosis is implicated in the pathology of numerous hepatic diseases and can occur as can occur as a part of the wound-healing response to chronic liver injury, as a complication of haemochromatosis, Wilson's disease, alcoholism, schistosomiasis, viral hepatitis, bile duct obstruction, exposure to toxins, and metabolic disorders. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death. Chronic insults to the liver from sources including parasites and viral infection (e.g. hepatitis B virus (HBV), HCV, human immunodeficiency virus (HIV), schistosomiasis) or the long term stress from alcohol consumption typically result in remodeling of the liver, presumably to encapsulate the damaged area and protect the remaining liver tissue from damage. (Li and Friedman, *Gastroenterol. Hepatol.* 14:618-633, 1999). Liver fibrosis results in extracellular matrix changes, including 3-10 fold increases in total collagen content and replacement of the low density basement membrane with high-density matrix, which impair the metabolic and synthesis function of hepatocytes, hepatic stellate cells and endothelial cells. Hepatic stellate cell (HSC) activation is the central event leading to hepatic fibrosis. Activation of HSC implies two steps: initiation ("preinflammatory stage") and perpetuation which involves also several changes: proliferation, chemotaxis, fibrogenesis, contractility, matrix degradation, retinoid loss, WBC chemoatractants and cytokine release (Girogescu, M., Non-invasive Biochemical Markers of Liver Fibrosis, *J. Gastrointestin. Liver Dis.*, 15(2): 149-159 (2006)).

Gradual accumulation of collagen in the hepatic parenchyma is a final common pathway of chronic liver disease. This progressive accumulation of fibrosis can ultimately lead to cirrhosis of liver and end-stage liver disease. LOXL2 expression is increased in diseased liver tissue.

During liver injury, HSCs undergo transformation from a retinoid rich pericyte-like cell to a myofibroblast-like cell, a process termed activation. Highly activated HSCs are morphologically indistinguishable from myofibroblasts.

The activated HSCs express collagen I and other extracellular matrix genes and are quantitatively the major source of the matrix which accumulates during fibrosis. During activation, HSC enter the cell cycle with the result that the hepatic matrix accumulation is the result of an overall increase in the number of HSCs in addition to changes in HSC gene expression.

Recovery from liver fibrosis is associated with remodelling of the excess liver matrix resulting in restitution of near normal liver architecture. An element of this recovery process is apoptosis of activated HSCs.

Therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation using (e.g., gamma interferon or antioxidants), promotion of matrix degradation, or promotion of stellate cell apoptosis. Treatments are needed that address the underlying biochemical process as opposed to merely suppressing inflammation. Embodiments of the provided methods address this need.

In some embodiments, a regimen for the treatment of liver fibrosis with Compound I, or a pharmaceutically acceptable salt or solvate thereof, includes removal of the underlying cause of fibrosis (if known), suppression of inflammation, down-regulation of stellate cell activation, promotion of matrix degradation, promotion of stellate cell apoptosis, or combinations thereof.

A number of standardized scoring systems exist which provide a quantitative assessment of the degree and severity of liver fibrosis. These include the METAVIR, Knodell, Scheuer, Ludwig, and Ishak scoring systems. Individuals with liver fibrosis include individuals with any degree or severity of liver fibrosis, based on any of the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0—no fibrosis; score: 1—stellate enlargement of portal tract but without septa formation; score: 2—enlargement of portal tract with rare septa formation; score: 3—numerous septa without cirrhosis; and score: 4—cirrhosis.

Knodell's scoring system, also called the Histology Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. In some embodiments, scoring includes analyzing overall Knodell neuroinflammatory index, and/or individual components thereof, such as Knodell inflammation score and/or necrosis score.

In the Scheuer scoring system scores are as follows: score: 0—no fibrosis; score: 1—enlarged, fibrotic portal tracts; score: 2—periportal or portal-portal septa, but intact architecture; score: 3—fibrosis with architectural distortion, but no obvious cirrhosis; score: 4—probable or definite cirrhosis.

In the Ishak scoring system, Stage 0—No fibrosis; Stage 1—Fibrous expansion of some portal areas, with or without short fibrous septa; stage 2—Fibrous expansion of most portal areas, with or without short fibrous septa; stage 3—Fibrous expansion of most portal areas with occasional portal to portal (P-P) bridging; stage 4—Fibrous expansion of portal areas with marked bridging (P-P) as well as portal-central (P-C); stage 5—Marked bridging (P-P and/or P-C) with occasional nodules (incomplete cirrhosis); stage 6—Cirrhosis, probable or definite.

In some aspects, the liver disease or fibrosis is assessed by determining the Model for End-stage Liver Disease (MELD) score. In some aspects, the methods predict or determine that or the likelihood that the individual has or has at least a particular MELD score.

In some aspects, the liver disease is compensated or decompensated liver disease. For example, decompensated liver disease may be associated with ascites, esophageal varices, encephalopathy, and/or jaundice.

In some embodiments, disclosed herein is the use of Compound I, or a pharmaceutically acceptable salt or solvate thereof, in the treatment of liver fibrosis. In some embodiments, disclosed herein is the use of Compound I, or a pharmaceutically acceptable salt or solvate thereof, in the treatment of liver fibrosis in humans with NASH. In some embodiments, disclosed herein is the use of Compound I, or a pharmaceutically acceptable salt or solvate thereof, in the treatment of liver fibrosis in humans with PSC.

In some embodiments, disclosed herein is the use of Compound I, or a pharmaceutically acceptable salt or solvate thereof, in the treatment of liver fibrosis secondary to NASH in humans. In some embodiments, disclosed herein is the use of Compound I, or a pharmaceutically acceptable salt or solvate thereof, in the treatment of advanced liver fibrosis but not cirrhosis secondary to NASH in humans. In some embodiments, treatment includes, increase in the event free survival (EFS). EFS is the time to progression to cirrhosis. In some embodiments, the adults with liver fibrosis have chronic liver disease due to NASH and a Stage 3-4 fibrosis by Ishak score on a liver biopsy. In some embodiments, the adults with advanced liver fibrosis have chronic liver disease due to NASH and a Stage 3-4 fibrosis by Ishak score on a liver biopsy.

In some embodiments, disclosed herein is the use of Compound I, or a pharmaceutically acceptable salt or solvate thereof, in the prevention of progression of liver fibrosis. In some embodiments, disclosed herein is the use of Compound I, or a pharmaceutically acceptable salt or solvate thereof, in the prevention of progression of liver fibrosis in subjects with primary sclerosing cholangitis (PSC). In some embodiments, the subjects are adult subjects (aged ≥18) with chronic cholestatic liver disease.

In some embodiments, disclosed herein is the use of Compound I, or a pharmaceutically acceptable salt or solvate thereof, in the treatment of cirrhosis due to NASH.

In some embodiments, disclosed herein is the use of Compound I, or a pharmaceutically acceptable salt or solvate thereof, in the treatment of compensated cirrhosis due to NASH.

In some embodiments, treatment includes, reversal of cirrhosis due to NASH, regression of fibrosis, decrease in hepatic venous pressure gradient (HVPG), and/or increase in the event free survival (EFS). EFS is the time to first liver-related event or death. Liver-related events include any of the following: liver transplantation, qualification for liver transplantation (MELD≥15), events indicative of hepatic decompensation, esophageal variceal bleeding, ascites, hepatic encephalopathy, newly diagnosed varices in a subject without prior varices.

In some embodiments, disclosed herein is the use of Compound I, or a pharmaceutically acceptable salt or solvate thereof, in the treatment of liver fibrosis in humans infected with a virus. In some embodiments, the virus is human immunodeficiency virus (HIV), or Hepatitis C (HCV), or a HIV/HCV co-infection.

In some embodiments, disclosed herein is the use of Compound I, or a pharmaceutically acceptable salt or solvate thereof, in the treatment of NASH.

In a model of liver fibrosis, treatment with Compound I, or a pharmaceutically acceptable salt or solvate thereof, significantly reduced fibrosis as assessed by the area fraction of Picrosirius red (collagen) positive staining, while rAB0023 showed only a trend for reduction.

In some embodiments, disclosed herein is the use of Compound I, or a pharmaceutically acceptable salt or solvate thereof, in combination with a second therapeutic agent for the treatment of liver disease in a mammal. In some embodiments, disclosed herein is the use of Compound I, or a pharmaceutically acceptable salt or solvate thereof, in combination with a second therapeutic agent for the treatment of liver disease in a mammal, wherein the second therapeutic agent is selected from the group consisting of PPAR agonists, Incretins, Glut2-1, FXR agonists, antioxidants, GLP-1 modulators, SGLT-2 inhibitors, Bile acids, Caspase protease inhibitors, ACC inhibitors, Synthetic fatty acid/bile acid conjugates, dual CCR2/CC5 antagonists, Immunomodulators, Sirtuin stimulants, Fatty acid inhibitor, DGAT1 inhibitors, CD3 antigens, PDE-4 modulators, AMPK stimulants, ROCK2 inhibitors, ASBT inhibitors, ASK1 inhibitors, JNK inhibitors, TLR-4 antagonists, THR beta agonists, Cathepsin B inhibitors, Galectin-3 modulators, anti-miR-21 compounds and combinations thereof.

In some embodiments, disclosed herein is the use of Compound I, or a pharmaceutically acceptable salt or solvate thereof, in combination with a second therapeutic agent for the treatment of liver disease in a mammal, wherein the second therapeutic agent is selected from PPAR agonists (e.g., Saroglitazar, Pioglitazone GFT 505), Incretins, Glut2-I, FXR agonists (e.g. fexaramine, PX 102, PX 104 Obeticholic acid (OCA), chenodeoxycholic acid (CDCA), GW4064, WAY-362450 (FXR-450 or XL335)), antioxidants (e.g., cysteine depleting agents, Vitamin E, RP103, Mitoquinone), GLP-1 modulators (e.g., liraglutide), SGLT-2 inhibitors (e.g., rernogliflozin etabonate) Bile acids (e.g., Ursodeoxycholic acid), Caspase protease inhibitors (e.g., Emricasan icosapent ethyl ester), acetyl-CoA carboxylase inhibitor ACC inhibitors (e.g. NDI-010976), Synthetic fatty acid/bile acid conjugates (e.g., Ararrichol), dual CCR2/CC5 antagonists (e.g., Cenicriviroc), Immunomodulators (e.g., IMM 124E), Sirtuin stimulants (e.g., MB 12065), Fatty acid inhibitors (e.g., Oltipraz), DGAT1 inhibitors (e.g., Pradigastat), CD3 antigens (e.g., TRX 318), PDE-4 modulators (e.g., Roflurnilast), AMPK activator (e.g., MB 11055), ROCK2 inhibitors (e.g., KD 025), ASBT inhibitors (e.g., SHP 626), ASK1 inhibitors (e.g., GS-4997), TLR-4 antagonists (e.g., JKB-121), THR beta agonists (e.g., MGL-3195), Cathepsin B inhibitors (e.g., SHP 626, VBγ-376), Galectin-3 modulators (e.g. GR MD 02, LGPC-1010), NC 101, DUR-928, DWP-10292, anti-miR-21 compounds (RG-012), and combinations thereof.

In some embodiments, disclosed herein is the use of Compound I, or a pharmaceutically acceptable salt or solvate thereof, in combination with a second therapeutic agent for the treatment of liver disease in a mammal, wherein the second therapeutic agent is a PPAR (α,γ) agonist or PPAR (α,δ) agonist.

Kidney Fibrosis

In some embodiments, the disease or condition is or is associated with kidney fibrosis. Like liver fibrosis, kidney fibrosis can result from various diseases and insults to the kidneys. Examples of such diseases and insults include chronic kidney disease, metabolic syndrome, vesicoureteral reflux, tubulointerstitial renal fibrosis, IgA nephropathy, diabetes (including diabetic nephropathy), Alport syndrome, HIV associated nephropathy, resultant glomerular nephritis (GN), including, but not limited to, focal segmental glomerulosclerosis and membranous glomerulonephritis, mesangiocapillary GN and resultant interstitial fibrosis and tubular atrophy (IFTA), including but not limited to, recovery post acute kidney injury (AKI), acute obstructive nephropathy and drug induced fibrosis.

It has become recognized that metabolic syndrome is a cluster of abnormalities including diabetic hallmarks such as insulin resistance, as well as central or visceral obesity and hypertension. In nearly all cases, dysregulation of glucose results in the stimulation of cytokine release and upregulation of extracellular matrix deposition. Additional factors contributing to chronic kidney disease, diabetes, metabolic syndrome, and glomerular nephritis include hyperlipidemia, hypertension, hyperglycemia, and proteinuria, all of which result in further damage to the kidneys and further stimulate the extracellular matrix deposition. Thus, regardless of the primary cause, insults to the kidneys may result in kidney fibrosis and the concomitant loss of kidney function. (Schena, F. and Gesualdo, L., Pathogenic Mechanisms of Diabetic Nephropathy, J. Am. Soc. Nephrol., 16: S30-33 (2005); Whaley-Connell, A., and Sower, J. R., Chronic Kidney Disease and the Cardiometabolic Syndrome, J. Clin. Hypert., 8(8): 546-48 (2006)).

In some embodiments, disclosed herein is the use of Compound I, or a pharmaceutically acceptable salt or solvate thereof, in combination with a second therapeutic agent for the treatment of kidney disease in a mammal, wherein the second therapeutic agent is selected from anti-hypertensive agents, including, but not limited to, angiotensin receptor blockers (ARBs), angiotensin converting enzyme (ACE) inhibitors and calcium channel blockers, sodium-glucose co-transporter-2 (SGLT2) inhibitors/gliflozins (e.g. empagliflozin or canagliflozin), diuretic agents (thiazide diuretic), or novel therapies under investigation in diabetic kidney disease such as PKC inhibitors (e.g Ruboxistaurin), endothelin receptor antagonists (atrasentan), allopurinols (xanthine oxidase), steroid mineralocorticoide receptor antagonists (e.g. finerenone), anti-AGE therpeies (e.g. PYR-311), Janus kinase inhibitors (e.g. baricitinib), DPP-4 inhibitors (gliptins such as saxagliptin, vildagliptin, linagliptin or sitagliptin), GLP1-receptor antagonists (e.g. liraglutide or dulaglutide), anti-inflammatory agents such as pentoxyfylline. In some embodiments, the mammal is on dialysis. In some embodiments, the mammal is not on dialysis.

Figure 6A:
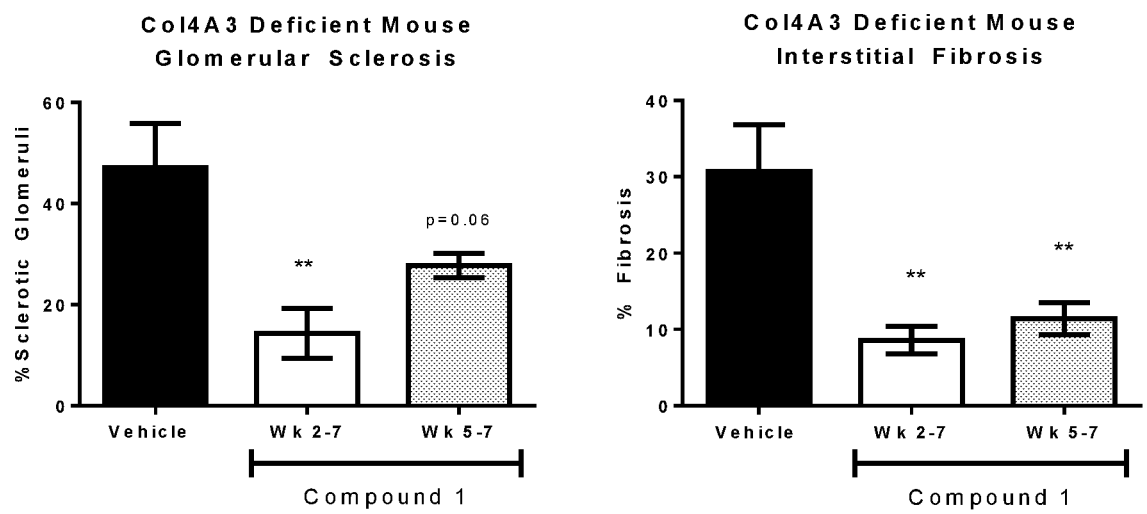
FIG. 6a shows glomerular sclerosis (left) and interstitial fibrosis (right) scores reflecting kidney fibrosis in the Col4A3 deficient mouse model of Alport syndrome and chronic kidney disease. Samples were harvested at 7 weeks of age after oral administration of Compound 1 at 30 mg/kg QD starting at 2 weeks or 5 weeks of age (**$p<0.01$).

As shown in the FIG. 6a, lysyl oxidase like-2 contributes to Alport renal disease progression. In this renal fibrosis model, treatment with Compound 1 significantly reduced both tubulointerstitial fibrosis as well as glomerulosclerosis. In some embodiments, Compound I, or a pharmaceutically acceptable salt or solvate thereof, is used in the treatment of kidney disease. In some embodiments, the kidney disease is kidney fibrosis. In some embodiments, the kidney disease is Alport renal disease. In some embodiments, the kidney disease is chronic kidney disease.

Myelofibrosis

In some embodiments, the disease or condition is or is associated with myelofibrosis. Pathogenic processes in primary myelofibrosis involve a primary megakaryocyte-weighted clonal myeloproliferation and a paraneoplastic stromal reaction that includes bone marrow fibrosis, osteosclerosis, angiogenesis, and extramedullary hematopoiesis. The bone marrow reaction includes excess deposition of extracellular matrix proteins such as fibrillar collagen, hypocellularity, activation and recruitment of bone marrow fibroblasts, excessive cytokine and growth factor production, and other changes that result in a reduction of hematopoietic capacity. Secondary myelofibrosis can result from polycythemia rubra vera or essential thrombocytosis.

In some embodiments, disclosed herein is the use of Compound I, or a pharmaceutically acceptable salt or solvate thereof, in the treatment of myelofibrosis.

In some embodiments, disclosed herein is the use of Compound I, or a pharmaceutically acceptable salt or solvate thereof, in the treatment of primary, post polycythemia vera or post essential thrombocythemia myelofibrosis. In some embodiments, treatment includes reduction in bone marrow fibrosis score, clinical improvement, partial remission, or complete remission.

In some embodiments, Compound I, or a pharmaceutically acceptable salt or solvate thereof, is used either alone or in combination with ruxolitinib.

Scleroderma

Figure 9:
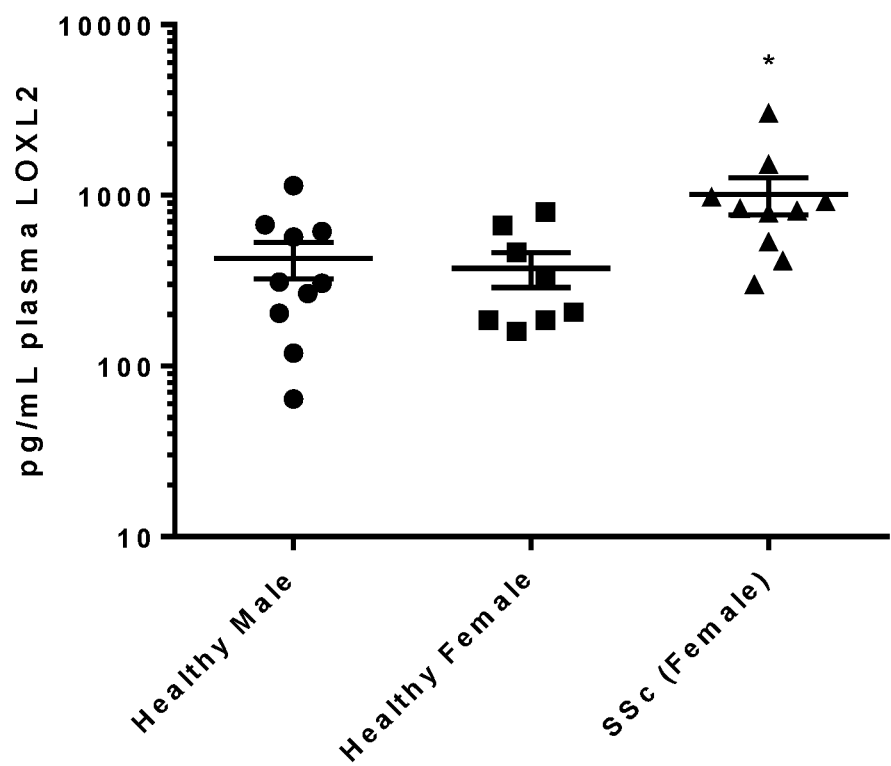
FIG. 9 shows concentrations of plasma LOXL2 measured in healthy male and female subjects and Scleroderma patients (n=10 each) measured using a biotin-tagged LOXL2 inhibitor and a proprietary Erenna®-based assay (*p=0.04 upaired t-test of SSc (female) vs. Healthy (female).

Scleroderma or systemic sclerosis is a potentially fatal autoimmune disease of unknown etiology, characterized by progressive multi-organ fibrosis that is largely refractory to currently available pharmacological therapies. Systemic sclerosis is thought to be initiated by tissue injury, in response to which dysregulated wound-healing processes are thought to contribute to the development of fibrosis. Scleroderma patients have increased plasma LOXL2 concentrations compared to healthy subjects (FIG. 9).

In some embodiments, disclosed herein is the use of Compound I, or a pharmaceutically acceptable salt or solvate thereof, in the treatment of scleroderma. There are two major forms of scleroderma: limited systemic sclerosis (also known as morphea or cutaneous scleroderma) and diffuse systemic sclerosis. In some embodiments, Compound I, or a pharmaceutically acceptable salt or solvate thereof, is used to treat limited systemic sclerosis. In some embodiments, Compound I, or a pharmaceutically acceptable salt or solvate thereof, is used to treat diffuse systemic sclerosis.

In some cases scleroderma runs in families. Thus, in some embodiments, Compound I, or a pharmaceutically acceptable salt or solvate thereof, is administered prophylactically to asymptomatic members of a family wherein at least one member of the family has been diagnosed with scleroderma.

In some embodiments, scleroderma is a manifestation of another disease or condition. In such individuals who are diagnosed with the other disease or condition, Compound I, or a pharmaceutically acceptable salt or solvate thereof, is administered prophylactically to prevent the onset of scleroderma.

As used herein, "limited systemic scleroderma" means a disorder characterized by the thickening and hardening of the skin and subcutaneous tissues from excessive collagen deposition. It is often accompanied by the following: calcinosis, Raynaud's phenomenon, esophageal dysfunction, sclerodactyly, and telangiectasias. Additionally, an individual suffering from limited systemic sclerosis may present with pulmonary arterial hypertension.

As used herein, "diffuse systemic scleroderma" means a disorder of the skin and internal organs characterized by the thickening and hardening of the skin and subcutaneous tissues from excessive collagen deposition. In certain instances, diffuse systemic scleroderma is accompanied by Raynaud's phenomenon and calcinosis.

In some embodiments, Compound I, or a pharmaceutically acceptable salt or solvate thereof, is used in the treatment or prevention of any one of the following in a mammal: localized cutaneous scleroderma, localized morphea, morphea-lichen sclerosus et atrophicus overlap, generalized morphea, atrophoderma of Pasini and Pierini, pansclerotic morphea, morphea profunda, linear scleroderma, systemic scleroderma, CREST syndrome, sclerodactyly, systemic sclerosis, progressive systemic sclerosis.

In some embodiments, Compound I, or a pharmaceutically acceptable salt or solvate thereof, is administered to treat or prevent Dupuytren's disease. Dupuytren's disease is a disease wherein the tissues under the skin on the palm of the hand thicken and shorten so that the tendons connected to the fingers cannot move freely. Dupuytren's disease results from abnormal fibrosis of the palmar fascia.

In some embodiments, Compound I, or a pharmaceutically acceptable salt or solvate thereof, is administered to a mammal to treat or prevent capsular contracture. Capsular contracture is an abnormal response of the immune system to foreign materials. When breast implants, or any other foreign object, such as artificial joint prosthetics, are placed in the body, the body forms a lining around it. Capsular contracture is characterized by the formation of capsules of collagen fibers around a foreign body. In certain instances, capsular contracture results from an abnormal immune response to breast implants and artificial joint prosthetics. In some embodiments, Compound I, or a pharmaceutically acceptable salt or solvate thereof, is administered before, during, or concurrently with breast augmentation. In some embodiments, Compound I, or a pharmaceutically acceptable salt or solvate thereof, is administered before, during, or concurrently with the implantation of an artificial joint.

In some embodiments, Compound I, or a pharmaceutically acceptable salt or solvate thereof, is administered to treat cutaneous radiation syndrome. As used herein, "cutaneous radiation syndrome" means the pathophysiological reactions of the skin and skin appendages to significant levels of ionizing radiation. In certain instances, an individual with cutaneous radiation syndrome presents with abnormal skin fibrosis. In some embodiments, a formulation disclosed herein is used to treat cutaneous radiation syndrome, wherein an individual in need thereof present with undesired/abnormal skin fibrosis.

In some embodiments, Compound I, or a pharmaceutically acceptable salt or solvate thereof, is administered to a mammal to treat scarring. As used herein, scarring refers to the formation of a scar. In one aspect, the scar is a hypertrophic scar, or keloid scar, or a scar resulting from acne. In certain instances, a scar is an area of fibrous tissue that results from the overproduction of collagen. In certain instances, wound healing comprises the migration of fibroblasts to the site of injury. In certain instances, fibroblasts deposit collagen. In certain instances, fibroblasts deposit excess collagen at the wound site, resulting in a scar.

In some embodiments, scarring results from a trauma (e.g., surgery). In some embodiments, a formulation disclosed herein is administered before, after, or concurrently with a surgery.

In some embodiments, the scarring results from a burn. In some embodiments, a formulation disclosed herein is administered while an individual is being treated for a burn.

In some embodiments, a formulation disclosed herein is administered before, after, or concurrently with a scar revision procedure.

Ocular Fibrosis

In healthy ocular tissues, lysyl oxidase activity is present in the vitreous, iris, ciliary body, lens, choroid, retinal pigment epithelium, and retina. A majority of blinding ocular diseases are associated with a disruption of the tissue architecture in the eye, caused by vascular leakage and fibrosis (Friedlander M. Fibrosis and diseases of the eye. *J Clin Invest.* 2007; 117:576-586). Progressive fibrosis is not only associated with the pathogenesis of glaucoma, but can also be a consequence of surgical treatment to lower the IOP. Surgical failure is indeed characterized by an excessive postoperative wound healing response with subsequent scarring.

Targeting LOXL2 with an inhibitory monoclonal antibody reduced pathological angiogenesis, inflammation, and fibrosis in a rabbit model of glaucoma surgery. (Van Bergen T, Marshall D, Van de Veire S, et al. The role of LOX and LOXL2 in scar formation after glaucoma surgery. *Invest Ophthalmol Vis Sci.* 2013; 54:5788-5796). As well, targeting LOXL2 reduced angiogenesis and inflammation, in addition to fibrosis, in a CNV-related AMD animal model (Van Bergen et al. The role of LOX and LOXL2 in the pathogenesis of an experimental model of choroidal neovascularization. *Invest Ophthalmol Vis Sci.* 2015; 56:5280-5289).

In some embodiments, LOXL2 contributes to a wound healing response in ocular tissues.

In some instances, corneal scarring is caused by injury to the cornea (abrasion, laceration, burns, or disease). Surface abrasions heal transparently and do not leave scars. Deeper abrasions and ulcerations/lacerations result in a loss of corneal tissue, which is replaced by scar tissue. Proliferation of new blood vessels in the clear cornea assists in the healing process. Aberrant wound healing results in loss of vision.

In some embodiments, Compound I, or a pharmaceutically acceptable salt or solvate thereof, is administered to a mammal to reduce or inhibit the proliferation of fibroblasts and/or increases apoptosis of fibroblasts associated with fibrotic disorders, inflammation and/or proliferative disorders of the eye. In some embodiments, Compound I, or a pharmaceutically acceptable salt or solvate thereof, reduces, ameliorates or inhibits fibrosis and/or aberrant wound healing in ocular tissues.

In another aspect, Compound I, or a pharmaceutically acceptable salt or solvate thereof, is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In yet another aspect, Compound I, or a pharmaceutically acceptable salt or solvate thereof, is used to reduce, ameliorate, or inhibit aberrant wound healing and/or scarring of ocular tissues (e.g., the cornea or retina). In some instances, scarring is the result of disease e.g., keratitis (e.g., inflammation caused by herpes simplex, or syphilis). In some instances, surgical procedures including, for example, corneal graft, corneal transplant, trabeculectomy and/or radiation assisted eye surgery induce corneal scarring. In certain instances, corneal injury is due to laser assisted in situ keratomileusis (LASIK). In some instances, corneal scarring is due to corneal ulcers. In certain instances, proliferative membranes of the posterior segment of the eye induce the deposition of mutilating fibrous tissue and consequent production of scar tissue. In some instances, retinal thinning and scarring is due to structural changes in the retina caused by chronic cystoid macular edema (chronic CME). In certain instances, disorganized growth of retinal blood vessels in prematurely born babies results in scarring and/or retinal detachment (retinopathy of prematurity (ROP)) In some instances, bleeding, leaking and scarring from abnormal blood vessel growth (choroidal neovascularization) due to wet age related macular degeneration (wet AMD) causes irreversible damage to photoreceptors and rapid vision loss if left untreated.

Examples of disorders associated with aberrant wound healing and/or scarring of ocular tissues that, in some embodiments, are treated with Compound I, or a pharmaceutically acceptable salt or solvate thereof, are episcleral fibrosis leading to bleb (trabeculectomy) failure after glaucoma filtration surgery, pterygia (including post-surgical wound healing/scarring), cataracts (post surgical scarring), corneal scarring, scarring associated with ocular cicatricial pemphigoid, glaucoma filtration surgery (trabeculectomy), fibrosis associated with a keratoprosthesis procedure, wet age related macular degeneration with neovascularization and foveal thickening, diabetic retinopathy with retinal edema (and neovascularization), proliferative vitreoretinopathy (PVR), prevention and treatment of macular thickening related to photocoagulation, retinopathy of prematurity (ROP), (primary) retinal detachment, chronic retinal macular edema, chronic cystoid macular edema, post-surgical macular edema, macular edema associated with inherited retinal disease.

Ear Fibrosis

In some embodiments, the disease or condition is or is associated with ear fibrosis. Like liver fibrosis, ear fibrosis can result from various diseases and insults to the ears. Fibrosis can occur in the middle ear as well as the inner ear. Inflammation in the middle ear can result in medial canal fibrosis and this is characterized by the formation of fibrotic tissue in the bony external auditory meatus (Ishii, Fluid and Fibrosis in the Human Middle Ear, *Am. J. Otolaryngol*, 1985: 6: 196-199). Fibrosis of the inner ear include disorders where strial dysfunction resulting from membrane thickening is observed. These diseases include Alport syndrome, lupus and diabetes. Type IV collagen disorders (as seen with Alport syndrome patients) is associated with sensorineural hearing loss with structural changes in the connective tissue and micromechanics of the inner ear. Detailed assessments of basement membrane morphology have been measured in the mouse model of Alport syndrome which shows clear thickening of the basement membrane of the stria vascularis (Cosgrove, Ultrastructural, physiological, and molecular defects in the inner ear of a gene-knockout mouse model for autosomal Alport syndrome. *Hear Res* 1998; 121:84-98.).

Cancer

LOXL2 has been shown to be involved in signaling related to cancer cell growth, adhesion, motility and invasion. Specifically, LOXL2 induces epithelial-to-mesenchymal transition (EMT) of cells to promote tumor invasion. LOXL2 is also upregulated in hypoxic tumor environments which leads to enhanced invasion of tumor cells. LOXL2 has also been shown to promote angiogenesis in hypoxic tumor environments.

Increased LOXL2 expression is associated with poor prognosis in patients with colon, esophageal tumors, oral squamous cell carcinomas, laryngeal squamous cell carcinomas, and head and neck squamous cell carcinomas. LOXL2 has been proposed to participate in cancers of the breast, colon, gastric, head and neck, lung, and melanoma.

In some embodiments, disclosed herein are methods of treating cancer with a compound disclosed herein.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In some embodiments, the disease or condition is or is associated with a cancer or tumor. Thus, in some embodiments, the subject is an oncology patient. Such diseases and conditions and cancers include carcinomas, sarcomas, benign tumors, primary tumors, tumor metastases, solid tumors, non-solid tumors, blood tumors, leukemias and lymphomas, and primary and metastatic tumors.

Carcinomas include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Solid tumors include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocyte leukemia, and hairy cell leukemia; and d) acute lymphoblastic leukemias (characterized by accumulation of lymphoblasts). Lymphomas include, but are not limited to, B-cell lymphomas (e.g., Burkitt's lymphoma); Hodgkin's lymphoma; and the like.

Benign tumors include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Primary and metastatic tumors include, e.g., lung cancer (including, but not limited to, lung adenocarcinoma, squamous cell carcinoma, large cell carcinoma, bronchioloalveolar carcinoma, non-small-cell carcinoma, small cell carcinoma, mesothelioma); breast cancer (including, but not limited to, ductal carcinoma, lobular carcinoma, inflammatory breast cancer, clear cell carcinoma, mucinous carcinoma); colorectal cancer (including, but not limited to, colon cancer, rectal cancer); anal cancer; pancreatic cancer (including, but not limited to, pancreatic adenocarcinoma, islet cell cancer, neuroendocrine tumors); prostate cancer; ovarian carcinoma (including, but not limited to, ovarian epithelial carcinoma or surface epithelial-stromal tumor including serous tumor, endometrioid tumor and mucinous cystadenocarcinoma, sex-cord-stromal tumor); liver and bile duct carcinoma (including, but not limited to, hepatocellular carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medulloblastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; and signet ring cell carcinoma.

In some embodiments, Compound I, or a pharmaceutically acceptable salt or solvate thereof, is administered to treat a dermal cancer. Dermal cancers include melanoma, squamous cell carcinoma and basal cell carcinoma.

In one aspect, Compound I, or a pharmaceutically acceptable salt or solvate thereof, reduces, ameliorates or inhibits cell proliferation and/or fibrosis associated with cancers.

In some embodiments, Compound I, or a pharmaceutically acceptable salt or solvate thereof, is administered to treat melanoma, cutaneous T cell lymphoma, mycosis fungoides, Merkel cell carcinomas, head and neck carcinomas, solar keratosis, squamous cell or basal cell cancer at any stage of the disease with or without metastases.

Rheumatoid Arthritis

Rheumatoid arthritis (RA) is a chronic autoimmune disorder in which the body's immune system attacks the joints and additional organs such as skin, eyes, lungs, and blood vessels. RA is a chronic inflammatory disease characterized by the synovial hyperplasia consisting of infiltrated immune cells and resident synovial fibroblasts (SF). Rheumatoid arthritis synovial fibroblasts (RASFs) are found in RA synovium and are key players in joint destruction and are able to migrate in vitro and in vivo. Various cytokines from infiltrated immune cells induce proliferation and activation of SF. Activated SF in turn generates pathogenic stroma to sustain chronic inflammation, leading to cartilage and bone destruction.

RASF differ from healthy synovial fibroblasts by their morphology and an aberrant gene expression pattern. RASF are characterized by the expression of antiapoptotic molecules, protooncogenes and a lack of expression of tumor suppressor genes. Owing to their ability to produce proinflammatory cytokines and chemokines, RASF further attract inflammatory cells of the immune system to the synovium. In addition, RASF produce enzymes such as matrix metalloproteinases (MMPs) that promote invasion into and destruction of cartilage.

LOXL2 is expressed and secreted in RASF and is upregulated by TNF-α and IL-1β. Knockdown of LOXL2 and antibodies against LOXL2 attenuated collagen deposition of RASF. Furthermore, LOXL2 knockdown reduced RASF proliferation and invasion. For example, the LOXL inhibitor β-aminopropionitrile (BAPN) ameliorated collagen induced arthritis (CIA) in an in vivo CIA mouse model (Tetsuya Saito, et al., Roles of collagen crosslinking enzyme, lysyl oxidase-like 2, in rheumatoid novial fibroblasts, Keystone Symposia on Molecular and Cellular Biology, Feb. 7-11, 2016, abstract Q3 3014).

LOXL2 is implicated in the activated phenotypes of RASF and represents a therapeutic target of RA. The aggressive, invasive phenotype of RASF appears early in RA as a consequence of stable cell activation. Several key factors in the pathogenesis of RA, including proinflammatory cytokines, innate immunity and matrix-degradation products, critically amplify activation of RASF.

In some embodiments, described herein is the use of a LOXL2 inhibitor (e.g. Compound I, or a pharmaceutically acceptable salt or solvate thereof) in the treatment of RA. In some embodiments, described herein is the use of a LOXL2 inhibitor (e.g. Compound I, or a pharmaceutically acceptable salt or solvate thereof) in the treatment of RA in combination with one or more additional agents used to treat RA.

Juvenile Idiopathic Arthritis

Juvenile idiopathic arthritis (JIA), also known as juvenile rheumatoid arthritis (JRA), is the most common form of arthritis in children and adolescents. Juvenile in this context refers to an onset before age 16. In some embodiments, described herein is the use of a LOXL2 inhibitor (e.g. Compound I, or a pharmaceutically acceptable salt or solvate thereof) in the treatment of JIA. In some embodiments, described herein is the use of a LOXL2 inhibitor (e.g. Compound I, or a pharmaceutically acceptable salt or solvate thereof) in the treatment of JIA in combination with one or more additional agents used to treat JIA.

Osteoarthritis

Osteoarthritis (OA) is a type of joint disease that results from breakdown of joint cartilage and underlying bone. LOXL2 has been shown to be highly expressed in the damaged region of OA cartilage (T. Sato et al., Arthritis & Rheumatism, Vol. 54, No. 3, pp 808-817 (2006)). In some embodiments, described herein is the use of a LOXL2 inhibitor (e.g. Compound I, or a pharmaceutically acceptable salt or solvate thereof) in the treatment of osteoarthritis. In some embodiments, described herein is the use of a LOXL2 inhibitor (e.g. Compound I, or a pharmaceutically acceptable salt or solvate thereof) in the treatment of osteoarthritis in combination with one or more additional agents used to treat osteoarthritis.

Psoriatic Arthritis

Psoriatic arthritis is a type of inflammatory arthritis that will develop in up to 30 percent of people who have psoriasis. Psoriatic arthritis is classified as a seronegative spondyloarthropathy and therefore occurs more commonly in patients with tissue type HLA-B27. In some embodiments, described herein is the use of a LOXL2 inhibitor in the treatment of psoriatic arthritis. In some embodiments, described herein is the use of a LOXL2 inhibitor (e.g. Compound I, or a pharmaceutically acceptable salt or solvate thereof) in the treatment of psoriatic arthritis in combination with one or more additional agents used to treat psoriatic arthritis.

Ankylosing Spondylitis

Ankylosing spondylitis (also known as Bekhterev's disease, Marie-Strümpell disease, or AS) is a chronic inflammatory disease of the axial skeleton. In some embodiments, described herein is the use of a LOXL2 inhibitor in the treatment of ankylosing spondylitis. In some embodiments, described herein is the use of a LOXL2 inhibitor (e.g. Compound I, or a pharmaceutically acceptable salt or solvate thereof) in the treatment of ankylosing spondylitis in combination with one or more additional agents used to treat ankylosing spondylitis.

(R,R)-trans-(3-((4-(Aminomethyl)-6-(trifluoromethyl)pyridin-2-yl)oxy)phenyl)(3-fluoro-4-hydroxypyrrolidin-1-yl)methanone (Compound I)

"Compound I" or "(R,R)-trans-(3-((4-(aminomethyl)-6-(trifluoromethyl)pyridin-2-yl)oxy)phenyl)(3-fluoro-4-hydroxypyrrolidin-1-yl)methanone" or "(3-((4-(aminomethyl)-6-(trifluoromethyl)-pyridin-2-yl)oxy)phenyl)(3R,4R)-3-fluoro-4-hydroxypyrrolidin-1-yl)methanone", or any other similar name refers to the compound with the following structure:

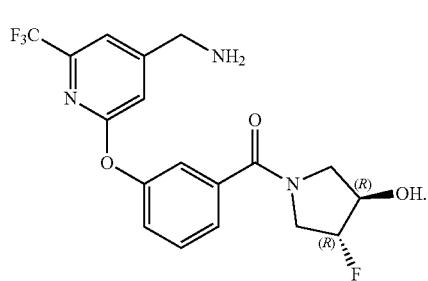

In some embodiments, Compound I is substantially free of the (S,S)-isomer (i.e. Compound I is substantially free of "(S,S)-trans-(3-((4-(aminomethyl)-6-(trifluoromethyl)pyridin-2-yl)oxy)phenyl)(3-fluoro-4-hydroxypyrrolidin-1-yl)methanone" or "(3-((4-(aminomethyl)-6-(trifluoromethyl)-pyridin-2-yl)oxy)phenyl)(3S,4S)-3-fluoro-4-hydroxypyrrolidin-1-yl)methanone", or any other similar name).

"Substantially free" with respect to an enantiomer, means that the referenced enantiomer is not present or there is less than 5%, less than 4%, less than 3%, less than 2% or less than 1% of the referenced enantiomer.

"Compound Ent-I" or "(S,S)-trans-(3-((4-(aminomethyl)-6-(trifluoromethyl)pyridin-2-yl)oxy)phenyl)(3-fluoro-4-hydroxypyrrolidin-1-yl)methanone" or "(3-((4-(aminomethyl)-6-(trifluoromethyl)-pyridin-2-yl)oxy)phenyl)(3S,4S)-3-fluoro-4-hydroxypyrrolidin-1-yl)methanone", or any other similar name refers to the compound with the following structure:

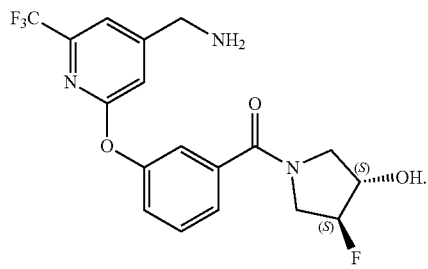

In some embodiments, racemic-trans-(3-((4-(aminomethyl)-6-(trifluoromethyl)pyridin-2-yl)oxy)phenyl)(3-fluoro-4-hydroxypyrrolidin-1-yl)methanone is used instead of Compound I. Racemic Compound I (Compound Rac-I) is depicted as follows:

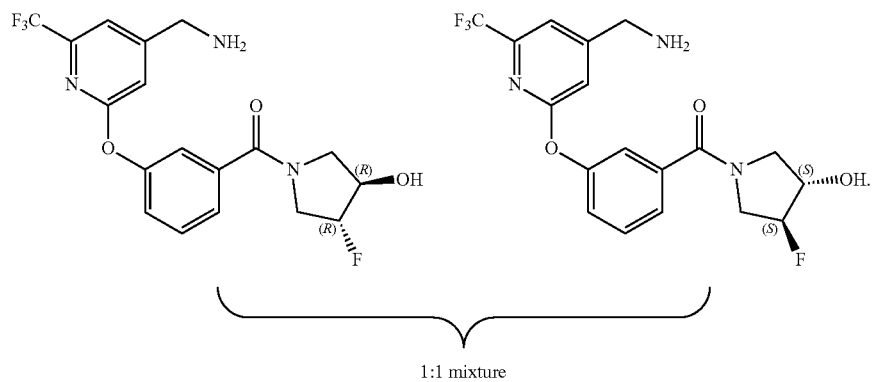

1:1 mixture

Compound I is a potent, mechanism-based LOXL2 inhibitor. Compound I is a high affinity, selective, irreversible, small-molecule inhibitor of LOXL2. In some embodiments, the aminomethyl pyridine moiety of Compound I interacts with the enzyme active site to form a time-dependent, pseudo-irreversible inhibitory complex. Profiling studies suggest that the two enantiomers of Compound I (i.e. (R,R) and (S,S)) are very similar to each other and to racemic Compound I in pharmacological and pharmacokinetic profile. Compound I was more potent than the (S,S)-isomer in in vitro assays. In some embodiments, Compound I was less than 2-fold more potent than the (S,S)-isomer in in vitro assays.

In some embodiments, Compound I specifically inhibits and/or binds to LOXL2. In some embodiments, Compound I does not substantially inhibit and/or bind to any other lysyl oxidase. Other lysyl oxidases include LOX, LOXL1, LOXL3, and LOXL4. In some embodiments, Compound I is specific for LOXL2. In some embodiments, Compound I inhibits the activity of LOXL2 and does not substantially inhibit the activity of LOX. In some embodiments, Compound I inhibits the activity of LOXL2 and does not substantially inhibit the activity of another lysyl oxidase-like protein.

As used herein, "selective LOXL2 inhibitor" refers to a small molecule inhibitor of LOXL2 that does not substantially inhibit and/or bind to any other lysyl oxidase. Other lysyl oxidases include LOX, LOXL1, LOXL3, and LOXL4. In some embodiments, a selective LOXL2 inhibitor does not substantially inhibit and/or bind to LOX or LOXL3. In some embodiments, a selective LOXL2 inhibitor is at least 2 times, at least 3 times, at least 4 times, at least 5 times, at least 10 times, at least 20 times, at least 30 times, at least 40 times, at least 50 times, at least 60 times, at least 70 times, at least 80 times, at least 90 times, at least 100 times, at least 120 times, at least 140 times, at least 160 times, at least 180 times, at least 200 times, at least 250 times, at least 300 times, at least 350 times, at least 400 times, at least 450 times, at least 500 times, at least 550 times, at least 600 times, at least 650 times, at least 700 times, at least 800 times, at least 900 times, or at least 1000 times more selective for LOXL2 than for LOX. In some embodiments, a selective LOXL2 inhibitor is at least 400 times more selective for LOXL2 than for LOX. In some embodiments, a selective LOXL2 inhibitor is at least 2 times, at least 3 times, at least 4 times, at least 5 times, at least 10 times, at least 20 times, at least 30 times, at least 40 times, at least 50 times, at least 60 times, at least 70 times, at least 80 times, at least 90 times, at least 100 times, at least 120 times, at least 140 times, at least 160 times, at least 180 times, at least 200 times, at least 250 times, at least 300 times, at least 350 times, at least 400 times, at least 450 times, at least 500 times, at least 550 times, at least 600 times, at least 650 times, at least 700 times, at least 800 times, at least 900 times, or at least 1000 times more selective for LOXL2 than for LOXL3. In some embodiments, a selective LOXL2 inhibitor is at least 5 times more selective for LOXL2 than for LOXL3.

In any of the embodiments disclosed herein (including methods, uses, formulations, combination therapy, etc.), Compound I, or a pharmaceutically acceptable salt or solvate thereof, is replaced with: a) Compound I, or a pharmaceutically acceptable salt or solvate thereof, of lower chiral purity; b) "(S,S)-trans-(3-((4-(aminomethyl)-6-(trifluoromethyl)pyridin-2-yl)oxy)phenyl)(3-fluoro-4-hydroxypyrrolidin-1-yl)methanone", or a pharmaceutically acceptable salt or solvate thereof of any optical purity; or c) racemic-trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof.

The term "pharmaceutically acceptable salt" in reference to Compound I refers to a salt of Compound I, which does not cause significant irritation to a mammal to which it is administered and does not substantially abrogate the biological activity and properties of the compound. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound I, or pharmaceutically acceptable salts thereof, are conveniently prepared or formed during the processes of preparing Compound I, or pharmaceutically acceptable salts thereof. In addition, Compound I, or pharmaceutically acceptable salts thereof, exist in unsolvated form. In some embodiments, Compound I, or a pharmaceutically acceptable salt thereof, is hydrated.

A wide variety of pharmaceutically acceptable salts are formed from Compound I and include:
  salts formed when Compound I (i.e. free base form) is treated with an inorganic acid. Inorganic acids include, but are not limited to, hydrochloric acid, hydrobromic acid, sulfuric acid, phosphoric acid, nitric acid, and metaphosphoric acid;
  salts formed when Compound I (i.e. free base form) is treated with an organic acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In any of the embodiments disclosed herein (including methods, uses, formulations, combination therapy, etc.), the hydrochloride salt of Compound I, or solvate thereof, is used. Compound I, hydrochloride salt (i.e. Compound 1), has the following structure:

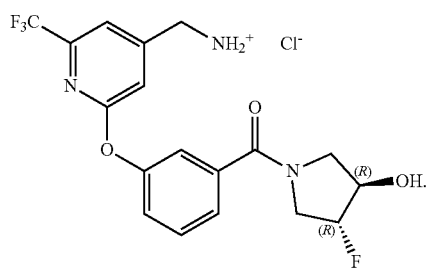

The (S,S)-enantiomer of Compound 1 (Compound Ent-1) has the following structure:

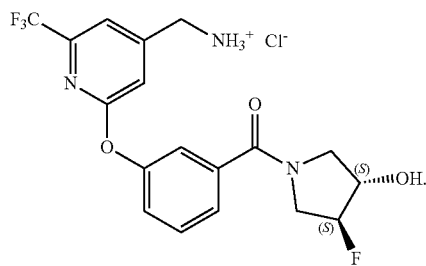

Racemic Compound 1 (Compound Rac-1) is depicted as follows:

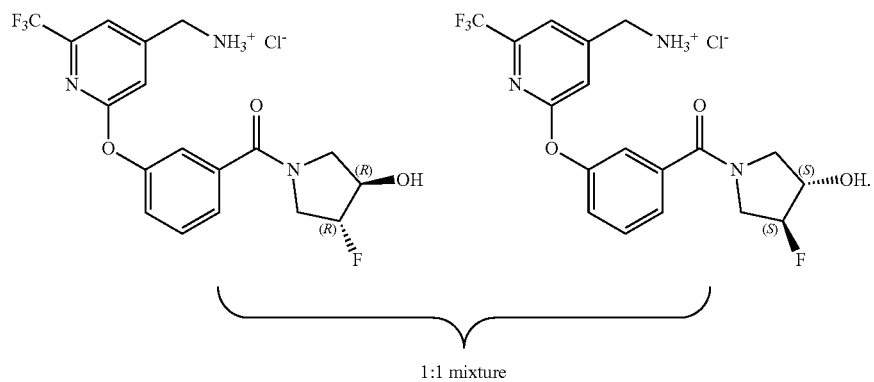

1:1 mixture

In any of the embodiments disclosed herein (including methods, uses, formulations, combination therapy, etc.), the methanesulfonic acid salt of Compound I, or solvate thereof, is used. Compound I methanesulfonate (Compound 2), or Compound I mesylate salt, or any other similar name, has the following structure:

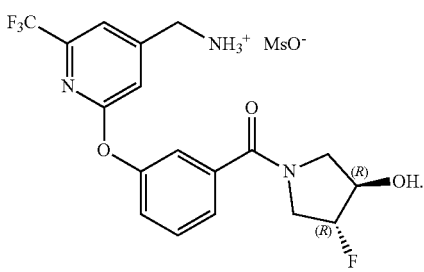

The (S,S)-enantiomer of Compound 2 (Compound Ent-2) has the following structure:

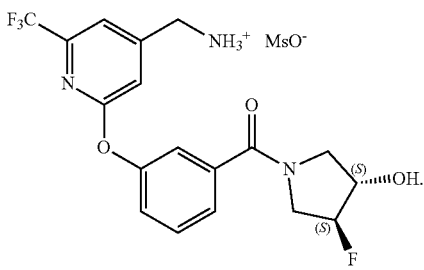

Racemic Compound 2 (Compound Rac-2) is depicted as follows:

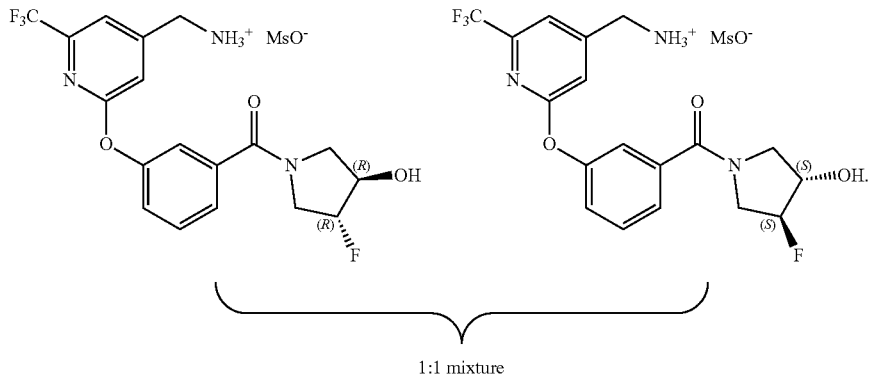

1:1 mixture

In some embodiments, Compound I described herein is prepared as a chloride salt, sulfate salt, bromide salt, mesylate salt, maleate salt, citrate salt or phosphate salt. In some embodiments, Compound I described herein is prepared as a hydrochloride salt. In some embodiments, a Compound I described herein is prepared as a mesylate salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

In any of the embodiments disclosed herein (including methods, uses, formulations, combination therapy, etc.), amorphous Compound I is used. In any of the embodiments disclosed herein (including methods, uses, formulations, combination therapy, etc.), crystalline Compound I is used. In any of the embodiments disclosed herein (including methods, uses, formulations, combination therapy, etc.), partially crystalline Compound I is used.

In some embodiments, in any of the embodiments disclosed herein (including methods, uses, formulations, combination therapy, etc.), Compound I, or a pharmaceutically acceptable salt thereof, is replaced with an active metabolite of Compound I, or a pharmaceutically acceptable salt thereof.

In some embodiments, in any of the embodiments disclosed herein (including methods, uses, formulations, combination therapy, etc.), Compound I, or a pharmaceutically acceptable salt thereof, is replaced with a prodrug of Compound I, or a pharmaceutically acceptable salt thereof.

In some embodiments, in any of the embodiments disclosed herein (including methods, uses, formulations, combination therapy, etc.), Compound I, or a pharmaceutically acceptable salt thereof, is replaced with a deuterated analog of Compound I, or a pharmaceutically acceptable salt thereof.

In some embodiments, Compound I is isotopically-labeled, where one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, Compound I is metabolized upon administration to a mammal to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, Compound I, or a pharmaceutically acceptable salt or solvate thereof, is used in the preparation of medicaments for the treatment of diseases or conditions in a mammal that would benefit from inhibition or reduction of LOXL2 activity. Methods for treating any of the diseases or conditions described herein in a mammal in need of such treatment, involves administration of pharmaceutical compositions that include Compound I, or a pharmaceutically acceptable salt or solvate thereof, active metabolite, prodrug, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing Compound I, or a pharmaceutically acceptable salt or solvate thereof, are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising Compound I, or a pharmaceutically acceptable salt or solvate thereof, in order to prevent a return of the symptoms of the disease or condition.

In certain embodiments wherein the patient's condition does not improve, upon the doctor's discretion the administration of Compound I, or a pharmaceutically acceptable salt or solvate thereof, is administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

In one aspect, Compound I, or a pharmaceutically acceptable salt or solvate thereof, is administered daily to humans in need of therapy with Compound I, or a pharmaceutically acceptable salt or solvate thereof. In some embodiments, Compound I, or a pharmaceutically acceptable salt or solvate thereof, is administered once-a-day. In some embodiments, Compound I, or a pharmaceutically acceptable salt or solvate thereof, is administered twice-a-day. In some embodiments, Compound I, or a pharmaceutically acceptable salt or solvate thereof, is administered three times-a-day. In some embodiments, Compound I, or a pharmaceutically acceptable salt or solvate thereof, is administered every other day. In some embodiments, Compound I, or a pharmaceutically acceptable salt or solvate thereof, is administered twice a week.

In general, doses of Compound I, or a pharmaceutically acceptable salt or solvate thereof, employed for treatment of the diseases or conditions described herein in humans are typically in the range of from about 0.1 mg to about 10 mg/kg of body weight per dose. In one embodiment, the desired dose is conveniently presented in a single dose or in divided doses administered simultaneously (or over a short period of time) or at appropriate intervals, for example as two, three, four or more sub-doses per day. In some embodiments, Compound I, or a pharmaceutically acceptable salt or solvate thereof, is conveniently presented in divided doses that are administered simultaneously (or over a short period of time) once a day. In some embodiments, Compound I, or a pharmaceutically acceptable salt or solvate thereof, is conveniently presented in divided doses that are administered in equal portions twice-a-day.

In some embodiments, Compound I, or a pharmaceutically acceptable salt or solvate thereof, is administered orally to the human at a dose from about 0.1 mg to about 10 mg/kg of body weigh per dose. In some embodiments, Compound I, or a pharmaceutically acceptable salt or solvate thereof, is administered to the human on a continuous daily dosing schedule.

The term "continuous dosing schedule" refers to the administration of a particular therapeutic agent at regular intervals. In some embodiments, continuous dosing schedule refers to the administration of a particular therapeutic agent at regular intervals without any drug holidays from the particular therapeutic agent. In some other embodiments, continuous dosing schedule refers to the administration of a particular therapeutic agent in cycles. In some other embodiments, continuous dosing schedule refers to the administration of a particular therapeutic agent in cycles of drug administration followed by a drug holiday (for example, a wash out period or other such period of time when the drug is not administered) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. In some embodiments, daily administration is once a day. In some embodiments, daily administration is twice a day. In some embodiments, daily administration is three times a day. In some embodiments, daily administration is more than three times a day.

The term "continuous daily dosing schedule" refers to the administration of a particular therapeutic agent everyday at roughly the same time each day. In some embodiments, daily administration is once a day. In some embodiments, daily administration is twice a day. In some embodiments, daily administration is three times a day. In some embodiments, daily administration is more than three times a day.

In some embodiments, the amount of Compound I, or a pharmaceutically acceptable salt or solvate thereof, is administered once-a-day. In some other embodiments, the amount of Compound I, or a pharmaceutically acceptable salt or solvate thereof, is administered twice-a-day. In some other embodiments, the amount of Compound I, or a pharmaceutically acceptable salt or solvate thereof, is administered three times a day.

In certain embodiments wherein improvement in the status of the disease or condition in the human is not observed, the daily dose of Compound I, or a pharmaceutically acceptable salt or solvate thereof, is increased. In some embodiments, a once-a-day dosing schedule is changed to a twice-a-day dosing schedule. In some embodiments, a three times a day dosing schedule is employed to increase the amount of Compound I, or a pharmaceutically acceptable salt or solvate thereof, that is administered. In some embodiments, the frequency of administration by inhalation is increased in order to provide repeat high Cmax levels on a more regular basis. In some embodiments, the frequency of administration is increased in order to provide maintained or more regular exposure to Compound I, or a pharmaceutically acceptable salt or solvate thereof. In some embodiments, the frequency of administration is increased in order to provide repeat high Cmax levels on a more regular basis and provide maintained or more regular exposure to Compound I, or a pharmaceutically acceptable salt or solvate thereof.

In any of the aforementioned aspects are further embodiments in which the effective amount of Compound I, or a pharmaceutically acceptable salt or solvate thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of Compound I, or a pharmaceutically acceptable salt or solvate thereof, including further embodiments in which (i) Compound I, or a pharmaceutically acceptable salt or solvate thereof, is administered once a day; or (ii) Compound I, or a pharmaceutically acceptable salt or solvate thereof, is administered to the mammal multiple times over the span of one day.

In any of the aforementioned aspects are further embodiments comprising multiple administrations of the effective amount of Compound I, or a pharmaceutically acceptable salt or solvate thereof, including further embodiments in which (i) Compound I, or a pharmaceutically acceptable salt or solvate thereof, is administered continuously or intermittently: as in a single dose; (ii) the time between multiple administrations is every 6 hours; (iii) Compound I, or a pharmaceutically acceptable salt or solvate thereof, is administered to the mammal every 8 hours; (iv) Compound I, or a pharmaceutically acceptable salt or solvate thereof, is administered to the mammal every 12 hours; (v) Compound I, or a pharmaceutically acceptable salt or solvate thereof, is administered to the mammal every 24 hours. In further or alternative embodiments, the method comprises a drug holiday, wherein the administration of Compound I, or a pharmaceutically acceptable salt or solvate thereof, is temporarily suspended or the dose of Compound I, or a pharmaceutically acceptable salt or solvate thereof, being administered is temporarily reduced; at the end of the drug holiday, dosing of Compound I, or a pharmaceutically acceptable salt or solvate thereof, is resumed. In one embodiment, the length of the drug holiday varies from 2 days to 1 year.

In general, doses employed for adult human treatment are typically in the range of 1 mg-5000 mg per day. In some embodiments, doses employed for adult human treatment are from about 1 mg to about 4000 mg per day, about 150 mg to about 4000 mg per day, about 50 mg to about 2000 mg per day, about 100 mg to about 2000 mg per day, or about 150 mg to about 2000 mg per day. In some embodiments, 50 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg of Compound I is administered to the adult human. In some embodiments, the desired dose is conveniently presented in a single dose or in divided doses administered simultaneously or at appropriate intervals, for example as two, three, four or more sub-doses per day.

In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the disease or condition to be treated, the mode of administration, the requirements of the individual subject, the severity of the disease or condition being treated, the identity (e.g., weight) of the human, and the particular additional therapeutic agents that are administered (if applicable), and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of Compound I, or a pharmaceutically acceptable salt or solvate thereof, lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, following the administration of a therapeutically effective dose of Compound I, or a pharmaceutically acceptable salt or solvate thereof, to a subject, the no observed adverse effect level (NOAEL) is at least 1, 10, 20, 50, 100, 500 or 1000 milligrams of Compound I, or a pharmaceutically acceptable salt or solvate thereof, per kilogram of body weight (mpk). In some examples, the 7-day NOAEL for a rat administered Compound I, or a pharmaceutically acceptable salt or solvate thereof, is at least about 200, 300, 400, 500, 600, 700, 800, 900, 1000, 1500 or 2000 mpk. In some examples, the 7-day NOAEL for a dog administered Compound I, or a pharmaceutically acceptable salt or solvate thereof, is at least about 10, 20, 30, 40, 50, 60, 70, 80, 90, 100, 200, 500 mpk.

Combination Treatments

In certain instances, it is appropriate to administer Compound I, or a pharmaceutically acceptable salt or solvate thereof, in combination with one or more other therapeutic agents.

In one embodiment, the therapeutic effectiveness of Compound I, or a pharmaceutically acceptable salt or solvate thereof, is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering Compound I, or a pharmaceutically acceptable salt or solvate thereof, with another agent (which also includes a therapeutic regimen) that also has therapeutic benefit.

In one specific embodiment, Compound I, or a pharmaceutically acceptable salt or solvate thereof, is co-administered with a second therapeutic agent, wherein Compound I, or a pharmaceutically acceptable salt or solvate thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of Compound I, or a pharmaceutically acceptable salt or solvate thereof, will be utilized in formulating pharmaceutical composition and/or in treatment regimens when Compound I, or a pharmaceutically acceptable salt or solvate thereof, is administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of Compound I, or a pharmaceutically acceptable salt or solvate thereof, is initiated prior to, during, or after treatment with a second agent described herein, and continues until any time during treatment with the second agent or after termination of treatment with the second agent. It also includes treatments in which Compound I, or a pharmaceutically acceptable salt or solvate thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, Compound I, or a pharmaceutically acceptable salt or solvate thereof, is administered either simultaneously with the one or more other therapeutic agents, or sequentially.

In combination therapies, the multiple therapeutic agents (one of which is Compound I, or a pharmaceutically acceptable salt or solvate thereof) are administered in any order or even simultaneously. If administration is simultaneous, the multiple therapeutic agents are, by way of example only, provided in a single, unified form, or in multiple forms (e.g., as a single pill or as two separate pills).

Compound I, or a pharmaceutically acceptable salt or solvate thereof, as well as combination therapies, are administered before, during or after the occurrence of a disease or condition, and the timing of administering the composition containing Compound I, or a pharmaceutically acceptable salt or solvate thereof, varies. Thus, in one embodiment, Compound I, or a pharmaceutically acceptable salt or solvate thereof, is used as a prophylactic and are administered continuously to subjects with a propensity to develop conditions or diseases in order to prevent the occurrence of the disease or condition. In another embodiment, Compound I, or a pharmaceutically acceptable salt or solvate thereof, is administered to a subject during or as soon as possible after the onset of the symptoms. In specific embodiments, Compound I, or a pharmaceutically acceptable salt or solvate thereof, is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, Compound I, or a pharmaceutically acceptable salt or solvate thereof, or a formulation containing Compound I, or a pharmaceutically acceptable salt or solvate thereof, is administered for at least 2 weeks, about 1 month to about 5 years.

Exemplary Agents for Use in Combination Therapy

In some embodiments, Compound I, or a pharmaceutically acceptable salt or solvate thereof, is administered in combination with chemotherapy, hormone blocking therapy, radiation therapy, monoclonal antibodies, or combinations thereof.

In certain embodiments, the at least one additional therapy is administered at the same time as Compound I, or a pharmaceutically acceptable salt or solvate thereof. In certain embodiments, the at least one additional therapy is administered less frequently than Compound I, or a pharmaceutically acceptable salt or solvate thereof. In certain embodiments, the at least one additional therapy is administered more frequently than Compound I, or a pharmaceutically acceptable salt or solvate thereof. In certain embodiments, the at least one additional therapy is administered prior to administration of Compound I, or a pharmaceutically acceptable salt or solvate thereof. In certain embodiments, the at least one additional therapy is administered after administration of Compound I, or a pharmaceutically acceptable salt or solvate thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

In some embodiments, anti-cancer agents for use in combination with Compound I, or a pharmaceutically acceptable salt or solvate thereof, include one or more of the following: abiraterone; abarelix; abraxane, adriamycin; actinomycin; acivicin; aclarubicin; acodazole hydrochloride; acronine; adozelesin; aldesleukin; alemtuzumab; allopurinol; alitretinoin; altretamine; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine—cisplatin; gemtuzumab ozogamicin; goserelin acetate; histrelin acetate; hydroxyurea; idarubicin hydrochloride; ifosfamide; iimofosine; ibritumomab tiuxetan; idarubicin; idarubicin; ifosfamide; imatinib mesylate; imiquimod; interleukin Il (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; pomalidomide, porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I$^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate;

vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Monoclonal antibodies include, but are not limited to, trastuzumab (Herceptin) and rituximab (Rituxan).

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefitinib or imatinib, or agents to treat signs or symptoms induced by such therapy including allopurinol, filgrastim, granisetron/ondansetron/palonosetron, dronabinol.

In one aspect, Compound I, or a pharmaceutically acceptable salt or solvate thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, carfilzomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with Compound I, or a pharmaceutically acceptable salt or solvate thereof.

Further examples of anti-cancer agents for use in combination with Compound I, or a pharmaceutically acceptable salt or solvate thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; activin inhibitors, PKM2 inhibitors, c-fms inhibitors and histone deacetylase inhibitors. Further examples of anti-cancer agents for use in combination with Compound I, or a pharmaceutically acceptable salt or solvate thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with Compound I, or a pharmaceutically acceptable salt or solvate thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.).

Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with Compound I, or a pharmaceutically acceptable salt or solvate thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with a Compound I, or a pharmaceutically acceptable salt or solvate thereof, include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, Compound I, or a pharmaceutically acceptable salt or solvate thereof, is used to treat cancer in combination with: an antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (–)-Phenylahistin, Myoseverin B, Resverastatin phosphate sodium.

In one aspect, Compound I, or a pharmaceutically acceptable salt or solvate thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, Compound I, or a pharmaceutically acceptable salt or solvate thereof, is used in combination with anti-emetic agents to treat nausea or emesis, which result from the use of Compound I, or a pharmaceutically acceptable salt or solvate thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, Compound I, or a pharmaceutically acceptable salt or solvate thereof, is used in combination with an agent useful in the treatment of anemia. Such an anemia treatment agent is, for example, a continuous eythropoiesis receptor activator (such as epoetin-α).

In some embodiments, Compound I, or a pharmaceutically acceptable salt or solvate thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In one aspect, Compound I, or a pharmaceutically acceptable salt or solvate thereof, is administered in combination with one or more immunosuppressants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions. Immunosuppressants include, without limitation, glucocorticoids, cytostatics, antibodies and drugs that act on immunophilins. Examples of glucocorticoids include cortisol, cortisone, prednisone, prednisolone, methylprednisolone, dexamethasone, betamethasone, triamcinolone, beclometasone, fludrocortisone, deoxycorticosterone, and aldosterone. Examples of cytostatics include alkylating agents (e.g., nitrogen mustards such as cyclophosphamide, nitrosoureas, platinum compounds) and antimetabolites (e.g., folic acid analogues such as methotrexate, purine analogues such as azathioprine and mercaptopurine, pyrimidine analogues such as fluorouracil, protein synthesis inhibitors). Examples of drugs for use in the methods described include ciclosporin, tacrolimus, sirolimus, interferons, opioids, TNF binding proteins, mycophenolate, and fingolimod. Examples of antibodies useful for co-administration with Compound I, or a pharmaceutically acceptable salt or solvate thereof, in a method described herein include Antithymocyte globulin, 1D09C3, Adalimumab/D2E7 (Humira; Trudexa), Afelimomab, Afutuzumab/GA101 (type II), Alemtuzumab/Campath-1H (MabCampath), Apolizumab/Hu1D10, Aselizumab, Atlizumab, Basiliximab (Simulect), Bectumomab/IMMU-LL2, Belimumab (Benlysta, LymphoStat-B), Bertilimumab, BL22/CAT-3888, Brentuximab/cAC10/SGN-35, Briakinumab/ABT-874, Canakinumab/ACZ885 (Ilaris), Certolizumab pegol/CDP870 (Cimzia), Clenoliximab, Dacetuzumab/SGN-40, Daclizumab (Zenapax), Eculizumab/5G1.1 (Soliris), Efalizumab (Raptiva, formerly Xanelim), Epratuzumab/hLL2/IMMU-102 (Lymphocyde©), Fontolizumab, Fresolimumab/GC-1008, Galiximab/IDEC-114, Gavilimomab/ABX-CBL, Gemtuzumab, Golimumab/CNTO148 (Simponi), HL2434P (IMMU-114), Ibritumomab tiuxetan (MXDPTA)/IDEC Y2B8 (Zevalin), Infliximab/chimeric A2 (cA2) (Remicade), Inolimomab/BT563, Inotuzumab, Keliximab/IDEC CE9.1, Lerdelimumab/CAT-152, Lintuzumab/HuM195 (Zamyl), LMB-2, Lorvotuzumab mertansine, Lumiliximab/IDEC-152, Lym-1 (Oncolym), MDX-060, Mepolizumab/SB-240563, Metelimumab/CAT-192, Mogamulizumab/KW-0761/AMG-761, Moxetumomab pasudotox/CAT-8015/HA22, Muromonab-CD3 (Orthoclone OKT3), Natalizumab (Tysabri, Antegren), Nerelimomab/CDP571, Ocrelizumab/PRO70769 (type I), Odulimomab, Ofatumumab/2F2/HuMax-CD20 (Arzerra) (type I), Omalizumab (Xolair), Otelixizumab/TRX4, Pascolizumab/SB 240683, Reslizumab/SCH 55700 (Cinquil), Rituximab/chimeric 2B8 (IDEC-C2B8) (Rituxan, MabThera) (type I), Ruplizumab (Antova), SAR-3419, Secukinumab/AIN-457, SGN30, Siplizumab/MEDI-507, Teplizumab/MGA031/hOKT3γ1(Ala-Ala), Tocilizumab (Actemra), Tositumomab (type II), Ustekinumab/CNTO 1275 (Stelara), Vedolizumab/MNL-0002, Veltuzumab/IMMU-106/hA20 (type I), Visilizumab (Nuvion), Zanolimumab/HuMax-CD4, Zolimomab aritox/H65, Abatacept/CTLA4-Ig/BMS-188667 (Orencia), Belatacept/LEA29Y, Atacicept/BLyS/APRIL-Ig, Etanercept/TNFR-Ig (Enbrel), Pegsunercept/pegylated TNFR-Ig, Alefacept (Amevive), and Rilonacept (Arcalyst). Immunosuppressive antibodies include antibodies that target complement-dependent proteins and interleukins.

In some embodiments, Compound I, or a pharmaceutically acceptable salt or solvate thereof, is administered with a corticosteroid. In some embodiments, a Compound I, or a pharmaceutically acceptable salt or solvate thereof, is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents useful for combination with Compound I, or a pharmaceutically acceptable salt or solvate thereof, as described herein include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, Compound I, or a pharmaceutically acceptable salt or solvate thereof, is administered in combination with Cyclosporin A (CsA) or tacrolimus (FK506). In one embodiment, Compound I, or a pharmaceutically acceptable salt or solvate thereof, is administered to a mammal in combination with an anti-inflammatory agent including, but not limited to, non-steroidal anti-inflammatory drugs (NSAIDs), phosphodiesterase-4 inhibitors. JNK kinase inhibitors and corticosteroids (glucocorticoids).

In some embodiments, Compound I, or a pharmaceutically acceptable salt or solvate thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, Compound I, or a pharmaceutically acceptable salt or solvate thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, Compound I, or a pharmaceutically acceptable salt or solvate thereof, is co-administered with an analgesic.

In some embodiments, Compound I, or a pharmaceutically acceptable salt or solvate thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, liver, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

In some embodiments, Compound I, or a pharmaceutically acceptable salt or solvate thereof, is administered with a glucose-lowering agent. In some embodiments, the glucose-lowering agent is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, Compound I, or a pharmaceutically acceptable salt or solvate thereof, is administered with metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, Compound I, or a pharmaceutically acceptable salt or solvate thereof, is administered with a lipid-lowering agent.

In some embodiments, Compound I, or a pharmaceutically acceptable salt or solvate thereof, is administered in combination with at least one additional therapy used to treat cardiovascular disease. In some embodiments, the therapy used to treat cardiovascular disease is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, and a fibrate, and any combination thereof.

Kits and Articles of Manufacture

Described herein are kits for treating a condition, disease or disorder associated with LOXL2 activity comprising administering to said individual Compound I, or a pharmaceutically acceptable salt or solvate thereof.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of LOXL2, or in which LOXL2 is a mediator or contributor to the symptoms or cause.

The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

A kit will typically include one or more additional containers, each with one or more of various materials (such as reagents, optionally in concentrated form, and/or devices)

desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising Compound I, or a pharmaceutically acceptable salt or solvate thereof, is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following examples are provided for illustrative purposes only and not to limit the scope of the claims provided herein. Compound I was prepared as outlined in International Patent Application no. PCT/US2016/020732 filed Mar. 3, 2016. The mesylate salt was prepared by treating Compound I with methanesulfonic acid in acetonitrile.

Example A-1: Capsule Formulation of Compound 1

Compound 1 was directly added to a size 9 capsule (Torpac, Inc., New Jersey).

Example A-2: Tablet Formulations

Two different tablet formulations were manufactured at 50 mg and 250 mg strengths (based on amount of Compound I). Tablets are manufactured according to standard tableting techniques.

TABLE 1

Formulation A
250 mg dose (Compound I)

|  | Wt % | Wt per Tablet (mg) | Wt per 50-g batch (g) |
|---|---|---|---|
| Compound 2 | 35.27% | 317.42 | 17.634 |
| Prosolv HD90 | 55.73% | 501.58 | 27.866 |
| Ac-Di-Sol | 5.00% | 45.00 | 2.500 |
| HPC Klucel EXF | 3.00% | 27.00 | 1.500 |
| Aerosil 200 | 0.50% | 4.50 | 0.250 |
| Magnesium Stearate | 0.50% | 4.50 | 0.250 |
| Total | 100.00% | 900.00 | 50.000 |

TABLE 2

Formulation B
250 mg dose (Compound I)

|  | Wt % | Wt per Tablet (mg) | Wt per 50-g batch (g) |
|---|---|---|---|
| Compound 2 | 35.27% | 317.42 | 17.634 |
| Avicel PH102 | 14.06% | 126.52 | 7.029 |
| Parteck M200 (Mannitol) | 42.17% | 379.56 | 21.087 |
| Explotab | 5.00% | 45.00 | 2.500 |
| PVP VA 64 | 3.00% | 27.00 | 1.500 |
| PRUV | 0.50% | 4.50 | 0.250 |
| Total | 100.00% | 900.00 | 50.000 |

Two different tablet strength formulations were manufactured at 50 mg and 250 mg strengths (based on amount of Compound I). Tablets are manufactured according to standard tableting techniques and stored at 20° C. to 25° C. The tablets are formulated as a direct blend and compressed into 900 mg capsule shaped tablets.

TABLE 3

Composition of Compound 2 Tablets, 50 mg (Compound I)

| Component | Amount per Tablet - (% wt) |
|---|---|
| Compound 2 | 62.46 mg (6.94%) |
| Silicified microcrystalline cellulose | 756.5 mg (84.1%) |
| Croscarmellose sodium | 45.00 mg (5.0%) |
| Hydroxypropylcellulose | 27.00 mg (3.0%) |
| Collodial silicon dioxide | 4.50 mg (0.5%) |
| Magnesium Stearate | 4.50 mg (0.5%) |
| Total | 900 mg |

TABLE 4

Composition of Compound 2 Tablets, 250 mg (Compound I)

| Component | Amount per Tablet - (% wt) |
|---|---|
| Compound 2 | 312.3 mg (34.7%) |
| Prosolv HD90 | 506.7 mg (56.3%) |
| Ac-Di-Sol ® | 45.00 mg (5.0%) |
| HPC Klucel EXF | 27.00 mg (3.0%) |
| Aerosil 200 | 4.50 mg (0.5%) |
| Magnesium Stearate | 4.50 mg (0.5%) |
| Total | 900 mg |

Example A-3: Oral Solution

Oral solutions of Compound 2 were prepared that had a concentration from 5 mg/mL to 50 mg/mL of Compound 2 in an aqueous diluent containing sodium citrate dehydrate, citric acid anhydrous, FONA Bitterness Masking Flavors, and sucralose in an aqueous solution.

Solutions were prepared as follows. Add the required amount of water to the container (see Table 3 for quantities). Weigh the required amount of sodium citrate and citric acid, add to the container and mix until dissolved. Weigh the required amount of the flavoring agent (FONA Bitterness Masking Flavors) and add this to the solution and mix until homogenous. Weigh the required amount of sucralose and add this to the solution and mix until dissolved. Measure the appearance (colorless to slightly yellow) and pH (pH within range of 3 to 5) to assure the diluent meets specification. Weigh the required amount of compound 2 and slowly add to the diluent. Mix until all compound 2 is dissolved (sonicate, warm, or stir if necessary). The pH is within range of 3 to 5 and appearance colorless to slightly yellow. Dispense up to 80 mL of the bulk dosing solution in a glass container.

There were no significant changes in physical appearance, potency, purity, or pH of the oral solution when stored at 2° C. to 8° C. or 25° C./60% RH for up to 7 days in glass containers. The recommended storage of the oral solution is either at 2° to 8° C. or 20° C. to 25° C. in a glass container for up to 7 days.

TABLE 5

Composition of Compound 2 Oral Solution

| Component | Amount per unit Concentration (mg/mL) |
|---|---|
| Compound 2 | 6.3 mg/mL to 63 mg/mL |
| Sodium Citrate Dihydrate | 9.50 |
| Citric Acid Anhydrous | 10.50 |
| Sucralose | 2.00 |
| Fona Bitterness Masking Flavor - Liquid (936.0504 U) | 0.50 |
| Fona Bitterness Masking Flavor - Solid (936.0592 U) | 0.50 |
| Water, purified | q.s to 1 mL |

Example A-4: Pharmacokinetic Study of Compound 1 or 2 in Rat

Compound 1 or 2 was administered PO in solution at 30 mg/kg or 15 mg/kg compound 1 in a capsule [Compound 1 was directly added to a size 9 capsule (Torpac, Inc., New Jersey)].

Blood samples were taken from each rat (approximately 0.3 mL total blood per time point) at pre-dose, 5 or 15 min and then at various time points up to 24 hours post-dose. Samples were collected on wet ice in tubes containing potassium EDTA (w/v in normal saline; BD Biosciences, Franklin Lakes, N.J. Plasma samples, prepared by centrifugation of whole blood, were stored frozen (−80° C.) prior to analysis. All other reagents were of analytical grade.

Analysis was performed on an LC-MS/MS systems comprised of a Sciex API-4000Qt tandem mass spectrometer (AB Sciex, Foster City, Calif.) interfaced to an HPLC system consisting of a single Agilent 1200 Series Quaternary system pump (Santa Clara, Calif.) and a LEAP PAL autoinjector (Greenville, S.C.). Analyses were performed using an Agilent Zorbax SB-C8 column (2.1×50 mm; 5 μm) for chromatographic separations at room temperature. Data is described in Table 6.

TABLE 6

Rat Pharmacokinetics of Compound 1 or 2 Using Various Dosing Forms.

| | Species Rat | | | |
|---|---|---|---|---|
| Compound | 1 | 1 | 2 | 1 |
| Route | IV | PO | PO | PO |
| Vehicle | Saline | 0.5% MC | 0.5% MC | Capsule |
| Dose (mg/kg) | 2 | 30 | 30 | 15 |
| Fast/Fed | Fed | Fasted | Fasted | Fasted |
| Sex | M | M | M | M |
| $AUC_{(0-t\ hr)}$ (μg · hr/mL) | 0.14 | 1.4 | 2.0 | 0.74 |
| $AUC_{0-t\ hr}$/Dose | 0.07 | 0.05 | 0.07 | 0.05 |
| $C_{max}$ (μg/mL) | 0.63 | 1.7 | 2.6 | 1.2 |
| $T_{max}$ (hr) | 0.083 | 0.25 | 0.42 | 0.6 |
| F(%) | 100 | 71 | 95 | 69 |

IV—intravenous;
PO—oral;
MC—methylcellulose;
M = male;
AUC—area under plasma concentration-time curve;
$C_{max}$—peak plasma concentration;
$T_{max}$—time to peak plasma concentration;
% F—bioavailability calculated from $AUC_{0-t}$ PO/$AUC_{0-t}$ IV.

Example A-5: Pharmacokinetic Study of Compound 1 or 2 in Dog

Compound 1 or 2 was administered PO in solution at 100 or 300 mg/kg. Compound 2 was administered PO in a capsule as well as in two different tablet formulations (Formulation A or B). The data are described in Table 5. Emesis was prevalent in all dose groups, but clinical observations concluded that the oral capsule and potentially the tablet were better tolerated than and of the oral solutions.

Blood samples were taken from each dog (approximately 1 mL total blood per time point) at pre-dose, 5 or 15 min and then at various time points up to 24 hours post-dose. Samples were collected on wet ice in tubes containing potassium EDTA (w/v in normal saline; BD Biosciences, Franklin Lakes, N.J. Plasma samples, prepared by centrifugation of whole blood, were stored frozen (−80° C.) prior to analysis. All other reagents were of analytical grade.

Analysis was performed on an LC-MS/MS systems comprised of a Sciex API-4000Qt tandem mass spectrometer (AB Sciex, Foster City, Calif.) interfaced to an HPLC system consisting of a single Agilent 1200 Series Quaternary system pump (Santa Clara, Calif.) and a LEAP PAL autoinjector (Greenville, S.C.). Analyses were performed using an Agilent Zorbax SB-C8 column (2.1×50 mm; 5 μm) for chromatographic separations at room temperature.

TABLE 7

Dog Pharmacokinetics of Compound 1 or 2 Using Various Dosing Forms.

| Species | Dog | | | | | |
|---|---|---|---|---|---|---|
| Compound | 1 | 1 | 2 | 2 | 2 | 2 |
| Route | IV | PO | PO | PO | PO | PO |

TABLE 7-continued

Dog Pharmacokinetics of Compound 1 or 2 Using Various Dosing Forms.

| Vehicle | Saline | 0.5% MC | Citrate | Capsule | Tablet Formulation A | Tablet Formulation B |
|---|---|---|---|---|---|---|
| Dose (mg/kg) | 5 | 100 | 300 | 300 | 100 | 100 |
| Fast/Fed | Fed | Fasted | Fasted | Fasted | Fasted | Fasted |
| Sex | M | M | M | M | M | M |
| $AUC_{(0-t\ hr)}$ (µg · hr/mL) | 1.4 | 85 | 286 | 100 | 75.6 | 63.9 |
| $AUC_{0-t\ hr}$/Dose | 0.28 | 0.85 | 0.95 | 0.33 | 0.76 | 0.64 |
| $C_{max}$ (µg/mL) | 2.5 | 27 | 143 | 80 | 33.7 | 25.1 |
| $T_{max}$ (hr) | 0.083 | 1.3 | 0.3 | 0.5 | 0.4 | 0.8 |
| F(%) | 100 | 283 | 339 | 100 | 253 | 210 |

IV—intravenous;
PO—oral;
MC—methylcellulose;
M = male beagle dog;
AUC—area under plasma concentration-time curve;
$C_{max}$—peak plasma concentration;
$T_{max}$—time to peak plasma concentration;
% F—bioavailability calculated from $AUC_{0-t}$ PO/$AUC_{0-t}$ IV.

Example A-6: Parenteral Pharmaceutical Composition

To prepare a parenteral pharmaceutical composition suitable for administration by injection (subcutaneous, intravenous), 1-1000 mg of Compound (I), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-7: Topical Gel Composition

To prepare a pharmaceutical topical gel composition, Compound (I), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: Preparation of Concentrated Conditioned Media (CCM)

Human LOXL2/CHO and human LOX/HEK stable cell lines were cultured under normal growth conditions in 15 cm tissue culture plates until cells were ~80% confluent. Cells were then washed with PBS before the addition of 25-30 mL serum-free media (Phenol red-free DMEM/F12 mix w/glutamax containing pen/strep, 10-100 µM $CuCl_2$±0.1% BSA). Cells were incubated at 37° C., 5% $CO_2$ in serum-free media for 40-48 hours before the conditioned media was removed and centrifuged at 2000 rpm for 5 min at 4° C. to pellet cells/debris. The media was concentrated 10-20× using 10-30 MWCO centriprep columns according to the manufacturer's instructions (EMD Millipore, Billerica, Mass.) before aliquoting and storing at −80° C.

Example B-2: Human LOXL2 CCM Assay

LOXL2 amine oxidase activity was evaluated by measuring Amplex Red fluorescence using 10-20× concentrated conditioned media (non BSA-containing) from CHO cells stably expressing human LOXL2. To assay for amine oxidase activity, 10 µL of the concentrated conditioned media was incubated with 2 µL of test compound in DMSO and 73 µL Assay Buffer (50 mM Borate Buffer, pH8) for 2 h at 37° C. After the 2 h incubation, 5 µL of 10 mM 1,5-Diaminopentane (DAP) diluted in Assay Buffer and 10 µL of Amplex Red Mix (8.5 µL Assay Buffer+0.5 µL of 10 mM Amplex Red+1 µL of 500 U/ml Horseradish Peroxidase) were added and the plate mixed and immediately placed on the FlexStation for fluorescence measurements. Fluorescence was read in kinetic mode every 2 min for 0.5-1 hour at excitation=544 and emission=590. The amine oxidase activity was calculated from the slope of the linear portion of the curve. Wells containing vehicle (DMSO) represented maximum activity and were set to 0% inhibition and wells containing 100 µM βAPN (3-aminopropionitrile) represented no activity and were set to 100% inhibition.

TABLE 8

| Compound | $IC_{50}$ |
|---|---|
| Rac-1 | A |
| Ent-1 | A |
| 1 | A |
| 2 | A |

A is <300 nM.

Example B-3: Human LOX CCM Assay

Human LOX amine oxidase activity was evaluated by measuring Amplex Red fluorescence using 10-20× concentrated conditioned media (BSA-containing) from HEK cells stably expressing human LOX. To assay for amine oxidase activity, 10 µL of the concentrated conditioned media was incubated with 2 µL of test compound in DMSO and 73 µL Assay Buffer (50 mM Borate Buffer, pH8) for 2 h at 37° C. After the 2 h incubation, 5 µL of 10 mM 1,5-Diaminopentane (DAP) diluted in Assay Buffer and 10 µL of Amplex Red Mix (8.5 µl Assay Buffer+0.5 µl of 10 mM Amplex Red+1 µL of 500 U/mL Horseradish Peroxidase) were added and the plate mixed and immediately placed on the FlexStation for fluorescence measurements. Fluorescence was read in kinetic mode every 2 min for 1 hour at excitation=544 and emission=590. The amine oxidase activity was calculated from the slope of the linear portion of the curve. Wells containing vehicle (DMSO) represented maximum activity and were set to 0% inhibition and wells containing 100 µM βAPN (3-aminopropionitrile) represented no activity and were set to 100% inhibition.

Example B-4: Human LOXL2 Purified Recombinant Protein Assay

The amine oxidase activity was evaluated by measuring Amplex Red fluorescence using commercially available purified, recombinant human LOXL2 (Sino Biologicals, Beijing, China). To assay for amine oxidase activity, 10 µL of 0.025 µg/µL purified, recombinant LOXL2 diluted in Assay buffer Buffer (50 mM Borate Buffer, pH8) was incubated with 2 µL of test compound in DMSO and 73 µL Assay Buffer for 2 h at 37° C. After the 2 h incubation, 5 µL of 10 mM 1,5-Diaminopentane (DAP) diluted in Assay Buffer and 10 µL of Amplex Red Mix (8.5 µl Assay Buffer+0.5 µL of 10 mM Amplex Red+1 µL of 500 U/mL Horseradish Peroxidase) are added and the plate mixed and immediately placed on the FlexStation for fluorescence measurements. Fluorescence is read in kinetic mode every 2 min for 0.5-1 hour at excitation=544 and emission=590. The amine oxidase activity is calculated from the slope of the linear portion of the curve. Wells containing vehicle (DMSO) represented maximum activity and were set to 0% inhibition and wells containing 100 µM βAPN (3-aminopropionitrile) represented no activity and were set to 100% inhibition.

Example B-5: Human LOXL3 Purified Recombinant Protein Assay

The amine oxidase activity was evaluated by measuring Amplex Red fluorescence using commercially available purified, recombinant human LOXL3 (R&D Systems, Minneapolis, Minn.). To assay for amine oxidase activity, 10 µL of 0.075 µg/µL purified, recombinant LOXL3 diluted in Assay buffer Buffer (50 mM Borate Buffer, pH8) was incubated with 2 µL of test compound in DMSO and 73 µL Assay Buffer for 2 h at 37° C. After the 2 h incubation, 5 µL of 10 mM 1,5-Diaminopentane (DAP) diluted in Assay Buffer and 10 µL of Amplex Red Mix (8.5 µL Assay Buffer+0.5 µL of 10 mM Amplex Red+1 µL of 500 U/mL Horseradish Peroxidase) was added and the plate mixed and immediately placed on the FlexStation for fluorescence measurements. Fluorescence was read in kinetic mode every 2 min for 0.5-1 hour at excitation=544 and emission=590. The amine oxidase activity was calculated from the slope of the linear portion of the curve. Wells containing vehicle (DMSO) represented maximum activity and were set to 0% inhibition and wells containing 100 µM BAPN (3-aminopropionitrile) represented no activity and were set to 100% inhibition.

TABLE 9

$IC_{50}$ values for Compound 1 in LOX, LOXL2 and LOXL3 assays.

| Activity Assay | $IC_{50}$ (µM) |
|---|---|
| LOXL2 (CCM) | 0.0751 |
| LOXL2 (CCM containing BSA) | 0.116 |
| LOXL2 (purified, recombinant) | 0.209 |
| LOX (CCM containing BSA) | 47.0 |
| LOXL3 (purified, recombinant) | 1.21 |

Example B-6: LOXL2 Human Blood Assay

The amine oxidase activity of human LOXL2 in the context of human whole blood was measured using an Amplex Red assay. Purified human recombinant LOXL2 (Sino Biologicals, Beijing, China) was resuspended to 0.25 µg/mL using sterile water, then 16 µL LOXL2 added to 182 µL fresh human blood collected in heparin vacutainer tubes. 2 µL test compound in DMSO (or DMSO alone) was added and incubated at 37° C. for 2 h. After the 2 h incubation, the blood was centrifuged at 2000×g for 15 min at room temperature to isolate the plasma. 50 µL of plasma was removed and mixed with 25 µL of 40 mM DAP (diluted in water) and 25 µL Amplex Red Mix (23.5 µL 50 mM Borate Buffer, pH 8+0.5 µL 10 mM Amplex Red+1 µL 500 U/ml Horseradish Peroxidase). Samples were mixed and immediately placed on the FlexStation for fluorescence measurements. Fluorescence was read in kinetic mode every 2 min for 1 hour at excitation=544 and emission=590. The amine oxidase activity was calculated from the slope of the linear portion of the curve. Wells containing vehicle (DMSO) represented maximum activity and were set to 0% inhibition and wells containing blood not spiked with LOXL2 represented no activity and were set to 100% inhibition.

Example B-7: Mouse Oropharyngeal Bleomycin Model of Lung Fibrosis

Lung fibrosis was induced in C57Bl/6 male mice by administering bleomycin (0.1-4 U/kg) via oropharyngeal instillation. Mice were either pretreated with vehicle or test compound orally, intraperitoneally, intravenously or subcutaneously either prophylactically (1 day to 1 hour before bleomycin instillation) or therapeutically (7-14 days post bleomycin instillation). The route and frequency of dosing were based on previously determined pharmacokinetic properties for the LOXL2 inhibitor in mouse. After bleomycin instillation, animals were monitored daily for weight loss and clinical signs for 14-28 days prior to sacrifice. Animals were euthanized at study termination and weighed. Blood (for isolation of plasma) and bronchoalveolar lavage fluid were collected and frozen for subsequent analyses. Lungs were removed, weighed, then either inflated and fixed by instillation of 10% formalin and prepared for histological examination or homogenized in 1 mL PBS for collagen determination using a hydroxyproline assay. For histological examination, lung slices were stained with Masson's trichrome or picrosirius red to measure fibrillar collagen as an indicator of fibrosis and an Ashcroft score of lung fibrosis and inflammatory damage determined. For lung hydroxyproline content, 0.5 ml of the lung homogenate is removed and added to 0.5 mL 12 N HCl and the samples heated at 120° C. overnight. After the acid hydrolysis, 25-100 µL of the supernatant is dried down, resuspended in 25 µL water and the hydroxyproline content determined by the addition of 0.5 mL Chloramine T solution (140 mg Chloramine T in 6.5 ml ddH$_2$O+1 ml n-propanol+2.5 mL 1M sodium acetate) and incubation at room temperature for 20 min. After the incubation, 0.5 mL Erlich's solution (1.48 g of 4-(dimethylamino (benzaldehyde) in 7 mL n-propanol+2.88 ml 60% perchloric acid and 0.12 mL ddH$_2$O) is added and incubated at 65° C. for 15 min before reading the absorbance at 550 nm.

Example B-8: Dose-Responsive Efficacy in Lung Fibrosis

Compound Rac-1 was orally administered prophylactically to bleomycin-instilled mice at 3, 10, 30 or 60 mg/kg/day with lungs harvested for histologic assessment on Day 14. FIG. 1 shows the Ashcroft score from histopathology analyses reflecting lung fibrosis in a prophylactic 14-day dose response study of Rac-1 in the mouse bleomycin-induced model of lung fibrosis (*p<0.05; p<0.01; *p<0.001). Rac-1 reduced fibrosis in a dose-related manner suggesting, 30 mg/kg is the minimal dose to achieve maximal anti-fibrotic efficacy.

Example B-9: Prophylactic Vs. Therapeutic Efficacy in Lung Fibrosis

Figure 2:
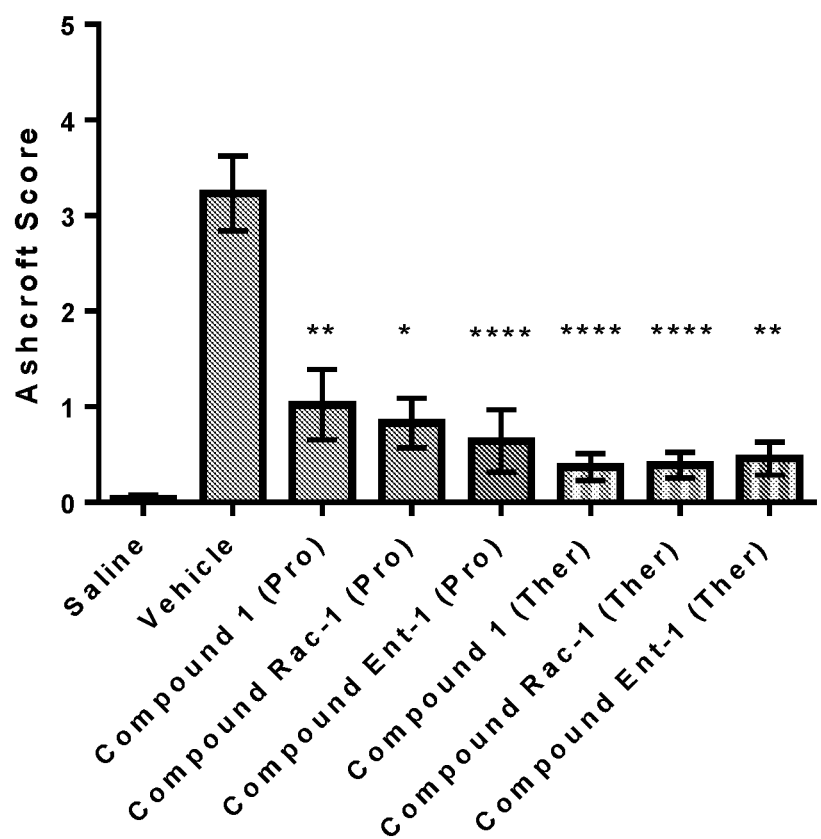
FIG. 2 shows the Ashcroft scores derived from histopathology analyses of trichrome stained lung sections in a mouse bleomycin-induced model of lung fibrosis. Compounds 1, Rac-1, and Ent-1 were dosed at 60 mpk QD in both prophylactic (Pro) and therapeutic (Ther) modes (*$p<0.05$, $p<0.01$, **$p<0.0001$).

Compound 1, Compound Rac-1, and Compound Ent-1 were administered orally at 60 mg/kg/day to bleomycin-instilled mice under two paradigms: prophylactic (dose starting Day −1) and therapeutic (dose starting Day 7). FIG. 2 shows the Ashcroft score from histopathology analyses reflecting lung fibrosis comparing efficacy of Compounds 1, Rac-1, and Ent-1 in both prophylactic (Pro) and therapeutic (Ther) modes in the mouse bleomycin-induced model of lung fibrosis (*p<0.05, p<0.01, **p<0.0001)

Fibrotic status was assessed histologically on Day 21 using Ashcroft score as a primary measure of lung fibrosis. All three compounds significantly reduced fibrosis in the mouse model of lung fibrosis with similar efficacy regardless of whether compound was administered prophylactically or therapeutically.

Example B-10: Reversal of Established Lung Fibrosis

Figure 3:
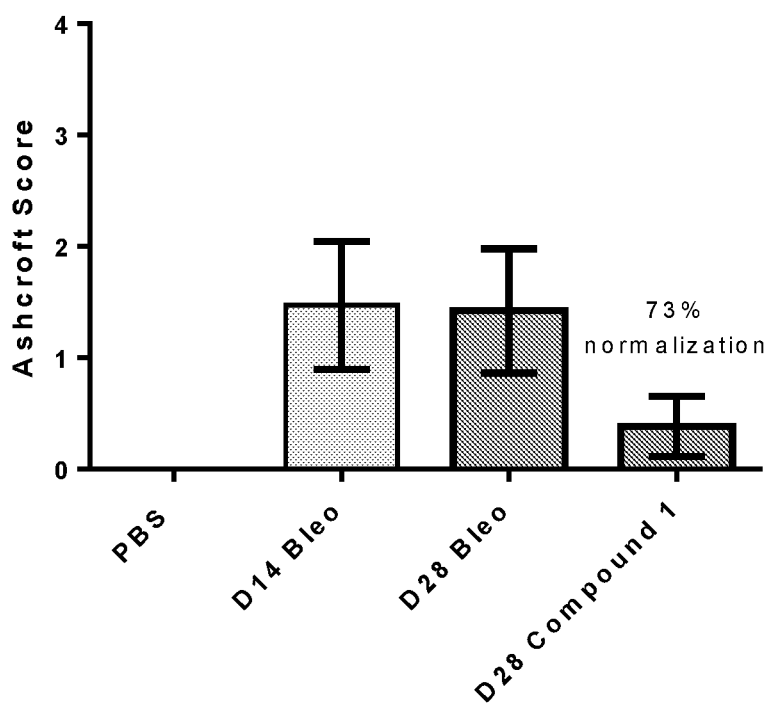
FIG. 3 shows the Ashcroft scores from histopathology analyses reflecting lung fibrosis in a recovery 28-day study where Compound 1 was administered at 60 mg/kg QD starting on Day 14 after bleomycin administration.

The mouse bleomycin-induced lung model is known to develop fibrosis gradually over the first 14 to 21 days but then will spontaneously resolve in younger mice over the next several weeks (Hecker et al., 2014). To determine if LOXL2 inhibitors can accelerate the resolution of established fibrosis, Compound 1 was orally administered starting on Day 14 after bleomycin with lungs harvested for histological analysis on Day 28. The extent of fibrosis remained constant from Day 14 to Day 28 in the vehicle-treated mice. Compound 1 decreased fibrosis with a 73% normalization of Ashcroft score (FIG. 3). FIG. 3 shows the Ashcroft score from histopathology analyses reflecting lung fibrosis in a recovery 28-day study where Compound 1 was administered at 60 mg/kg starting on Day 14.

Example B-11: Effects of Dose Frequency in Lung Fibrosis

Compound Rac-1 was orally administered at a dose of 60 mg/kg to bleomycin-induced mice prophylactically using different dosing paradigms. Efficacy of daily (QD) dosing was compared with that from every other day (Q2D) and every third day (Q3D) dosing with lungs harvested for histological assessment on Day 14. Regardless of dosing frequency, Compound Rac-1 reduced lung fibrosis with QD slightly more effective than Q2D or Q3D (FIG. 4).

Figure 4:
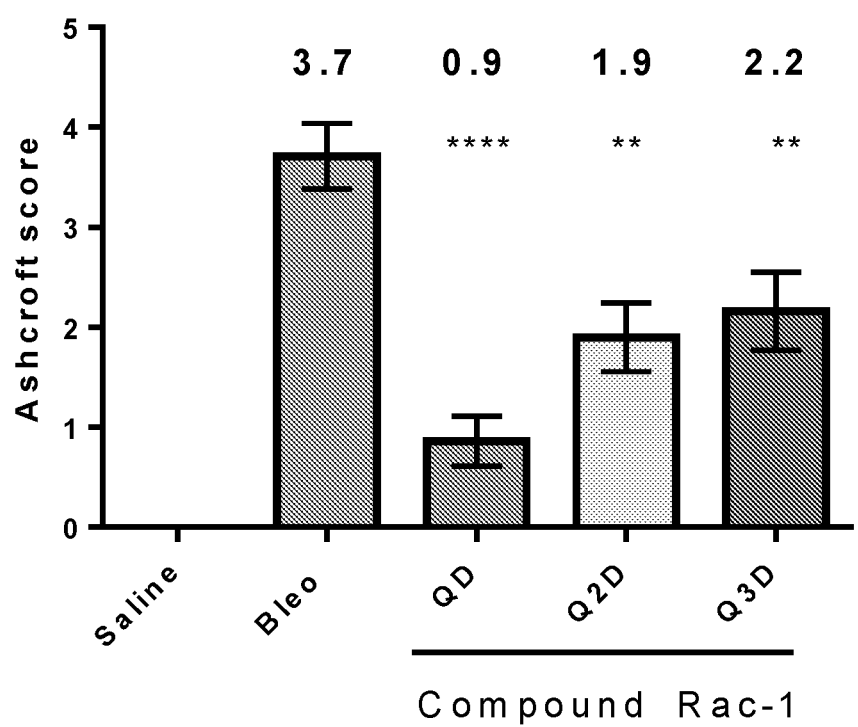
FIG. 4 shows the Ashcroft score from histopathology analyses reflecting lung fibrosis in a prophylactic 14-day study comparing 60 mg/kg QD, 60 mg/kg Q2D and 60 mg/kg Q3D dosing of Compound Rac-1 in the mouse bleomycin-induced model of lung fibrosis ($p<0.01$; **$p<0.0001$).

FIG. 4 shows the Ashcroft score from histopathology analyses reflecting lung fibrosis in a prophylactic 14-day study comparing QD, Q2D and Q3D dosing of Compound Rac-1 in the mouse bleomycin-induced model of lung fibrosis (p<0.01; **p<0.0001).

Example B-12: Comparison of Efficacy with Anti-LOXL2 Antibody in Lung Fibrosis

Figure 5:
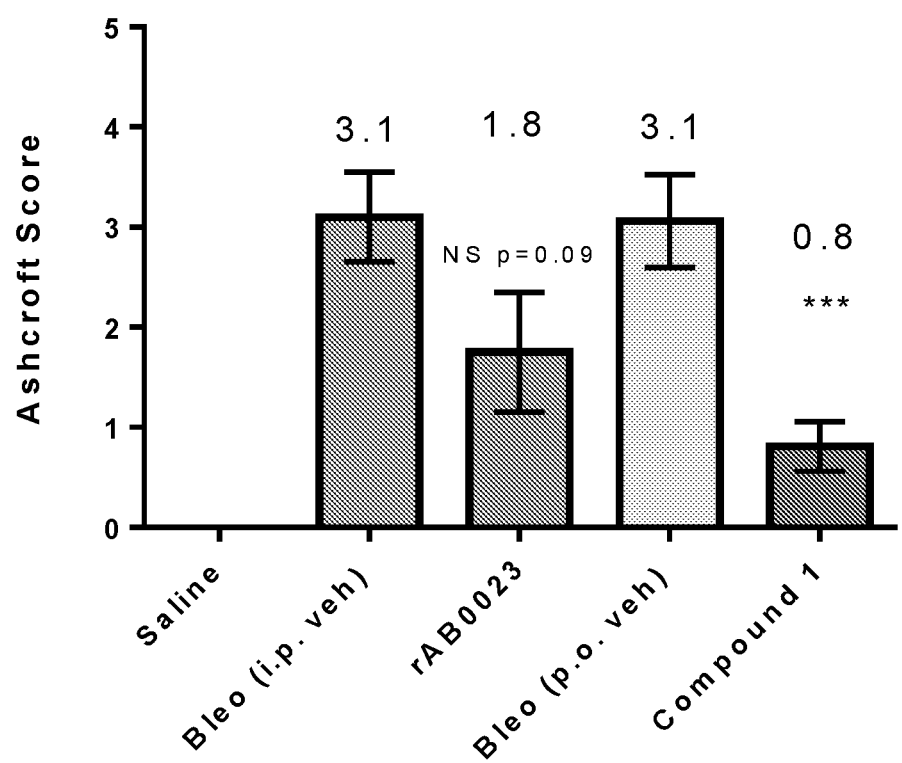
FIG. 5 shows the Ashcroft score from histopathology analyses reflecting lung fibrosis in a prophylactic 14-day study comparing 60 mg/kg QD Compound 1 with 30 mg/kg rAB0023, an antibody to LOXL2.

Efficacy of Compound 1 was compared head-to-head in a study with rAB0023. rAB0023 is a recombinant mouse hybrid antibody that has the heavy chain variable region of the anti-LOXL2 antibody, AB0023, cloned into a murine IgG2a backbone and the light chain variable region of AB0023 cloned into a murine IgG2 backbone. rAB0023 binds to LOXL2 with equal affinity to AB0023, an antibody that has demonstrated efficacy in various in vivo models including the mouse bleomycin-induced model of lung fibrosis (Barry-Hamilton et al., Nat Med. 2010 September; 16(9):1009-17). Compound 1 was orally administered prophylactically at a dose of 60 mg/kg/day starting on Day −1; rAB0023 was administered at 30 mg/kg intraperitoneally (IP) on Day −4, −1, 1, 4, 8 and 11 (bi-weekly) with lungs harvested for histological analysis on Day 14. Compound 1 significantly reduced lung fibrosis in the mouse bleomycin model as evidenced by a reduction in Ashcroft score from a mean value of 3.1 to 0.8 (FIG. 5). The rAB0023 antibody showed trends towards reducing Ashcroft score (3.1 to 1.7), but the trends were not statistically significant. The results demonstrate that Compound 1 has efficacy better than rAB0023 in the mouse bleomycin-induced model of lung fibrosis.

FIG. 5 shows the Ashcroft score from histopathology analyses reflecting lung fibrosis in a prophylactic 14-day study comparing 60 mg/kg Compound 1 with 30 mg/kg rAB0023, an antibody to LOXL2.

Example B-13: Combination with Other Anti-Fibrotic Agents for Lung Fibrosis

LOXL2 inhibitors can be used in combination with other anti-fibrotic drugs for lung fibrosis. Pirfenidone and nintedanib are currently approved for treatment of lung fibrosis in patients with IPF. LOXL2 inhibitors are tested alone and in combination with pirfenidone in either prophylactic or therapeutic dosing modalities for 14-28 days. LOXL2 inhibitors are tested also alone and in combination with nintedanib in either prophylactic or therapeutic dosing modalities for 14-28 days. Fibrosis is measured using Ashcroft scoring or hydroxyproline concentration as described above. Combination therapy is advantageous when efficacy is greater than either agent alone or when the dose required for either drug is reduced thereby improving the side effect profile.

Example B-14: Mouse Alport Model of Kidney Fibrosis

Mice with mutations in one of the collagen IV genes of glomerular basement membrane collagen, Collagen IV-α3/α4/α5, have defects in glomerular function with development of kidney fibrosis. These mice develop renal dysfunction and die prematurely of renal failure with specific timing dependent on the strain background upon which the mutation is present. Compound 1 was administered orally to Col4A3 deficient mice on a 129/Sv background either prophylactically (ca. weeks 2-3 of age) or therapeutically (ca. weeks 4-6 wks of age). Mice were either sacrificed at a predefined time (7-9 wks of age) or continually dosed until they lost >15% of their body weight which precedes death by 1-3 days. If specifically terminated, mice were perfused transcardially with PBS, and one kidney clamped at the renal artery and the other perfused with Dynabeads for magnetic isolation of glomeruli. The other kidney was halved and a small sample of renal cortex fixed for transmission electron microscopic (TEM) analysis and a second sample of renal cortex used for RNA isolation. The other half of the bisected kidney was embedded in OCT for immunohistochemical analysis. RNA from glomeruli and renal cortex was analyzed by real time RT-PCR for genes of interest including MMP-10, MMP-12, IL6, MCP-1, TGF-b1, CTGF, MMP-2, and MMP-9. Immunohistochemical analysis included staining for collagen 1, CD45, fibronectin, smooth muscle actin, WT-1, and integrin alpha 8/laminin α5. Collagen 1 staining was blindly analyzed for fibrosis scoring, and fibronectin staining was blindly analyzed for glomerulosclerosis scoring. For all studies albuminuria was assessed weekly and BUN at the time of tissue harvest.

Compound 1 improved both glomerular and interstitial fibrosis in the Col4A3 deficient mouse when administered orally at a dose of 30 mg/kg/day starting at 2 weeks of age (FIG. 6a), a time when the kidneys are fairly normal in this model. Fibrosis was assessed at 7 weeks of age using blinded assessment of collagen and fibronectin immunohistochemistry. Compound 1 also improved fibrosis when dosing was initiated at 5 weeks of age, which can be considered a therapeutic intervention.

FIG. 6a shows Glomerular sclerosis (left) and interstitial fibrosis (right) scores reflecting kidney fibrosis in the Col4A3 deficient mouse model of Alport syndrome and chronic kidney disease. Samples were harvested at 7 weeks of age after oral administration of Compound 1 at 30 mg/kg starting at 2 weeks or 5 weeks of age (**$p<0.01$).

Example B-15: Combination with Other Anti-Fibrotic Agents for Renal Fibrosis LOXL2 inhibitors can be used in combination with other drugs for chronic kidney diseases including Alport syndrome. Angiotensin II converting enzyme (ACE) inhibitors and angiotensin receptor blockers (ARBs) are frequently used in renal disease patients. LOXL2 inhibitors are tested alone and in combination with ramipril (ACE inhibitor) or candesartan (ARB) in prophylactic starting at 2-3 weeks of age. If efficacious after prophylactic dosing, combination studies in therapeutic dosing modality (starting 4-6 weeks of age) will be run. Fibrosis is measured using histologically as described above and renal function is measured using proteinuria and/or serum BUN. Effects of combination therapy on survival are also measured as described above. Combination therapy is advantageous when efficacy is greater than either agent alone or when the dose required for either drug is reduced thereby improving the side effect profile.

Example B-16: Mouse Orthotopic Breast Cancer Model

Compound 1 was evaluated in an orthotopic mouse model of human breast cancer. Tumor stocks were made by subcutaneously (s.c.) injecting MDA-MB-435-GFP cells at a concentration of $5\times10^6$ cells/100 µL into the flank of nude mice. When the s.c. tumors reach 50-100 mm³, tumors were harvested and cut into 1 mm³ fragments. Two tumor fragments were transplanted into the mammary fat pad of each mouse. Compound 1 was administered orally at a dose of 60 mg/kg/day once the average primary tumor volume reached 100 mm³. Docetaxel was administered at 10 mg/kg intravenously once a week for 4 weeks as a positive control. Tumor size was calculated from a measurement of perpendicular minor dimension (W) and major dimension (L) using the formula (W2×L)×½ with W and L measured using a digital caliper. Mice were sacrificed after 4 weeks. Compound 1 attenuated tumor growth with a statistically significant 35% reduction in volume at 4 weeks.

Figure 6B:
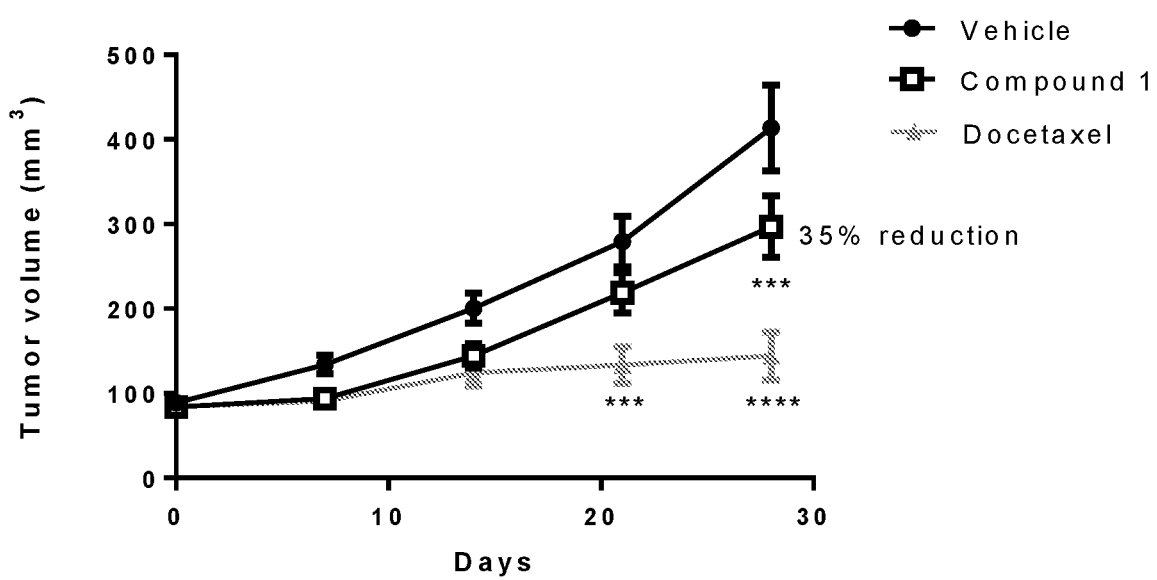
FIG. 6b shows tumor volume in orthotopic human breast cancer model with MDA-MB-435-GFP cells implanted into mammary fat pads of nude mice. Tumor volumes were measured weekly for the 4 week study (*p<0.001, **p<0.0001).

FIG. 6b shows tumor volume in orthotopic human breast cancer model with MDA-MB-435-GFP cells implanted into mammary fat pads of nude mice. Tumor volumes were measured weekly for the 4 week study (*$p<0.001$, **$p<0.0001$).

Example B-17: Mouse Subcutaneous Bleomycin Model of Skin and Lung Fibrosis

Skin and lung fibrosis is induced in female C57Bl/6 mice by administering bleomycin via subcutaneous injection to one (50-100 µg bleo/site) or two sites (50 µg bleo/site) on the backs of mice. For the two site model, animals are anesthetized with isoflurane and bleomycin (100 µl, or PBS control) is injected at the same site daily for 28 days to induce skin and lung fibrosis. In the single site model, mice are restrained and injected at the same location identified using an indelible marker. Mice are either pretreated with vehicle or test compound (1 day to 1 hour) orally, intraperitoneally, intravenously or subcutaneously before bleomycin injection (prophylactic dosing) or 7-14 days post bleomycin injection (therapeutic dosing). Animals are euthanized at study termination and weighed and blood (for isolation of plasma) and bronchoalveolar lavage are collected and frozen for subsequent analyses. Lungs are either removed, weighed, then homogenized in PBS for determination of collagen content using a hydroxyproline assay or inflated and fixed by instillation of 10% formalin and prepared for histological examination by trichrome or picrosirius red staining. Skin biopsies are taken from each injection site using a 6 mm dermal punch biopsy (Acuderm). One punch biopsy is sandwiched in a cassette with a sponge, placed in formalin and prepared for histological examination by H&E, trichrome and/or picrosirius red histologic staining. The other punch biopsy is placed in 0.5 ml PBS and minced using fine scissors. 500 µL 12 N HCl is then added and the samples heated at 120° C. overnight. After the acid hydrolysis, 25-100 µl of the supernatant is dried down, resuspended in 25 µL water and the hydroxyproline content determined by the addition of 0.5 ml Chloramine T solution (140 mg Chloramine T in 6.5 mL ddH$_2$O+1 mL n-propanol+ 2.5 mL 1M sodium acetate) and incubation at room temperature for 20 min. After the incubation, 0.5 ml Erlich's solution (1.48 g of 4-(dimethylamino (benzaldehyde) in 7 ml n-propanol+2.88 mL 60% perchloric acid and 0.12 mL ddH$_2$O) is added and incubated at 65° C. for 15 min before reading the absorbance at 550 nm. The concentration of hydroxyproline in each skin biopsy is determined from a hydroxyproline (purchased from Sigma) standard curve.

Example B-18: Rat/Mouse CCl$_4$ Model of Liver Fibrosis

Liver fibrosis is induced in mice (Balb/c or C57Bl/6) by intraperitoneal administration of CCl$_4$ (0.5-2 ml/kg body weight) diluted in corn oil twice weekly for 4-8 weeks or by oral administration two-three times weekly using an escalating dose protocol (Popov et al. 2011 Gastroenetrology; 140(5): 1642-1652.). Liver fibrosis is induced in rats by either intraperitoneal administration (1-2.5 ml/kg) or by oral administration in oil (mineral, olive or corn) twice weekly for 6-12 weeks. LOXL2 inhibitors are delivered orally, intraperitoneally, intravenously or subcutaneously 1 day to 1 hour prior to the initial CCl$_4$ dosing (prophylactic dosing) or 1-4 weeks after the initial CCl$_4$ dosing (therapeutic dosing). At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E staining and Picrosirius red staining. The remaining tissue is snap frozen at −80° C. for subsequent hydroxyproline analysis of total collagen content.

Example B-19: Mouse Mdr2 Knockout Model of Biliary Fibrosis

Liver disease develops in the BALB/c.Mdr2−/− mouse model with bridging fibrosis/early cirrhosis between 8 and 12 weeks of age (Ikenaga et al. 2015 Am J Pathology, 185: 325-334). Compound 1 was delivered orally at a dose of 30 and 60 mg/kg/day, into BALB/c.Mdr2−/− mice once daily for 6 weeks beginning at week 6 after birth. At the end of the study, mice were anesthetized with isoflurane (1.5% v/v) via precise vaporizer. After laparotomy, portal pressure was measured directly by inserting a high-fidelity pressure catheter into the portal vein and measuring pressure signals for 5 minutes. Serum was collected for analysis of liver (ALT, AST, ALP, and bilirubin) and kidney (creatinine) biochemistries. Part of the liver was fixed in 10% neutral buffered formalin for histopathological analysis of inflammation, necrosis and fibrosis by H&E staining and picrosirius red staining. Collagen area fraction was measured from picrosirius red stained images using an algorithm that separates the red stained collagen from non-specific staining through color subtraction and thresholding of the processed image. Sections were analyzed in random order using the same threshold value for each set. Data were deconvolved after analysis to identify group assignment. Collagen content was determined from a portion of the liver tissue using hydroxyproline analysis.

Figure 7:
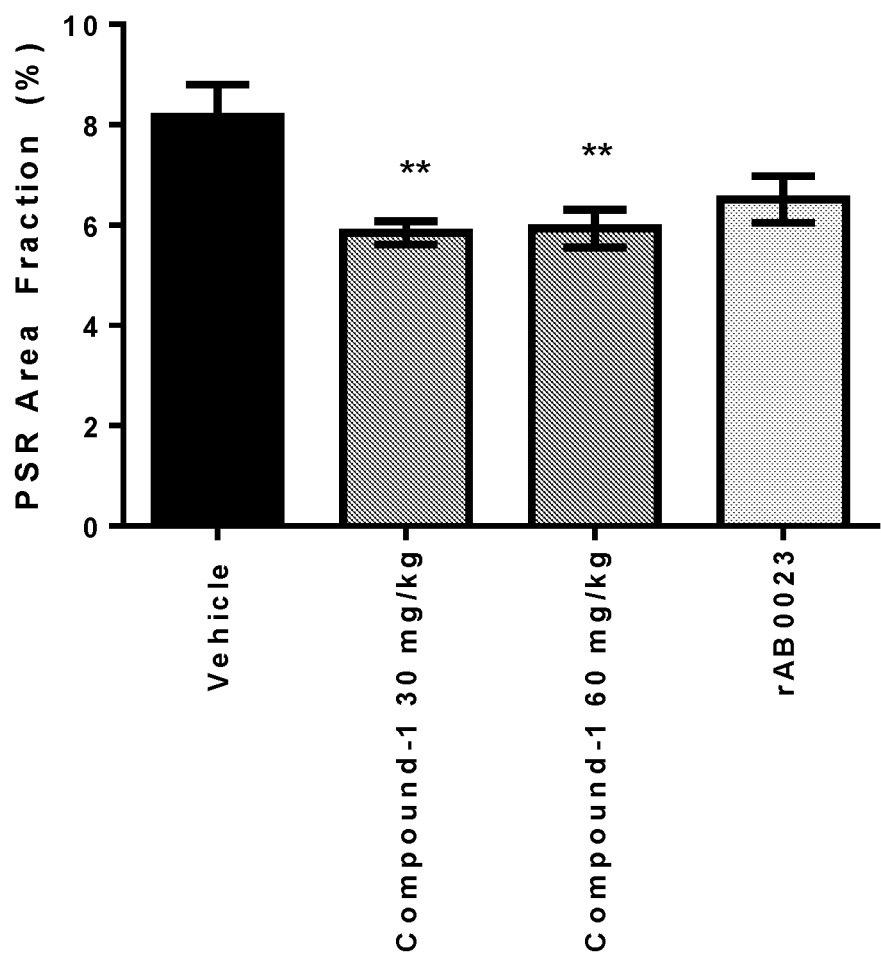
FIG. 7 shows collagen area fraction in Mdr2KO mice as measured by the percent of picrosirius red positive liver staining. Mice were treated orally with Compound 1 at 30 or 60 mg/kg QD starting at 6 weeks of age. Samples were harvested at 12 weeks of age.

Compound 1 reduced liver fibrosis, as measured by changes in picrosirius red staining, when dosed at either 30 or 60 mg/kg QD starting at 6 weeks of age and continuing through 12 weeks of age. Both dose levels demonstrated similar reduction in fibrotic area of the liver. Treatment with rAB0023, while showing trends towards reducing fibrosis did not result in a statistically significant improvement. FIG. 7 shows the quantitation of the fibrosis area as stained by picrosirius red staining (**$p<0.01$ using a 1-way ANOVA followed by Dunnett's test vs. Vehicle-treated mice).

Example B-20: Thioacetamide (TAA) Model of Liver Fibrosis in Mouse

Liver fibrosis was induced in male C57Bl/6 mice by intraperitoneal injection of thioacetamide (TAA) at a dose of 200 mg/kg 3×/week. Compound 1 was administered orally at a dose of 30 mg/kg QD with treatment starting 3 or 6 weeks after initiation of TAA administration. Liver fibrosis was studied 12 weeks after initiation of TAA. At the end of the study, mice were sacrificed by performing a laparotomy under isoflurane, blood was drawn via cardiac puncture into EDTA vacutainer tubes and the liver was harvested. Part of the liver was fixed in 10% neutral buffered formalin for subsequent histopathological analysis of inflammation and fibrosis by H&E staining and picrosirius red staining. The remaining tissue was snap frozen at −80° C. for subsequent hydroxyproline analysis of total collagen content or mRNA analyses. Serum was collected for analysis of liver biochemistries (ALT, AST, ALP, and bilirubin) as a measure of liver function.

Figure 8:
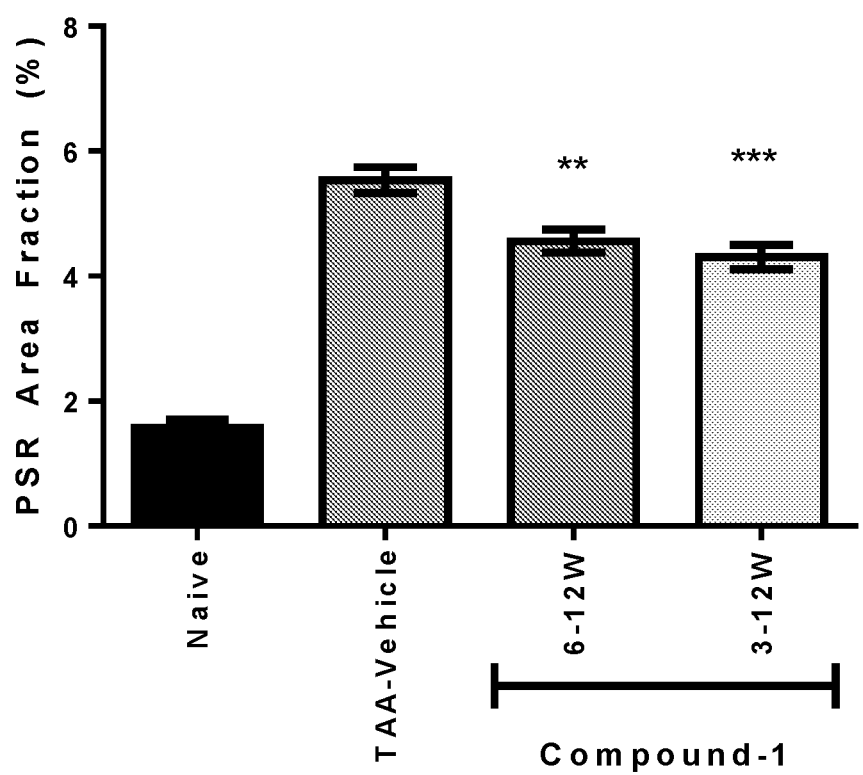
FIG. 8 shows collagen area fraction in thioacetimide (TAA) induced liver fibrosis model in mice. Mice were treated orally with Compound 1 at 30 mg/kg QD starting at either 3 or 6 weeks after TAA initiation. Samples were harvested at 12 weeks after TAA initiation.

Compound 1 reduced liver fibrosis, as measured by changes in picrosirius red staining, when dosed at 30 mg/kg/day starting at either 3 or 6 weeks after initiation of TAA. The reduction in fibrosis at 12 weeks of TAA treatment was greater when dosing was initiated at 3 weeks suggesting it may be better to treat fibrosis at an earlier stage. FIG. 8 shows the quantitation of the fibrosis area as stained by picrosirius red staining. (, *$p<0.01$, $p<0.001$, respectively, using a 1-way ANOVA followed by Dunnett's test vs. TAA-Vehicle-treated mice).

Example B-21: Diet-Induced Model of Nonalcoholic Steatohepatitis (NASH)

A nonalcoholic steatohepatitis (NASH) phenotype is induced by feeding male C57Bl/6J mice the AMLN diet (D09100301, Research Diet, US) (40% fat (18% trans-fat), 40% carbohydrates (20% fructose) and 2% cholesterol) for 26-35 weeks prior to study start and during study period. Mice are subjected to a liver biopsy under anesthesia and mice with notable steatosis and fibrosis are recruited into an efficacy study. LOXL2 inhibitors are administered orally, intraperitoneally, intravenously or subcutaneously at 30-100 mg/kg/day for 12 weeks. On or before study end, blood is sampled via the tail vein to measure ALT, triglycerides, total cholesterol, blood glucose and insulin as a measure of metabolic status. At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E, trichrome or picrosirius red staining. The remaining tissue is snap frozen at −80° C. for subsequent hydroxyproline analysis of total collagen content, total cholesterol, liver triglyceride and mRNA analyses.

Example B-22: Mouse Model of NASH Induced Through a Choline Deficient, Amino-Acid Defined (CDAA) Diet Supplemented with High Fat Content Liver fibrosis is induced by feeding C57Bl/6 mice a choline-deficient L-amino acid-defined high-fat diet (CDAAHFD) containing 60% kcal % fat and 0.1% methionine (Research Diets C/N A06071302) starting at 6 weeks of age. Once on diet for 4-6 weeks of age, mice are screened for those with deteriorating liver function and those with elevated bilirubin levels excluded. Remaining mice are assigned to groups and dosing initiated. LOXL2 inhibitors are administered orally, intraperitoneally, intravenously or subcutaneously at 30-100 mg/kg/day for an additional 8-12 weeks. At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E, trichrome and/or Picrosirius red staining. The remaining tissue is snap frozen at −80° C. for subsequent hydroxyproline analysis of total collagen content, total cholesterol, liver triglyceride and/or mRNA analyses.

Example B-23: Combination Studies in Liver Fibrosis and NASH

LOXL2 inhibitors can be used in combination with other drugs for liver fibrosis and NASH. ASK1 inhibitors are currently under investigation in the clinic in multiple fibrotic indications and demonstrate efficacy in rodent models of liver fibrosis. LOXL2 inhibitors are tested alone and in combination with ASK1 inhibitors in models of liver fibrosis described above including the TAA and CDAA-HFD models. JNK1 is a pro-fibrotic kinase downstream of ASK1 with inhibitors that demonstrate anti-fibrotic efficacy in rodent models. Inhibitors of JNK1 are under investigation clinically for IPF. LOXL2 inhibitors are tested alone and in combination with JNK1 inhibitors in models of liver fibrosis described above including the TAA and CDAA-HFD models. Additional combinations include LOXL2 inhibitors with FXR agonists (OCA), PPARα/δ/γ agonists and antagonists (GFT505); CCR2/5 dual antagonist (Cenicriviroc); drugs that target Galectin-3 (GR-MD-02), ACC-inhibitors (NDI-010976). Efficacy is assessed using either prophylactic dosing or therapeutic dosing modality (starting 4-6 weeks of age). Fibrosis is measured using histologically as described above and liver function is measured using liver enzymes. Combination therapy is advantageous when efficacy is greater than either agent alone or when the dose required for either drug is reduced thereby improving the side effect profile.

Example B-24: Laser-Induced Choroidal Neovascularization in the Eyes of Mice

Laser-induced choroidal neovascularization (CNV) is a semi-acute model for fibrosis associated with age-related macular degeneration. C57Bl/6 mice are anesthetized using ketamine/xylazine cocktail and their pupils dilated with tropicamide. Laser burns are induced in multiple locations around the optical disk using a green laser in a slit lamp delivery system. Lubricating eye drops are applied between each spot and animals monitored for signs of pain and distress. One eye of each animal is subjected to laser treatment and the contralateral eye serves as a non-injured control. At the end of the study (14-42 days post laser treatment), mice are subjected to $CO_2$ asphyxiation and cervical dislocation. Eyes are enucleated and fixed overnight in 1% paraformaldehyde or 10% formalin and embedded in paraffin. Histologic sections are stained for multiple parameters including standard H&E stains, trichrome or picrosirus red stain and various immunohistochemistry stains: i.e. anti-CD31 for blood vessels, anti-fibrillary acidic protein for glial cells, anti-CD45 for inflammatory cell infiltrate. In some studies, angiogenesis and vascular integrity are assessed using retrobulbar perfusion with FITC-labeled dextran for 2 min; the RPE-choiroid/sclera complexes are dissected and flatmounted on a slide to analyze fluorescences and vascular area. LOXL2 inhibitors are administered orally, intraperitoneally, intravenously, subcutaneously at 30-100 mg/kg/day or injected intravitreally or topically to the eye in solution.

Example B-25: The Effect of LOXL2 Inhibitor on Fibroblast-Like Synoviocyte (FLS) Invasion The effects of LOXL2 inhibitor compound will be examined in an FLS invasion study. The FLS invasion study is a two-chamber model where cells invade through Matrigel. This in vitro assay correlates with joint damage in vivo (Tolboom T C, et al. Invasiveness of fibroblast-like synoviocytes is an individual patient characteristic associated with the rate of joint destruction in patients with rheumatoid arthritis. *Arthritis Rheum* 52: 1999-2002 (2005)).

Briefly, FLS cell lines (RA and rodent FLS cell lines) are placed on the upper chamber. Over a 24 hour period cells invade through the Matrigel layer then go through pores at the base of the upper chamber. The bottom of the upper chamber is stained and cells counted.

The experiment is repeated but now the FLS cell lines are pre-treated with increasing concentrations of LOXL2 inhibitor compound. For example, the cell lines are pretreated with LOXL2 inhibitor compound for about 1-2 hours to allow for efficient binding by the compound and then placed in the upper chamber over the Matrigel layer.

Example B-26: Collagen-Induced Arthritis (CIA) Model System

A non-limiting example of the effects of LOXL2 inhibitor compounds is described below.

In this example, the effect of LOXL2 inhibitors on development of collagen-induced arthritis in a mouse model system is assessed. The DBA/1 mouse strain is used, as it is highly susceptible to CIA. On day 0 and day 21, all animals are subjected to an intradermal injection into the tail of 200 μg of collagen in 0.1 ml of a Type II collagen/Complete Freund's Adjuvant (CFA) emulsion. The location of the injection is at an approximate caudal distance of 1 cm from the base of the tail.

Male DBA/1 mice, at 6-7 weeks of age, all within +20% of mean weight, are randomly assigned to one of three treatment groups. Group 1 is a vehicle control group. The animals in this group receive 10 ml/kg of vehicle (0.5% methylcellulose), orally (PO), once daily, from Day 16. Animals in Group 2, a positive control group, receive 0.05 mg/kg dexamethasone at 10 ml/kg, PO, once daily from Day 16. Animals in Group 3 receive 0.5-60 mg/kg LOXL2 inhibitor compound, once or twice per day from Day 16. The study is terminated on Day 35 and all remaining animals are bled to exsanguination under isofluorane followed by cervical dislocation.

Mice are examined for signs of arthritogenic responses in peripheral joints on Days 0 and 16, and thereafter daily until conclusion of the study. Arthritic reactions are graded, for each paw, on an ascending scale of severity, as follows:
Grade 0: No reaction, normal.
Grade 1: Two hind or forepaw joints affected or mild diffuse erythema and swelling.
Grade 2: Three hind or forepaw joints affected or moderate diffuse erythema and swelling
Grade 3: Four hind or forepaw joints affected or marked diffuse erythema and swelling
Grade 4: Entire paw affected, severe diffuse erythema and severe swelling, unable to flex digits Clinical examinations are carried out on Day 0, Day 16 and daily thereafter. Observations include changes in skin, fur, eyes, mucous membranes, occurrence of secretions and excretions (e.g., diarrhea) and autonomic activity (e.g., lachrymation, salivation, piloerection, pupil size, and unusual respiratory pattern). Changes in gait, posture, and response to handling, as well as bizarre behaviors, tremors, convulsions, sleep and coma are also noted.

Animals are weighed shortly before tail injection on Day 0, again on Day 16, and thereafter three times weekly until termination of the study.

As an indication of experimental arthritis, the thicknesses of both hind paws are measured on Day 0, Day 16, and daily thereafter. Left and right paws are measured dorso-ventrally just above the toes and below the calcaneum, using a dial caliper (Kroeplin, Munich, Germany).

At the termination of the study, on Day 35, paws from all remaining animals are removed, skinned and fixed in 10% neutral buffered formalin. Thin sections are analyzed histologically by H&E staining for inflammation, pannus formation, cartilage damage and bone resorption.

Evaluation of data, to determine the significance of any observed effects, is based primarily on comparison of the mean group values for arthritis scores, body weight, and paw thickness measurements (all as described above) by ANOVA followed by Tukey post-hoc analysis (Winsat 2005.1 for Excel).

Example B-27: Clinical Trial for Pulmonary Fibrosis

A non-limiting example of a pulmonary fibrosis clinical trial in humans is described below.

Purpose: The purposes of this study is to assess the efficacy of Compound I, or a pharmaceutically acceptable salt or solvate thereof, as single agent or in combination, in the treatment of patients with pulmonary fibrosis, collect information on any side effects the compound may cause as single agent or in combination, and evaluate the pharmacokinetic properties of the compound as single agent or in combination.

Intervention: Patients are administered 100-2000 mg of Compound I, or a pharmaceutically acceptable salt or solvate thereof, per day as single agent or in combination.

Detailed Description: Patients will be given Compound I, or a pharmaceutically acceptable salt or solvate thereof, orally once or twice a day as single agent or in combination. Prior to each dosing cycle, a physical exam, blood work and assessment of any side effects will be performed.

Primary Outcome Measures: Progression-free survival, defined as free of death or a decrease from baseline in the FVC of at least 10%.

Secondary Outcome Measures: Number of Acute Exacerbations of IPF; health related quality of life; $PO_2$ at rest and at exercise from baseline; $P(A-a)O_2$ at rest and at exercise from baseline; Predicted FEV1 from baseline; forced expiratory volume in one second (FEV1) to FVC from baseline; plethysmographic lung volumes from baseline; diffusion capacity for carbon monoxide (DLco) from baseline; Six-Minute Walk test, from baseline: resting and 6 minute SpO2, presence or absence of desaturation to 88% or lower at the end of the six minute walk, walked distance; Pre and post modified Borg dyspnea scores; scoring of extent of lung fibrosis on HRCT, according to two independent chest radiologists, form baseline; number and severity of adverse effects.

Eligibility: Male and female subjects that are 40 years to 80 years.

Inclusion Criteria: Clinical symptoms of IPF for at least 3 months; forced vital capacity (FVC) between 50 to 90% of the predicted value; DLco at least 35% of the predicted value; PaO2>55 mm Hg while breathing ambient air at rest; High-resolution computed tomography (HRCT) showing definite or probable criteria of IPF.

Exclusion Criteria: Clinically significant exposure to known fibrogenic agents (birds, molds, asbestos, radiation and drugs known to cause pulmonary fibrosis (amiodarone, nitrofurantoin, bleomicin, etc)); history of neurofibromatosis, Hermansky-Pudlak syndrome, metabolic storage disorders, etc.; history of fever, weight loss, myalgias, arthralgias, skin rash, arthritis; active infection within one week before enrollment; alternative cause of interstitial lung disease; ratio of the forced expiratory volume in one second (VEF1) to FVC of less than 0.6 after the use of a bronchodilator; residual volume more than 120% of the predicted value (when available); more than 20% of lymphocytes or eosinophils in bronchoalveolar lavage (BAL) (when available); granulomas, infection or malignancy in the transbronchial or surgical biopsy (when available); previous therapy with azathioprine, prednisolone (>0.5 mg/kg/day or more for at least 3 months), cyclophosphamide or novel biotech drugs; unstable cardiovascular or neurologic disease; uncontrolled diabetes; pregnancy; lactation; likelihood of death, as predicted by the investigator, within the next year; white cell blood count <4000/mm3; platelet count <100000/mm3; Hematocrit <30% or >59%; liver enzymes more than 3 times the upper limit of the normal range; creatinine level >1.5 mg/dL; albumin level <3 g/dL; refusal to sign informed consent by patient or guardian.

Example B-28: Clinical Trial for Liver Fibrosis

A non-limiting example of a liver fibrosis clinical trial in humans is described below.

Purpose: The purposes of this study are to assess the efficacy of Compound I, or a pharmaceutically acceptable salt or solvate thereof, as single agent or in combination, in the treatment of patients with liver fibrosis, collect information on any side effects the compound may cause as single agent or in combination, and evaluate the pharmacokinetic properties of the compound as single agent or in combination.

Intervention: Patients are administered 100-2000 mg of Compound I, or a pharmaceutically acceptable salt or solvate thereof, per day as single agent or in combination.

Detailed Description: Patients will be given Compound I, or a pharmaceutically acceptable salt or solvate thereof, orally once or twice a day as single agent or in combination. Prior to each dosing cycle, a physical exam, blood work and assessment of any side effects will be performed.

Primary Outcome Measures: Liver enzymes (ALT, AST, ALP), liver biopsy

Secondary Outcome Measures: Pharmacodynamic markers may include: Tissue PD markers through mRNA expression, autotaxin, LOXL2, LOX, Other LOXL proteins, αSMA, Collagen 1A1, NF-κB1, Caspase 1, SMAD, and NOD; Serum and plasma PD markers include: AST-to-platelet ratio index (APRI), autotaxin activity, concentrations of LOXL2, Osteopontin, Hyaluronic Acid, CXCL 9, 10 and 11, MMP1, MMP3, MMP9, TIMP1, CD40L, TGF-β1, ET-1, VEGF, GAL3, IL-6/IL-8/TNFα/IFNγ, α2-macroglobulin, Apolipoprotein A1, PINP, PIIINP, PVCP-1230, PDGF; Assessing the effects of chronic dosing on liver structure and fibrotic markers; incidence of adverse events resulting from the administration of multiple doses of compound.

Eligibility: Male and female subjects that are 18 to 60 years old.

Inclusion Criteria: Stage 1-3 fibrosis by Metavir score on a liver biopsy; Body mass index <36 kg/m2.

Exclusion Criteria: Any evidence of hepatic decompensation past or present; subjects currently abusing amphetamines, cocaine, opiates, or alcohol; clinically significant cardiac disease; history of cancer, other than non-melanomatous skin cancer, within 5 years prior to screening; systemic fungal, bacterial, viral, or other infection that is not controlled; use of systemic immunosuppressants within 28 days of the Pre-treatment Phase; use of approved therapy for hepatitis C or hepatitis B virus within 28 days of the Pre-treatment Phase; pregnant or lactating; history of bleeding diathesis within the last 6 months of study Day 1.

Example B-29: Clinical Trial for Fatty Liver Disease/Steatosis (NAFLD, NASH)

A non-limiting example of a fatty liver disease/steatosis clinical trial in humans is described below.

Purpose: The purposes of this study are to assess the efficacy of Compound I, or a pharmaceutically acceptable salt or solvate thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention: Patients are administered 10-2000 mg of Compound I, or a pharmaceutically acceptable salt or solvate thereof, per day as single agent or in combination.

Detailed Description: Patients will be given Compound I, or a pharmaceutically acceptable salt or solvate thereof, orally once or twice a day as single agent or in combination. Prior to each dosing cycle, a physical exam, blood work and assessment of any side effects will be performed.

Eligibility: Male and female subjects that are 21 to 80 years old.

Inclusion Criteria: Patients with clinically confirmed diagnosis of non-alcohol fatty liver disease or non-alcohol steatohepatitis; histologic evidence of definite or probable nonalcoholic steatohepatitis (NASH) based upon a liver biopsy obtained no more than 90 days prior to randomization and a nonalcoholic fatty liver disease activity score (NAS) of 4 or greater.

Exclusion Criteria: Current or history of significant alcohol consumption, use of drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to randomization, prior or planned (during the study period) bariatric surgery (e.g., gastroplasty, roux-en-Y gastric bypass), uncontrolled diabetes defined as Hemoglobin A1c 9.5% or higher within 60 days prior to enrollment, presence of cirrhosis on liver biopsy, platelet count below 100,000/mm3; Clinical evidence of hepatic decompensation as defined by the presence of any of the following abnormalities: serum albumin less than 3.2 grams/deciliter (g/dL), INR (international normalized ratio) greater than 1.3, direct bilirubin greater than 1.3 milligrams per deciliter (mg/dL), history of esophageal varices, ascites or hepatic encephalopathy; Evidence of other forms of chronic liver disease: hepatitis B as defined by presence of hepatitis B surface antigen (HBsAg), hepatitis C as defined by presence of hepatitis C virus (HCV) ribonucleic acid (RNA) or positive hepatitis C antibody (anti-HCV), evidence of ongoing autoimmune liver disease as defined by compatible liver histology, primary biliary cirrhosis, primary sclerosing cholangitis, Wilson's disease, Alpha-1-antitrypsin (A1AT) deficiency, history of hemochromatosis or iron overload, drug-induced liver disease as defined on the basis of typical exposure and history, known bile duct obstruction, suspected or proven liver cancer, any other type of liver disease other than nonalcoholic steatohepatitis (NASH); serum alanine aminotransferase (ALT) greater than 300 units per liter (U/L); serum creatinine of 2.0 mg/dL or greater; use of ursodeoxycholic acid (Ursodiol, Urso) within 90 days prior to enrollment inability to safely obtain a liver biopsy, history of biliary diversion, known positivity for Human Immunodeficiency Virus (HIV) infection; pregnancy, planned pregnancy, potential for pregnancy and unwillingness to use effective birth control during the trial, breast feeding Primary Outcome Measures: liver function tests, liver biopsy, NAS score Secondary Outcome Measures: fibrotic biomarkers, liver imaging (ultrasound, MRI), insulin resistance as measure by HOMA-IR, lipid panel.

Example B-30: Clinical Trial for Pancreatic Cancer

A non-limiting example of a pancreatic cancer clinical trial in humans is described below.

Purpose: The purposes of this study are to assess the efficacy of Compound I, or a pharmaceutically acceptable salt or solvate thereof, as single agent or in combination, in the treatment of patients with pancreatic cancer, collect information on any side effects the compound may cause as single agent or in combination, and evaluate the pharmacokinetic properties of the compound as single agent or in combination.

Intervention: Patients are administered 100-2000 mg of Compound I, or a pharmaceutically acceptable salt or solvate thereof, per day as single agent or in combination.

Detailed Description: Patients will be given Compound I, or a pharmaceutically acceptable salt or solvate thereof, orally once or twice a day as single agent or in combination. Prior to each dosing cycle, a physical exam, blood work and assessment of any side effects will be performed.

Eligibility: Male and female subjects that are 21 to 80 years old with advanced pancreatic cancer.

Inclusion Criteria: Radiographic or clinical evidence of measurable advanced pancreatic carcinoma (Stage II, II, IV). Subjects must have measurable disease at least 2 cm in diameter. ECOG performance status of 0 or 1

Exclusion Criteria: Prior history of malignancy (except basal cell or squamous cell carcinoma or carcinoma in situ of the breast) unless the subject has been free of disease for > or = to 1 year. Moderate or severe cardiac disease; Active infection; Not pregnant or nursing; Negative pregnancy test; Fertile patients must use effective contraception during and for ≥3 months after completion of study treatment; Able to swallow oral medication; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures: Progression free survival, overall survival, worsening of pain, onset of pain Secondary Outcome Measures: tumor size/response (RECIST)

Example B-31: Clinical Trial for Hepatocellular Carcinoma (HCC)

A non-limiting example of a hepatocellular carcinoma clinical trial in humans is described below.

Purpose: The purposes of this study are to assess the efficacy of Compound I, or a pharmaceutically acceptable salt or solvate thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention: Patients are administered 100-2000 mg of Compound I, or a pharmaceutically acceptable salt or solvate thereof, per day as single agent or in combination.

Detailed Description: Patients will be given Compound I, or a pharmaceutically acceptable salt or solvate thereof, orally once or twice a day as single agent or in combination. Prior to each dosing cycle, a physical exam, blood work and assessment of any side effects will be performed.

Eligibility: Male and female subjects that are 21 to 80 years old.

Inclusion Criteria: Patients with histopathologically or clinically confirmed diagnosis of hepatocellular carcinoma; unresponsive to standard therapy or for whom standard therapy is intolerable, or for whom there is no appropriate therapy; ECOG performance status score of 0-2.

Exclusion Criteria: Patients with a primary malignant tumor; history of liver transplant; brain metastases; psychiatric disorder that might cause difficulty in obtaining informed consent or in conducting the trial; Not pregnant or nursing; Fertile patients must use effective contraception during and for ≥3 months after completion of study treatment; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures: time to progression, progression free survival, overall response (RECIST)

Secondary Outcome Measures: liver function tests, tumor biomarkers

The examples and embodiments described herein are for illustrative purposes only and various modifications or changes suggested to persons skilled in the art are to be included within the spirit and purview of this application and scope of the appended claims.

What is claimed is:

1. A method for treating myelofibrosis in a mammal subject comprising administering to the mammal in need thereof an oral dosage form comprising a compound that is trans-(3-((4-(aminomethyl)-6-(trifluoromethyl)pyridin-2-yl)oxy)phenyl)(3-fluoro-4-hydroxypyrrolidin-1-yl)methanone, or a pharmaceutically acceptable salt or solvate thereof; wherein the myelofibrosis is primary myelofibrosis or secondary myelofibrosis.

2. The method of claim 1, wherein the oral dosage is administered in combination with at least one additional therapeutic agent to the mammal.

3. The method of claim 2, wherein the at least one additional therapeutic agent is ruxolitinib.

4. The method of claim 2, wherein the at least one additional therapeutic agent is a corticosteroid, an immunosuppressant, pirfenidone, nintedanib, imatinab, a tyrosine kinase inhibitor, PBI-4050, recombinant pentraxin-2/SAP (PRM-151), aerosol IFN-g, an inhibitor of CTGF activity, a LPA receptor antagonist, an autotaxin inhibitor, a galectin-3 inhibitor, tipelukast, an integrin antagonist, a PI3K inhibitor, a JNK inhibitor, a ROCK inhibitor, an anti-IL-13 compound, a CCL2 antagonist, a CCR2 antagonist, an anti-CD20 compound, an anticoagulant, a collagen V treatment, an ASK1 inhibitor, or combination thereof.

5. A method for treating myelofibrosis in a mammal subject comprising administering to the mammal in need thereof a compound that is trans-(3-((4(aminomethyl)-6-(trifluoromethyl) pyridin-2-yl)oxy)phenyl)(3-fluoro-4-hydroxypyrrolidin-1-yl)methanone as a pharmaceutically acceptable mesylate salt thereof; wherein the myelofibrosis is primary myelofibrosis or secondary myelofibrosis.

6. The method of claim 1, wherein the compound is (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, (S,S)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof, or a mixture thereof.

7. The method of claim 1, wherein the compound is (R,R)-trans-(3-((4-(aminomethyl)-6-(trifluoromethyl)pyridin-2-yl)oxy)phenyl)(3-fluoro-4-hydroxypyrrolidin-1-yl)methanone or a pharmaceutically acceptable salt or solvate thereof.

8. The method of claim 7, wherein the pharmaceutically acceptable salt of (R,R)-trans-(3-((4-(aminomethyl)-6-(trifluoromethyl)pyridin-2-yl)oxy)phenyl)(3-fluoro-4-hydroxypyrrolidin-1-yl)methanone is formed from (R,R)-trans-(3-((4-(aminomethyl)-6-(trifluoromethyl)pyridin-2-yl)oxy)phenyl)(3-fluoro-4-hydroxypyrrolidin-1-yl)methanone and an acid selected from the group consisting of hydrochloride acid, hydrobromic acid, sulfuric acid, phosphoric acid, nitric acid, metaphosphoric acid, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; (L)-ascorbic acid; (L)-aspartic acid; benzenesulfonic acid; benzoic acid; (+)-camphoric acid; (+)-camphor-10-sulfonic acid; capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; (D)-glucoheptonic acid; (D)-gluconic acid; (D)-glucuronic acid; glutamic acid; glutaric acid; glycerophosphoric acid; glycolic acid; hippuric acid; isobutyric acid; (DL)-lactic acid; lactobionic acid; lauric acid; maleic acid; L-(−)-malic acid; malonic acid; (DL)-mandelic acid; methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; L-(−)-pyroglutamic acid; salicylic acid; sebacic acid; stearic acid; succinic acid; sulfuric acid; L-(+)-tartaric acid; thiocyanic acid; (p)-toluenesulfonic acid; and undecylenic acid.

9. The method of claim 7, wherein (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as a mesylate salt, hydrochloride salt, sulfate salt, maleate salt, phosphate salt, L-tartrate salt, fumarate salt, succinate salt, citrate salt or acetate salt.

10. The method of claim 7, wherein (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal as a mesylate salt.

11. The method of claim 10, wherein 250 mg, 500 mg, 750 mg, 1000 mg, 1250 mg, 1500 mg, 1750 mg, or 2000 mg of the mesylate salt of (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal per day.

12. The method of claim 10, wherein 2000 mg of the mesylate salt of (R,R)-trans-(3-((4-(aminomethyl)-6-(trifluoromethyl)pyridin-2-yl)oxy)phenyl)(3-fluoro-4-hydroxypyrrolidin-1-yl)methanone is administered to the mammal per day.

13. The method of claim 10, wherein 1000 mg of the mesylate salt of (R,R)-trans-(3-((4-(aminomethyl)-6-(trifluoromethyl)pyridin-2-yl)oxy)phenyl)(3-fluoro-4-hydroxy-pyrrolidin-1-yl)methanone is administered to the mammal twice a day.

14. The method of claim 7, wherein:
    the compound reduces serum LOXL2 (sLOXL2) levels in the mammal.

15. The method of claim 1, wherein the myelofibrosis is primary, post polycythemia vera or post essential thrombocythemia myelofibrosis.

* * * * *